US010376251B2

(12) United States Patent
Shibley et al.

(10) Patent No.: US 10,376,251 B2
(45) Date of Patent: Aug. 13, 2019

(54) PNEUMOPERITONEUM DEVICE

(71) Applicant: Atropos Limited, Bray, County Wicklow (IE)

(72) Inventors: Kirk Anthony Shibley, Wayzata, MN (US); Frank Bonadio, Bray (IE); Trevor Vaugh, Birr (IE); Shane Joseph MacNally, Delgany (IE)

(73) Assignee: Atropos Limited, County Wicklow (IE)

( * ) Notice: Subject to any disclaimer, the term of this patent is extended or adjusted under 35 U.S.C. 154(b) by 675 days.

(21) Appl. No.: 15/060,231

(22) Filed: Mar. 3, 2016

(65) Prior Publication Data

US 2016/0183932 A1 Jun. 30, 2016

Related U.S. Application Data

(63) Continuation of application No. 13/725,148, filed on Dec. 21, 2012, now abandoned.

(Continued)

(51) Int. Cl.
*A61B 17/02* (2006.01)
*A61B 17/00* (2006.01)
(Continued)

(52) U.S. Cl.
CPC .... *A61B 17/00234* (2013.01); *A61B 17/0218* (2013.01); *A61B 17/22* (2013.01);
(Continued)

(58) Field of Classification Search
CPC ...... A61B 17/3423; A61B 2017/00287; A61B 17/0293
(Continued)

(56) References Cited

U.S. PATENT DOCUMENTS 30,471 A 10/1860 Dudley
4,346,699 A 8/1982 Little et al.
(Continued)

FOREIGN PATENT DOCUMENTS

CN 100477968 C 4/2009
CN 202397525 U 8/2012
(Continued)

OTHER PUBLICATIONS

Matsuda, Tadashi, et al., Future of Urologic Laparascopy, World J. Surg. 24, pp. 1172-1175, Jul. 17, 2000.
Requirement for Restriction/Election of Species from U.S. Appl. No. 13/725,148, dated Jun. 5, 2014 (8 pages).
(Continued)

*Primary Examiner* — Si Ming Ku
(74) *Attorney, Agent, or Firm* — Bookoff McAndrews, PLLC

(57) ABSTRACT

A bag with one or more openings is placed within a body cavity. Excized tissue is placed within the opening of a deflated bag. One or more openings of the bag are withdrawn outside the body cavity and the bag is inflated. Instruments including laparoscopic visualization are placed within the inflated bag that remains within the body cavity. The tissue retained within the bag is morcellated/crushed/reduced and removed. The bag is deflated and removed with residual tissue/blood/fluids inside. The tissue to be removed is retained in the bag which prevents potentially harmful material such as cancerous cells from being released in the body cavity.

17 Claims, 51 Drawing Sheets

Related U.S. Application Data

(60) Provisional application No. 61/742,125, filed on Aug. 3, 2012, provisional application No. 61/580,088, filed on Dec. 23, 2011.

(51) Int. Cl.
*A61M 13/00* (2006.01)
*A61B 17/34* (2006.01)
*A61B 17/22* (2006.01)
*A61J 1/10* (2006.01)
*A61B 17/32* (2006.01)
*A61B 17/42* (2006.01)

(52) U.S. Cl.
CPC ............ *A61B 17/3423* (2013.01); *A61J 1/10* (2013.01); *A61M 13/003* (2013.01); *A61B 17/0293* (2013.01); *A61B 17/3474* (2013.01); *A61B 2017/00287* (2013.01); *A61B 2017/00557* (2013.01); *A61B 2017/00659* (2013.01); *A61B 2017/00946* (2013.01); *A61B 2017/00951* (2013.01); *A61B 2017/0225* (2013.01); *A61B 2017/22061* (2013.01); *A61B 2017/320024* (2013.01); *A61B 2017/3429* (2013.01); *A61B 2017/3447* (2013.01); *A61B 2017/3466* (2013.01); *A61B 2017/4216* (2013.01)

(58) Field of Classification Search
USPC .................................. 600/204–209, 235–242
See application file for complete search history.

(56) References Cited

U.S. PATENT DOCUMENTS

| | | |
|---|---|---|
| 5,037,379 A | 8/1991 | Clayman et al. |
| 5,074,867 A | 12/1991 | Wilk |
| 5,147,371 A | 9/1992 | Washington et al. |
| 5,190,555 A | 3/1993 | Wetter et al. |
| 5,192,284 A | 3/1993 | Pleatman |
| 5,215,521 A | 6/1993 | Cochran et al. |
| 5,224,930 A | 7/1993 | Spaeth et al. |
| 5,312,416 A | 5/1994 | Spaeth et al. |
| 5,320,627 A | 6/1994 | Sorensen et al. |
| 5,330,483 A | 7/1994 | Heaven et al. |
| 5,337,754 A | 8/1994 | Heaven et al. |
| 5,341,815 A | 8/1994 | Cofone et al. |
| 5,350,387 A | 9/1994 | Semm |
| 5,352,184 A | 10/1994 | Goldberg et al. |
| 5,353,784 A | 10/1994 | Nady-Mohamed |
| 5,354,303 A | 10/1994 | Spaeth et al. |
| 5,368,545 A | 11/1994 | Schaller et al. |
| 5,465,731 A | 11/1995 | Bell et al. |
| 5,480,404 A | 1/1996 | Kammerer et al. |
| 5,522,790 A | 6/1996 | Moll et al. |
| 5,562,603 A | 10/1996 | Moll et al. |
| 5,611,803 A | 3/1997 | Heaven et al. |
| 5,618,296 A | 4/1997 | Sorensen et al. |
| 5,640,977 A | 6/1997 | Leahy et al. |
| 5,645,083 A | 7/1997 | Essig et al. |
| 5,735,289 A | 4/1998 | Pfeffer et al. |
| 5,755,724 A | 5/1998 | Yoon |
| 5,769,794 A | 6/1998 | Conlan et al. |
| 5,785,677 A | 7/1998 | Auweiler |
| 5,788,709 A | 8/1998 | Riek et al. |
| 5,813,409 A | 9/1998 | Leahy et al. |
| 5,836,936 A | 11/1998 | Cuschieri |
| 5,895,392 A | 4/1999 | Riek et al. |
| 5,980,544 A | 11/1999 | Vaitekunas |
| 5,997,547 A | 12/1999 | Nakao et al. |
| 6,004,330 A | 12/1999 | Middleman et al. |
| 6,036,681 A | 3/2000 | Hooven |
| 6,162,235 A | 12/2000 | Vaitekunas |
| 6,206,889 B1 | 3/2001 | Bennardo |
| 6,228,095 B1 | 5/2001 | Dennis |
| 6,270,505 B1 | 8/2001 | Yoshida et al. |
| 6,344,026 B1 | 2/2002 | Burbank et al. |
| 6,350,267 B1 | 2/2002 | Stefanchik |
| 6,383,197 B1 | 5/2002 | Conlon et al. |
| 6,409,733 B1 | 6/2002 | Conlon et al. |
| 6,450,983 B1 | 9/2002 | Rambo |
| 6,508,773 B2 | 1/2003 | Burbank et al. |
| 6,613,952 B2 | 9/2003 | Rambo |
| 6,659,105 B2 | 12/2003 | Burbank et al. |
| 6,685,628 B2 | 2/2004 | Vu |
| 6,887,255 B2 | 5/2005 | Shimm |
| 7,163,510 B2 | 1/2007 | Kahle et al. |
| 7,613,510 B2 | 11/2009 | Rentea et al. |
| 7,670,338 B2 | 3/2010 | Albrecht et al. |
| 7,670,346 B2 | 3/2010 | Whitfield |
| 7,955,292 B2 | 6/2011 | Leroy et al. |
| 8,152,820 B2 | 4/2012 | Mohamed et al. |
| 8,187,178 B2 | 5/2012 | Bonadio et al. |
| 8,282,572 B2 | 10/2012 | Bilsbury |
| 8,409,217 B2 | 4/2013 | Parihar et al. |
| 8,486,087 B2 | 7/2013 | Fleming |
| 8,821,377 B2 * | 9/2014 | Collins ............... A61B 17/221 128/898 |
| 8,827,968 B2 | 9/2014 | Taylor et al. |
| 8,920,431 B2 | 12/2014 | Shibley et al. |
| 8,956,286 B2 | 2/2015 | Shibley et al. |
| 9,044,210 B1 | 6/2015 | Hoyte et al. |
| 9,265,492 B2 | 2/2016 | Shibley et al. |
| 9,655,644 B2 | 5/2017 | Collins |
| 9,877,893 B2 | 1/2018 | Taylor et al. |
| 2004/0097960 A1 | 5/2004 | Terachi et al. |
| 2004/0138587 A1 | 7/2004 | Lyons, IV |
| 2004/0158261 A1 | 8/2004 | Vu |
| 2004/0215063 A1 | 10/2004 | Bonadio et al. |
| 2005/0090717 A1 | 4/2005 | Bonadio et al. |
| 2006/0200169 A1 | 9/2006 | Sniffin |
| 2006/0241586 A1 | 10/2006 | Wilk |
| 2007/0135780 A1 | 6/2007 | Pagedas |
| 2007/0135781 A1 | 6/2007 | Hart |
| 2008/0033451 A1 | 2/2008 | Rieber et al. |
| 2009/0043315 A1 | 2/2009 | Moon |
| 2009/0326546 A1 | 12/2009 | Mohamed et al. |
| 2010/0016799 A1 | 1/2010 | Schweitzer et al. |
| 2010/0219091 A1 | 9/2010 | Turner |
| 2010/0228092 A1 | 9/2010 | Ortiz et al. |
| 2011/0071359 A1 | 3/2011 | Bonadio et al. |
| 2011/0071361 A1 | 3/2011 | Mollenauer et al. |
| 2011/0087235 A1 | 4/2011 | Taylor et al. |
| 2011/0299799 A1 | 12/2011 | Towe |
| 2012/0277758 A1 | 11/2012 | Davis et al. |
| 2013/0131457 A1 | 5/2013 | Seckin |
| 2013/0131689 A1 | 5/2013 | Farascioni |
| 2013/0184536 A1 | 7/2013 | Shibley et al. |
| 2013/0218170 A1 | 8/2013 | Uznanski et al. |
| 2013/0253267 A1 | 9/2013 | Collins |
| 2015/0305772 A1 | 10/2015 | McCauley |
| 2016/0100857 A1 | 4/2016 | Wachli et al. |
| 2016/0135798 A1 | 5/2016 | Macleod et al. |
| 2016/0183932 A1 | 6/2016 | Shibley et al. |
| 2016/0199051 A1 | 7/2016 | Shibley et al. |
| 2016/0242751 A1 | 8/2016 | Bonadio et al. |
| 2017/0049427 A1 | 2/2017 | Do et al. |
| 2017/0056065 A1 | 3/2017 | Do et al. |
| 2017/0231611 A1 | 8/2017 | Holsten et al. |
| 2017/0325798 A1 | 11/2017 | Prior |
| 2017/0325800 A1 | 11/2017 | Prior |
| 2018/0021030 A1 | 1/2018 | Fridlin |

FOREIGN PATENT DOCUMENTS

| | | |
|---|---|---|
| CN | 205683099 U | 11/2016 |
| DE | 4405831 A1 | 8/1995 |
| DE | 4405831 C2 | 9/1996 |
| EP | 0 578 997 A1 | 1/1994 |
| EP | 0 465 051 B1 | 8/1995 |
| EP | 1935356 A | 6/2008 |
| EP | 2143393 A | 1/2010 |
| EP | 2 265 186 B1 | 11/2011 |

(56) References Cited

FOREIGN PATENT DOCUMENTS

| | | |
|---|---|---|
| GB | 2460099 A | 11/2009 |
| IN | 5813/CHE/2014 | 12/2014 |
| JP | H04-309340 | 10/1992 |
| JP | H06-319795 A | 11/1994 |
| JP | H08-140983 | 6/1996 |
| JP | H08-294493 A | 11/1996 |
| JP | H09-173337 | 7/1997 |
| JP | 2009-039504 | 2/2009 |
| JP | 2010-207578 | 9/2010 |
| JP | 2011-103926 | 6/2011 |
| WO | WO 95/09666 | 4/1995 |
| WO | WO 98/09569 | 3/1998 |
| WO | WO 2005/025427 A1 | 3/2005 |
| WO | WO 2006/044797 A2 | 4/2006 |
| WO | WO 2009/158301 A1 | 12/2009 |
| WO | WO 2010/099541 A1 | 9/2010 |
| WO | WO 2011/090866 A2 | 7/2011 |
| WO | WO 2011/110836 A2 | 9/2011 |
| WO | WO 2012/035524 A2 | 3/2012 |
| WO | WO 2013/054093 A1 | 4/2013 |
| WO | WO 2013/075103 A1 | 5/2013 |
| WO | WO 2013/093030 | 6/2013 |
| WO | WO 2014/207077 A1 | 12/2014 |
| WO | WO 2015/151117 A1 | 10/2015 |
| WO | WO 2016/028429 | 2/2016 |
| WO | WO 2016/130982 A1 | 8/2016 |

OTHER PUBLICATIONS

Reply to Requirement for Restriction/Election of Species from U.S. Appl. No. 13/725,148, filed Aug. 5, 2014 (8 pages).

Non-Final Office Action from U.S. Appl. No. 13/725,148, dated Aug. 27, 2014 (13 pages).

Reply to Office Action filed on Sep. 17, 2015, in U.S. Appl. No. 13/735,148 (16 pages).

Restriction Requirement in U.S. Appl. No. 14/996,610, dated Jul. 29, 2016 (6 pages).

International Search Report and Written Opinion for Application No. PCT/EP2015/079163, dated Mar. 23, 2016 (11 pages).

International Preliminary Report on Patentability for corresponding International No. PCT/EP2012/076703, dated Jun. 24, 2014 (9 pages).

Non-Final Office Action from U.S. Appl. No. 14/251,362, dated Jun. 18, 2014 (6 pages).

Reply to Office Action from U.S. Appl. No. 14/251,362, filed Jul. 3, 2014 (13 pages).

Requirement for Restriction/Election of Species from U.S. Appl. No. 14/251,416, dated Jun. 16, 2014 (9 pages).

International Search Report dated Nov. 14, 2014, in PCT/EP2014/063458 (8 pages).

Restriction Requirement dated Jun. 11, 2015, in U.S. Appl. No. 14/584,865 (7 pages).

Reply to Restriction Requirement filed on Sep. 11, 2015, in U.S. Appl. No. 14/584,865 (2 pages).

\* cited by examiner

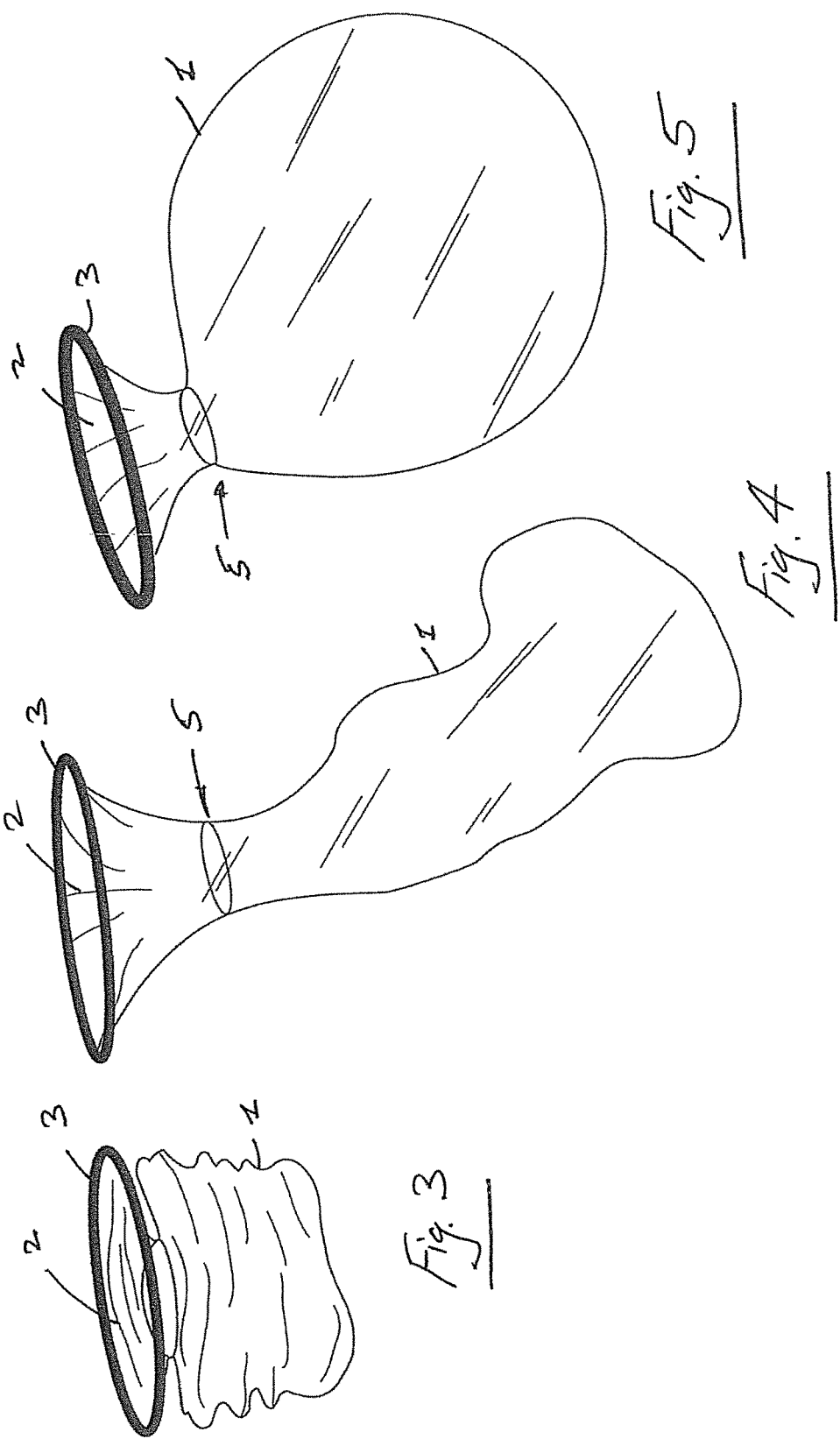

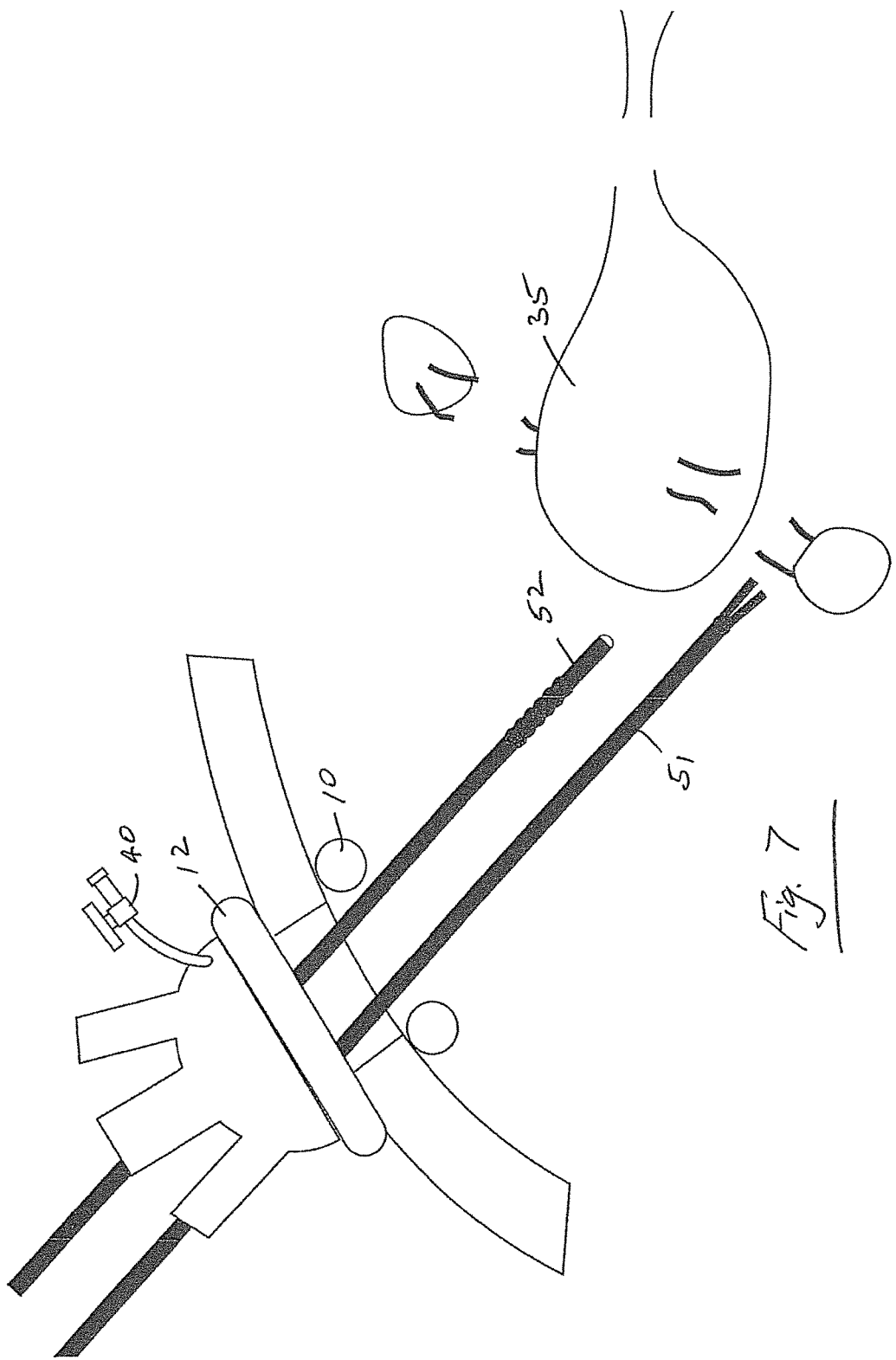

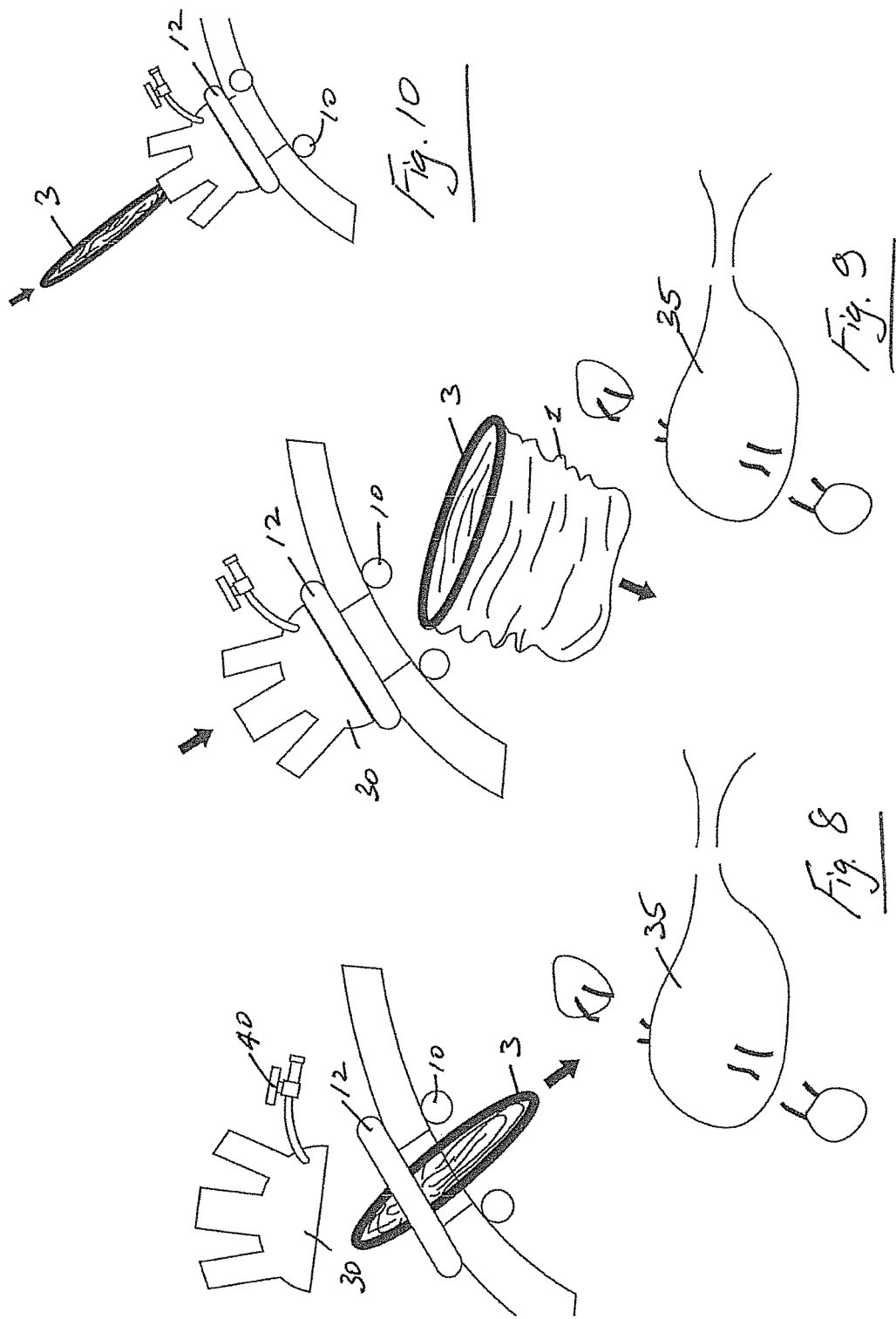

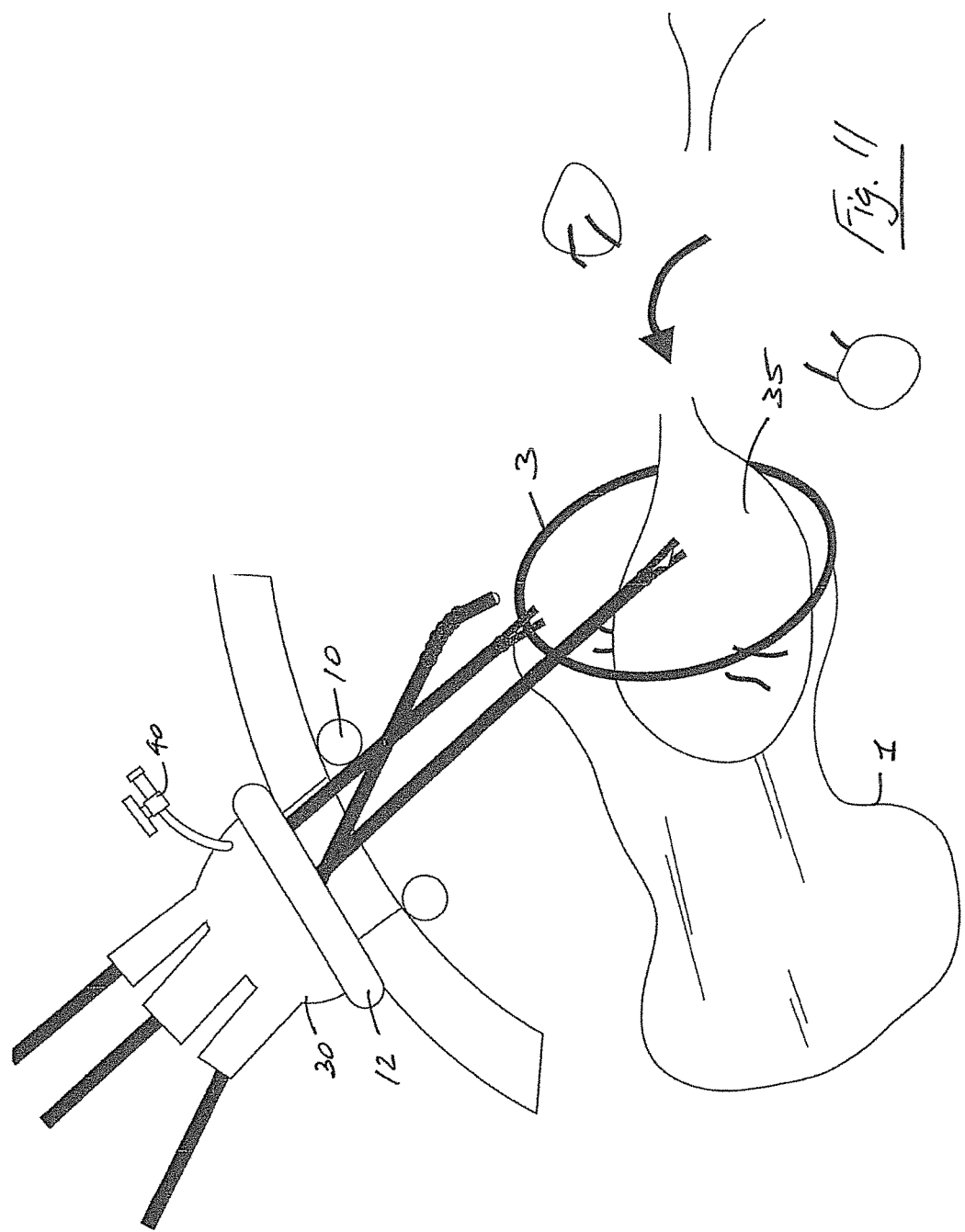

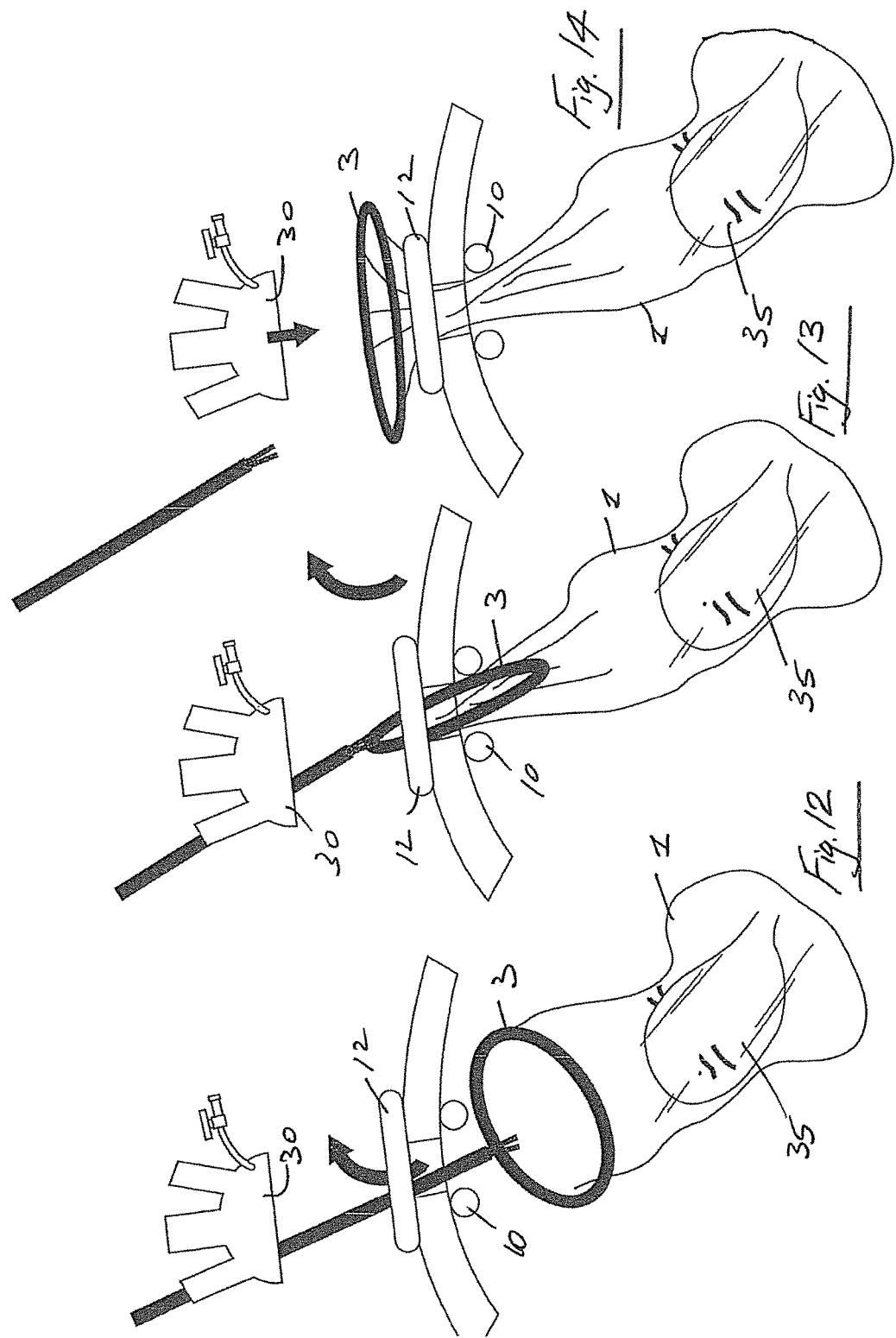

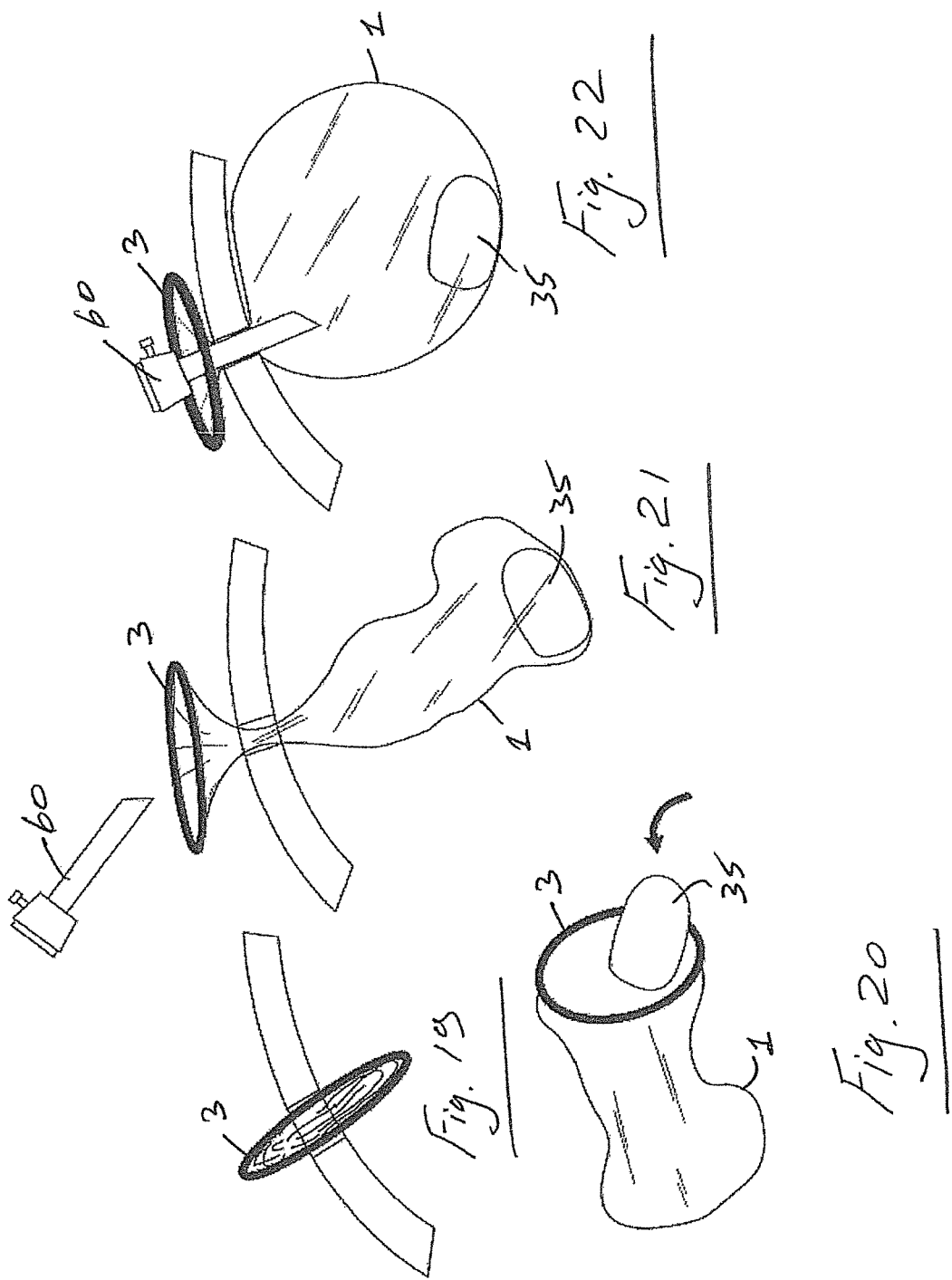

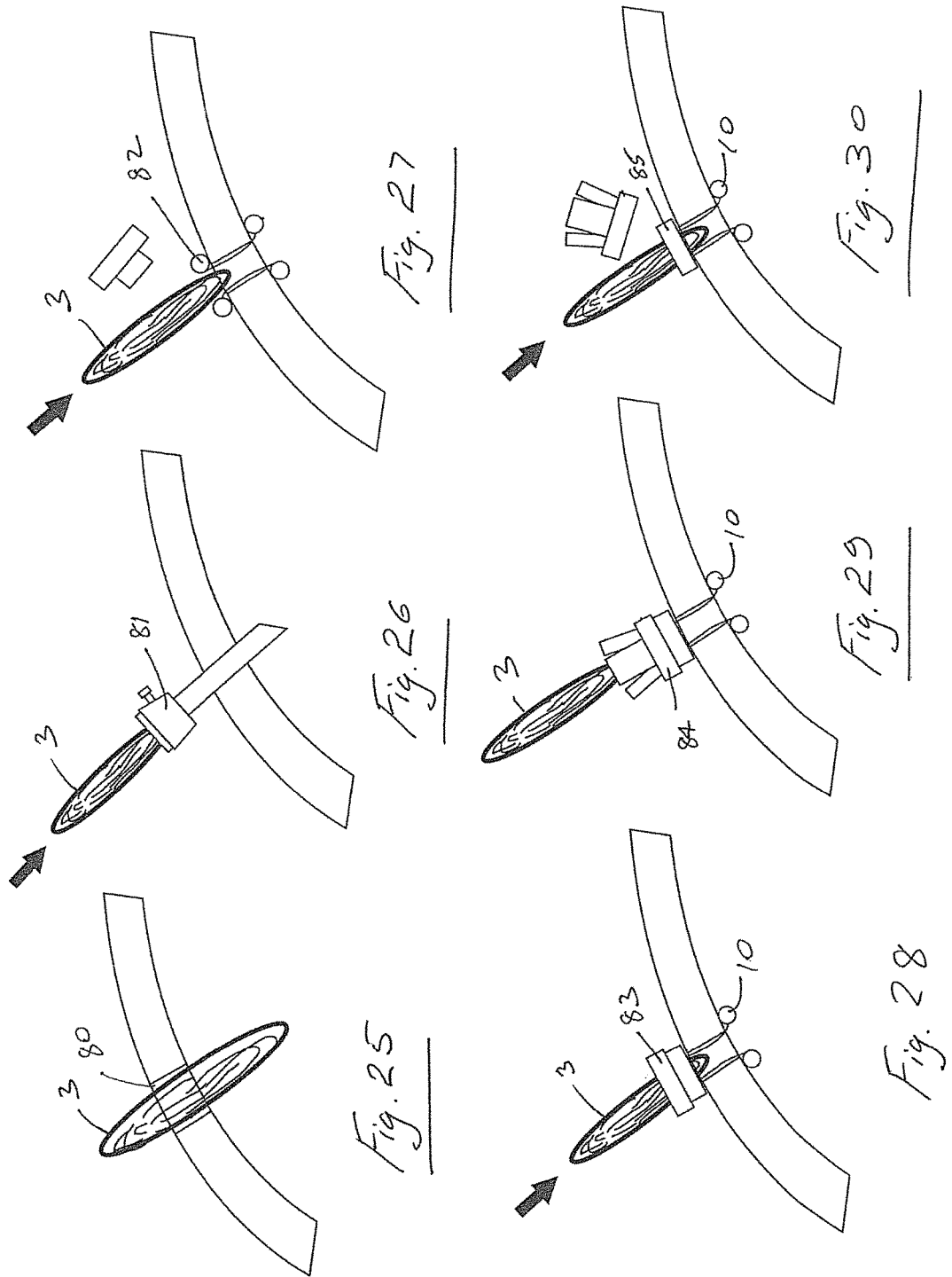

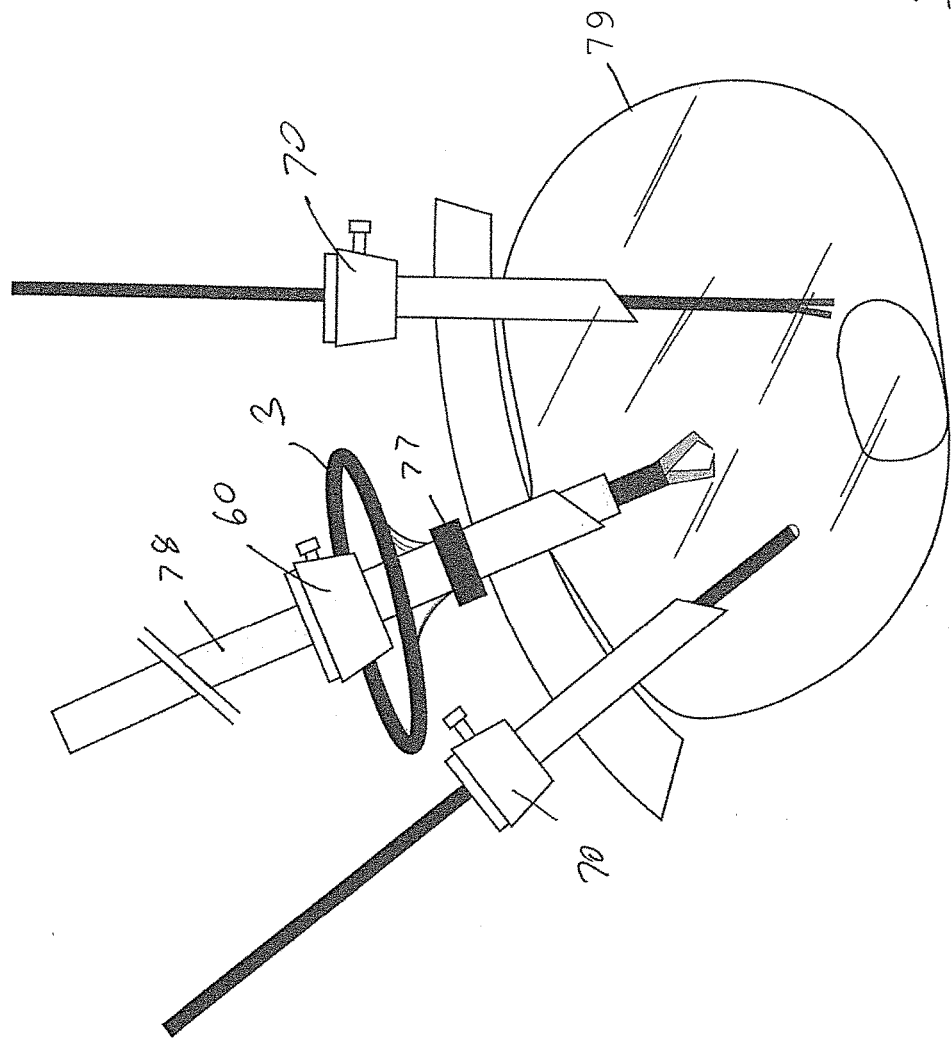

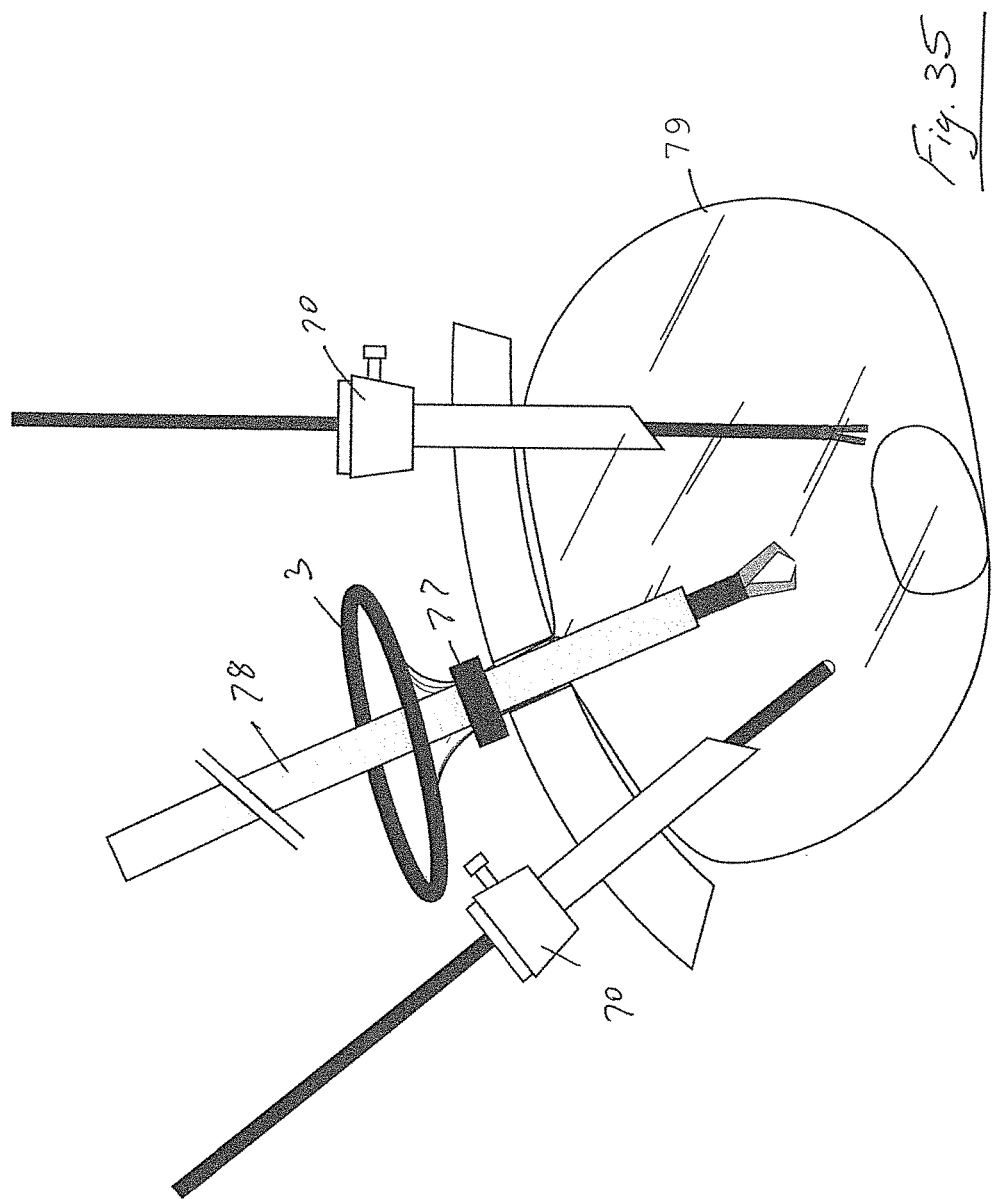

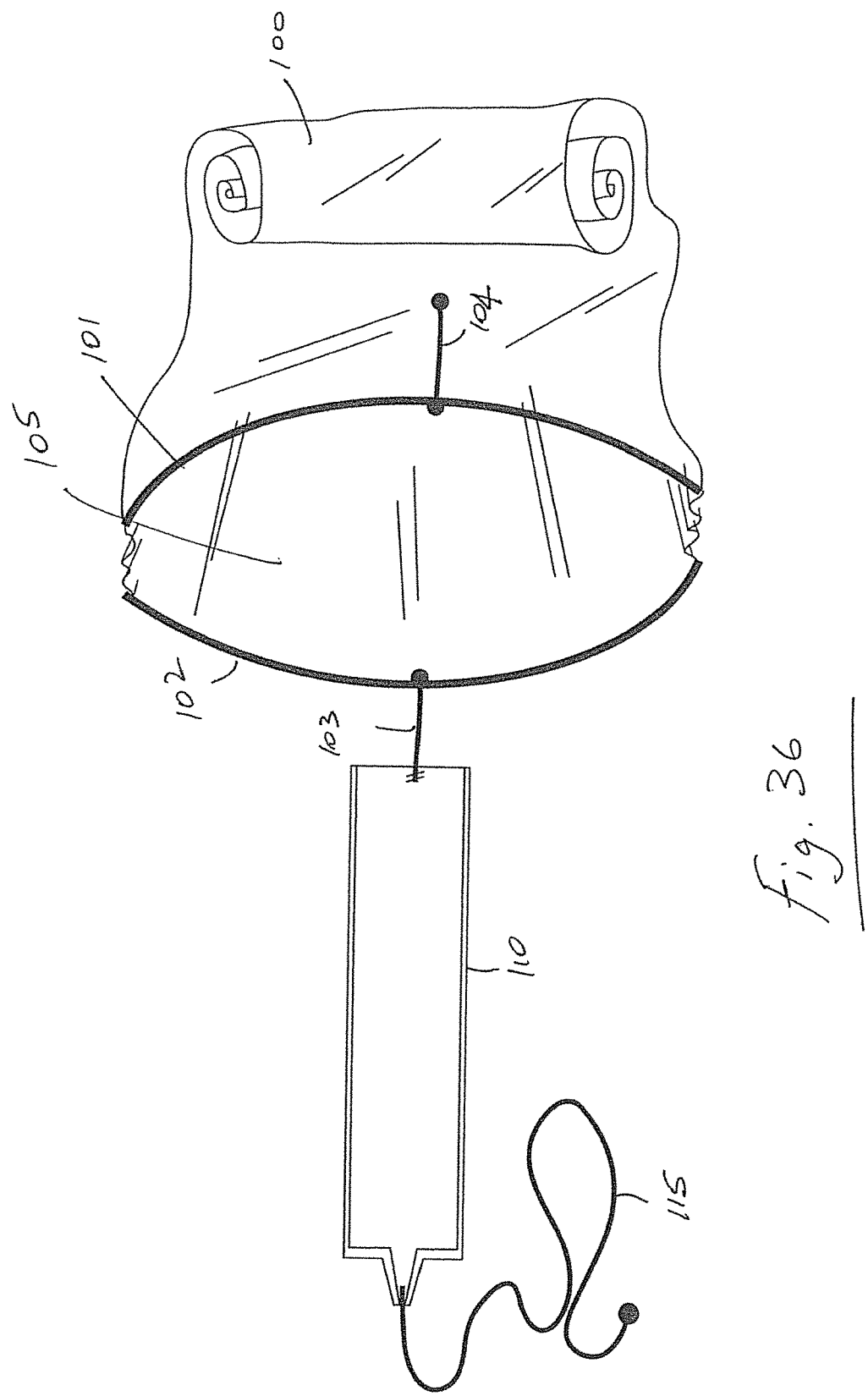

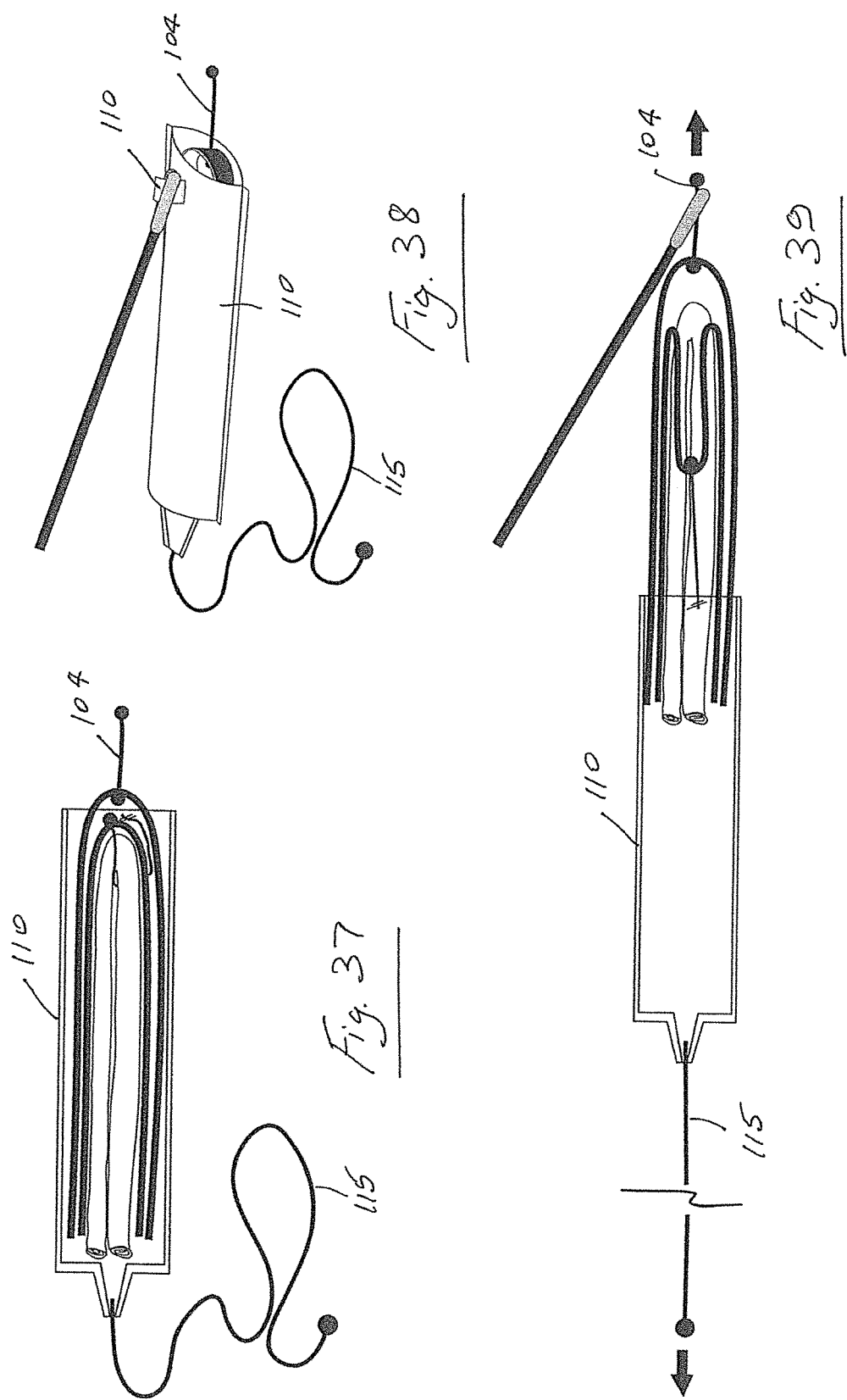

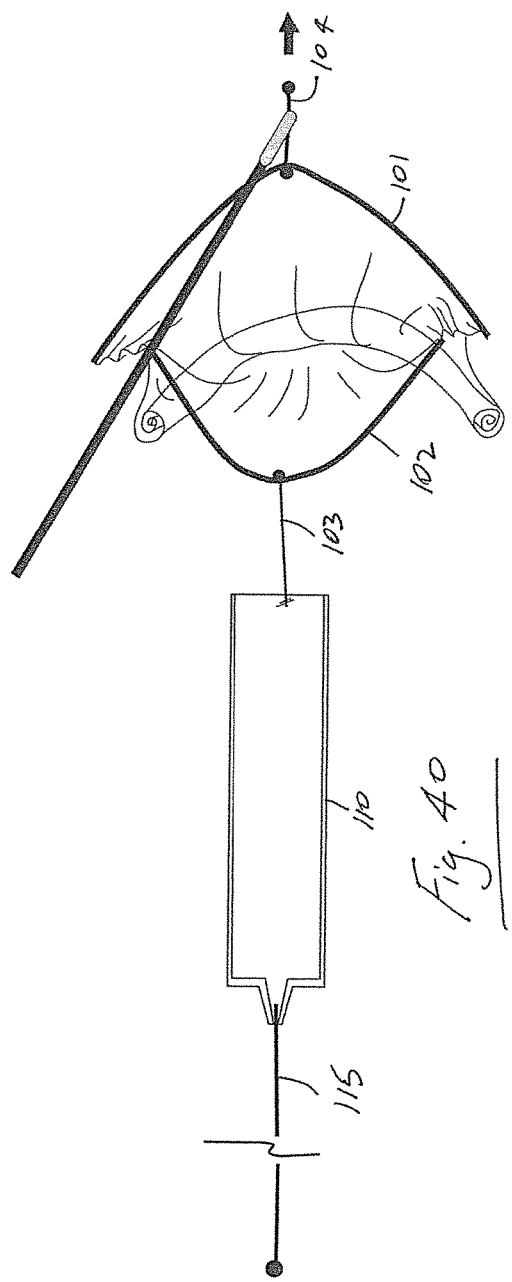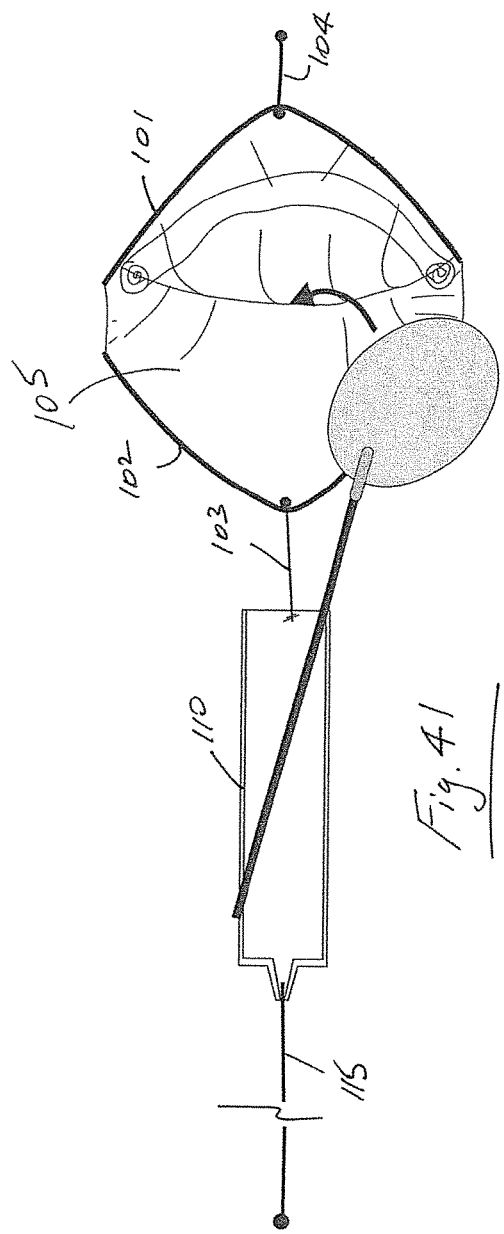

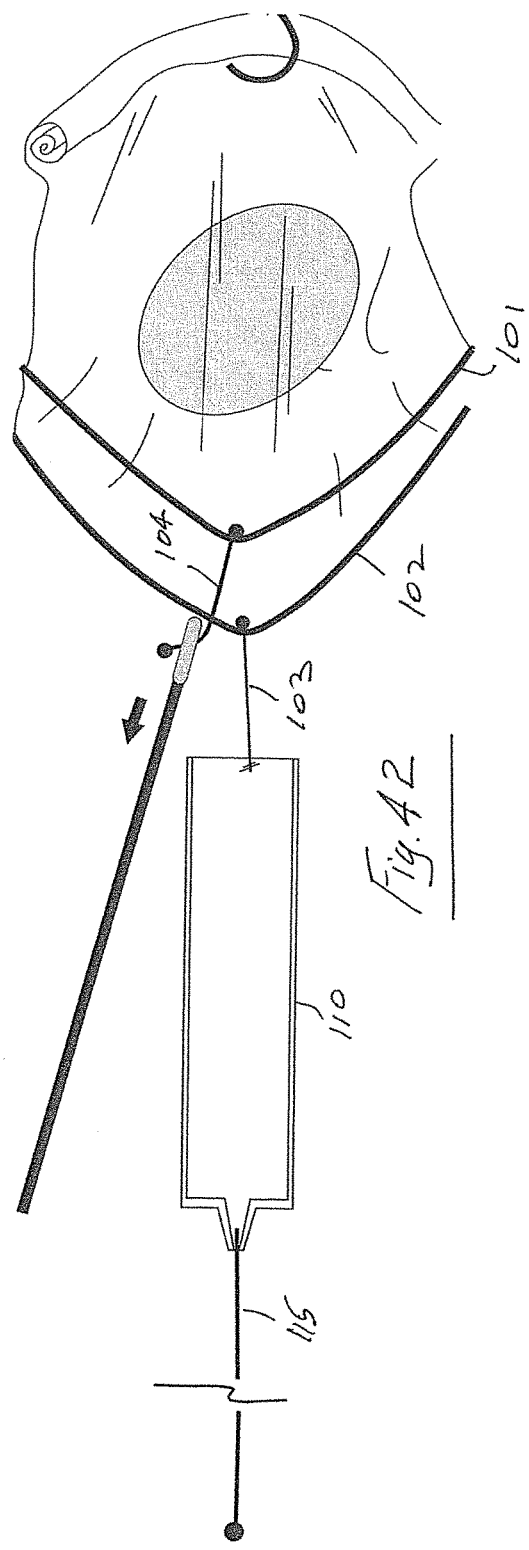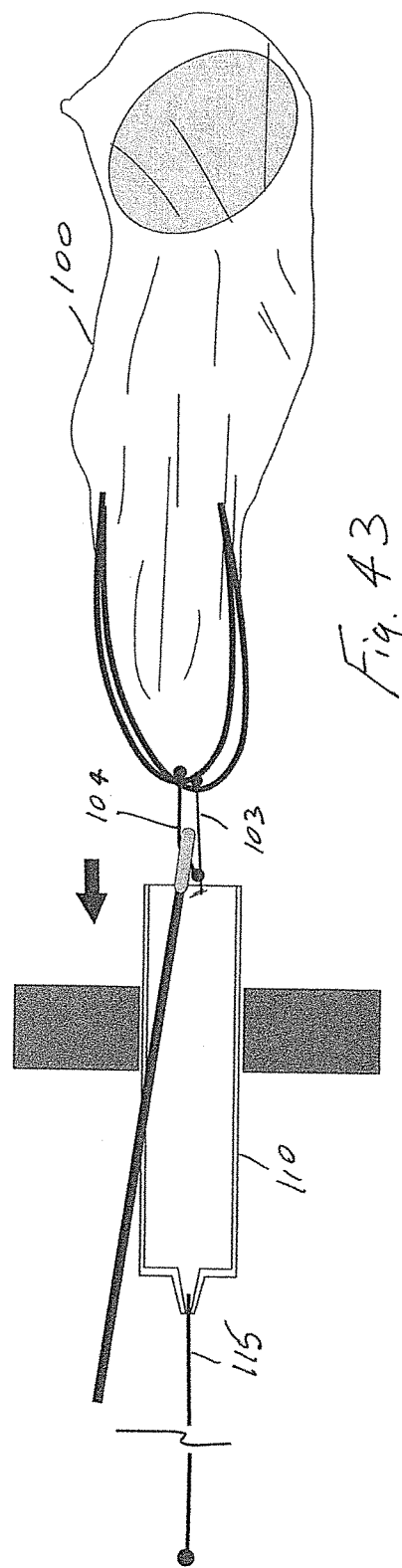

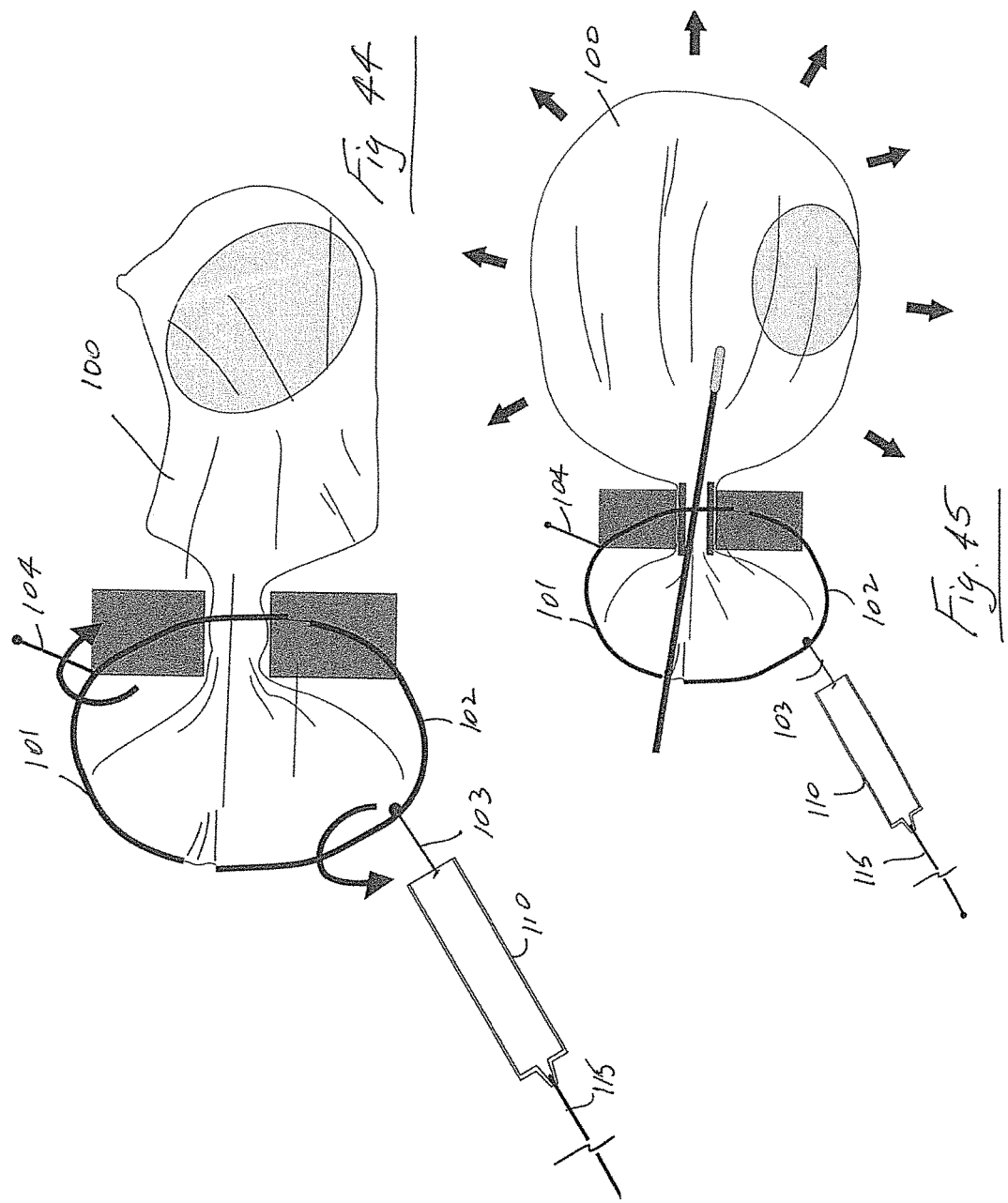

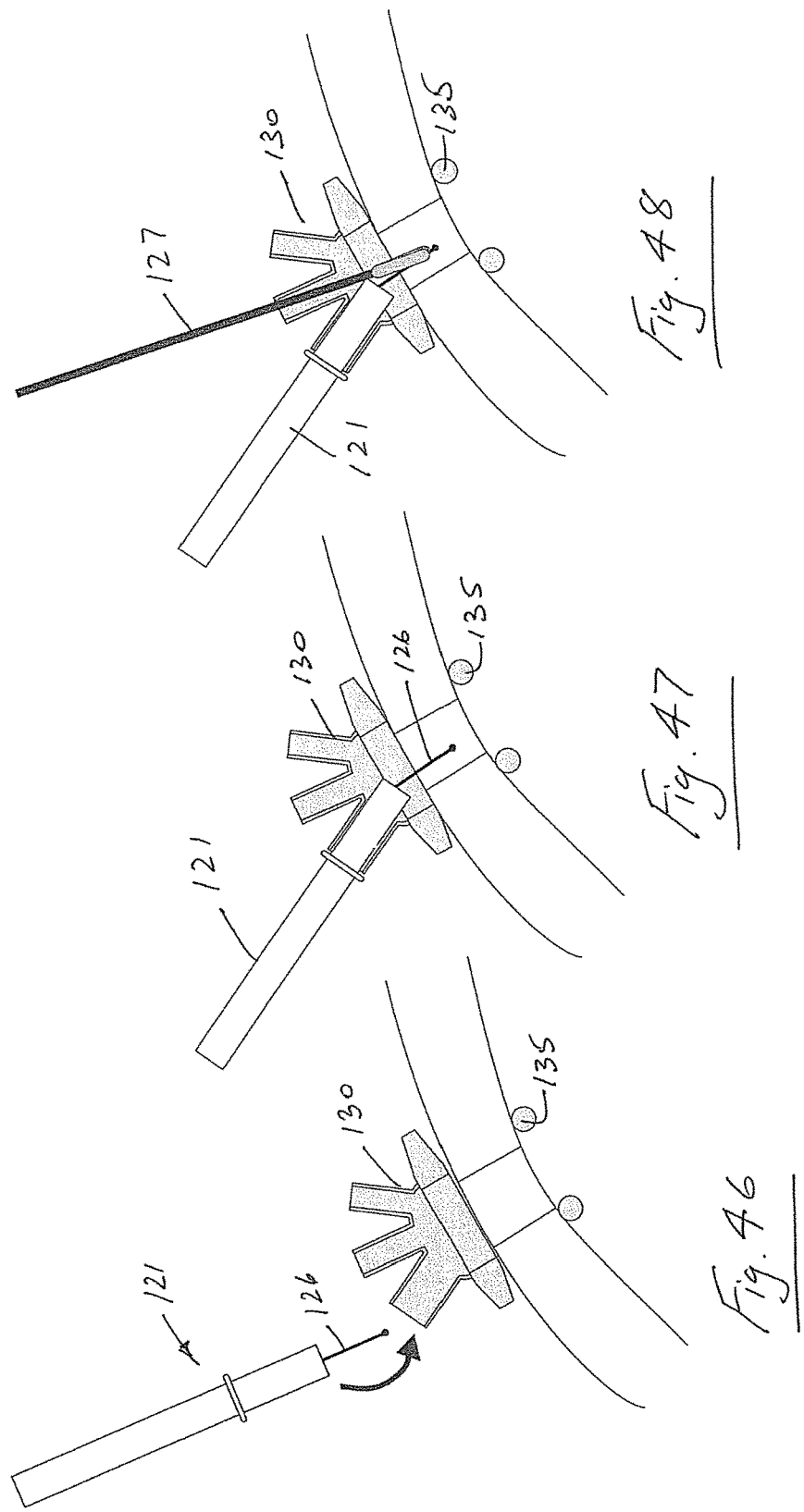

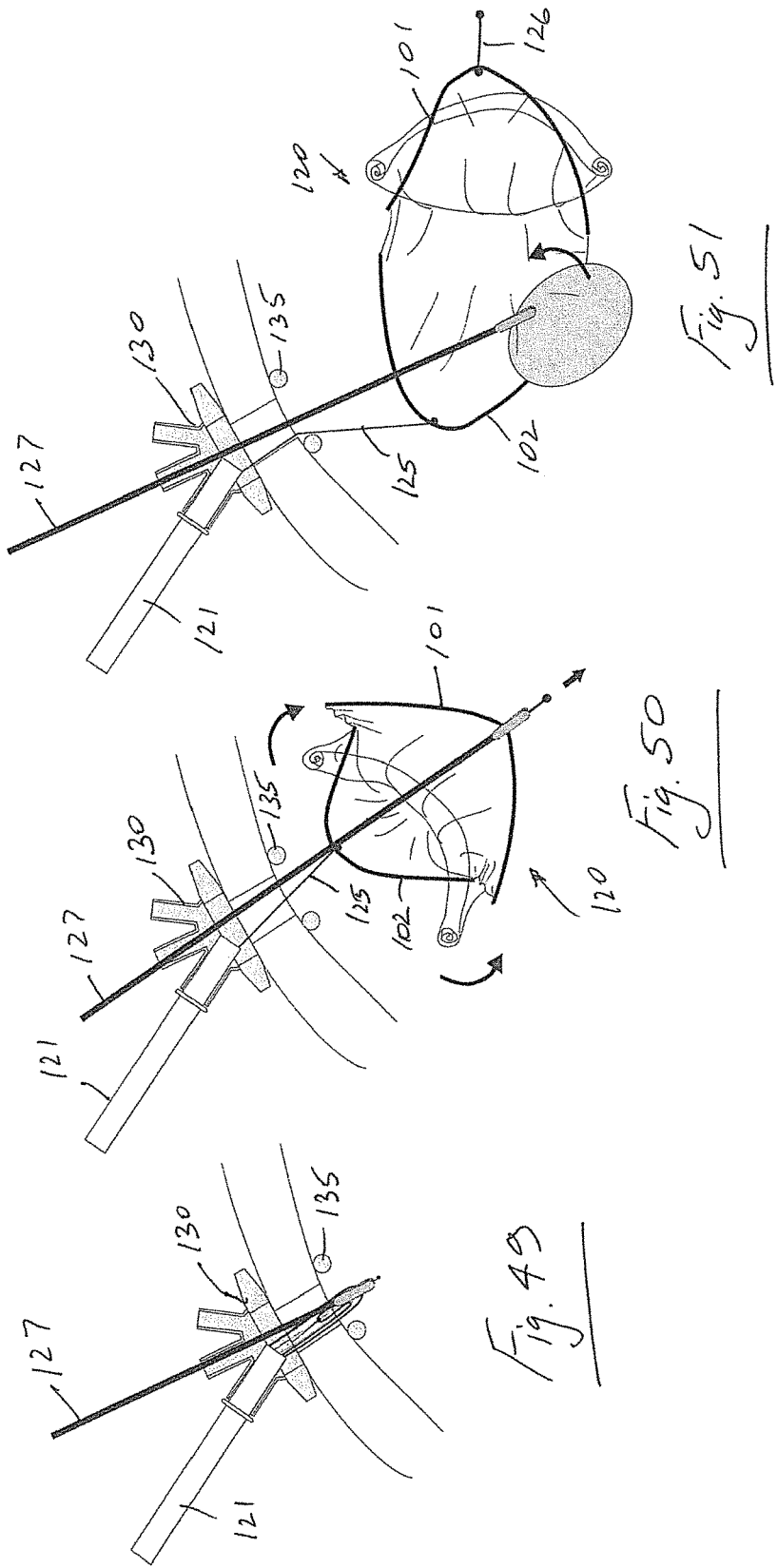

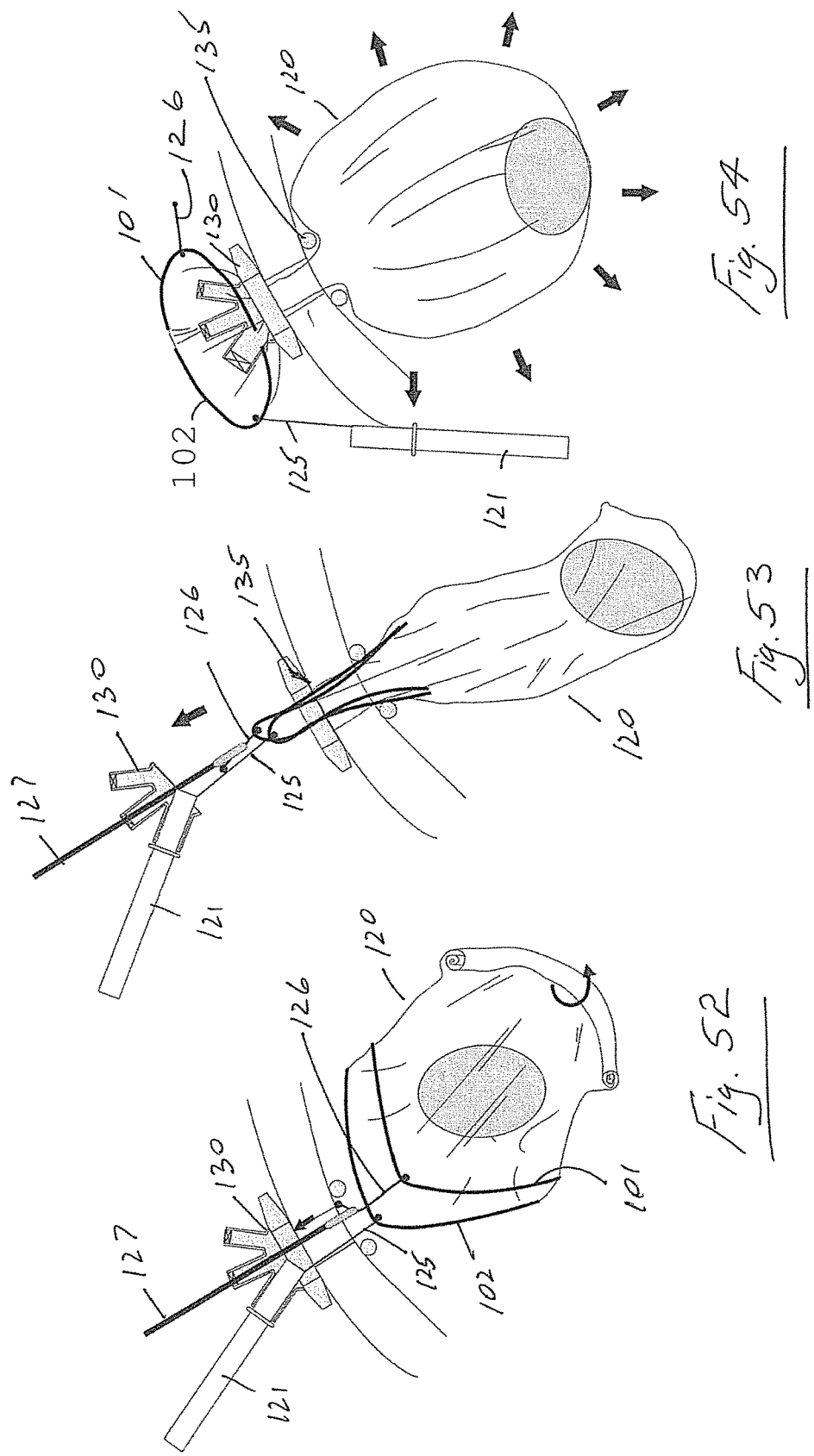

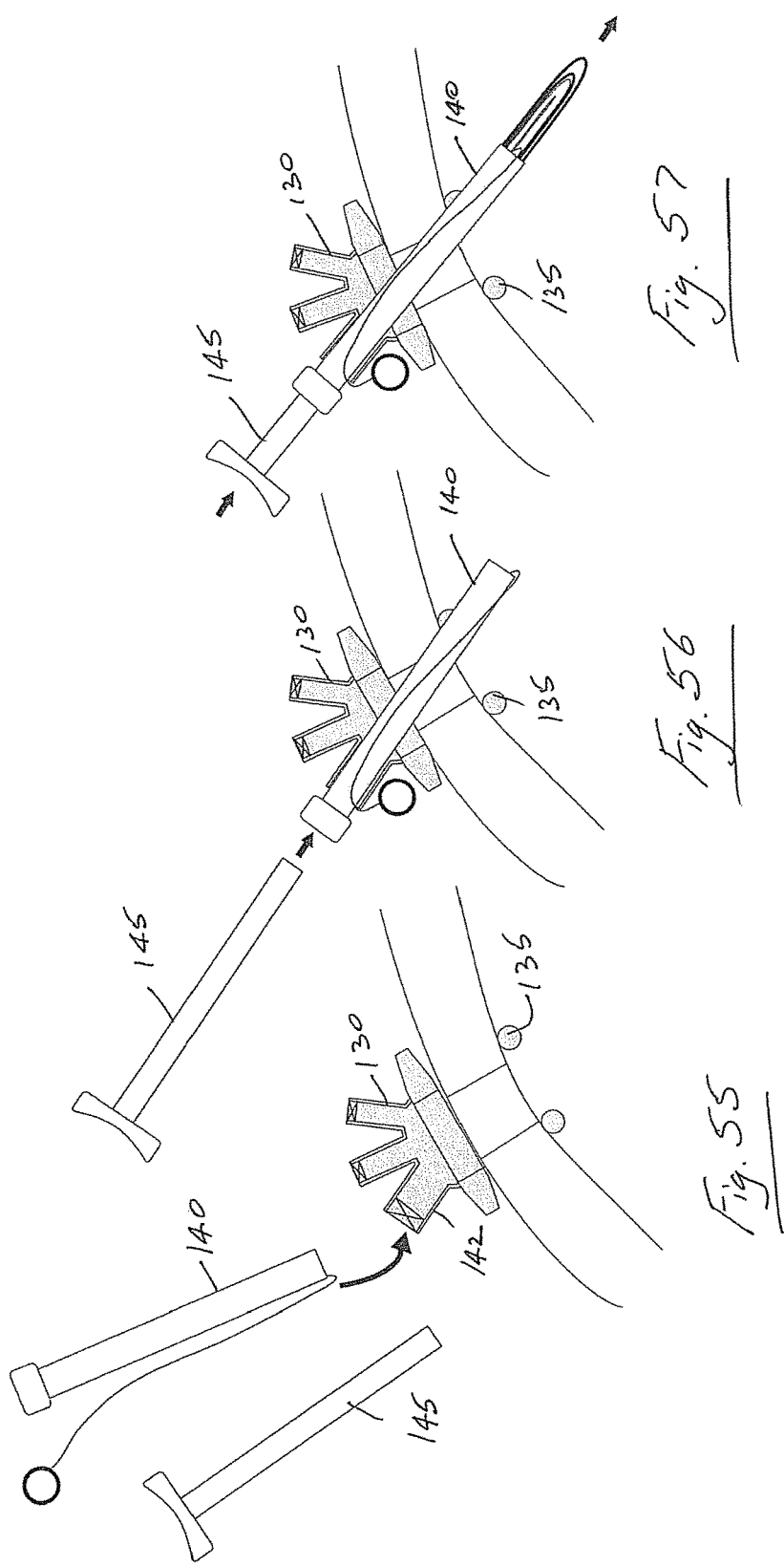

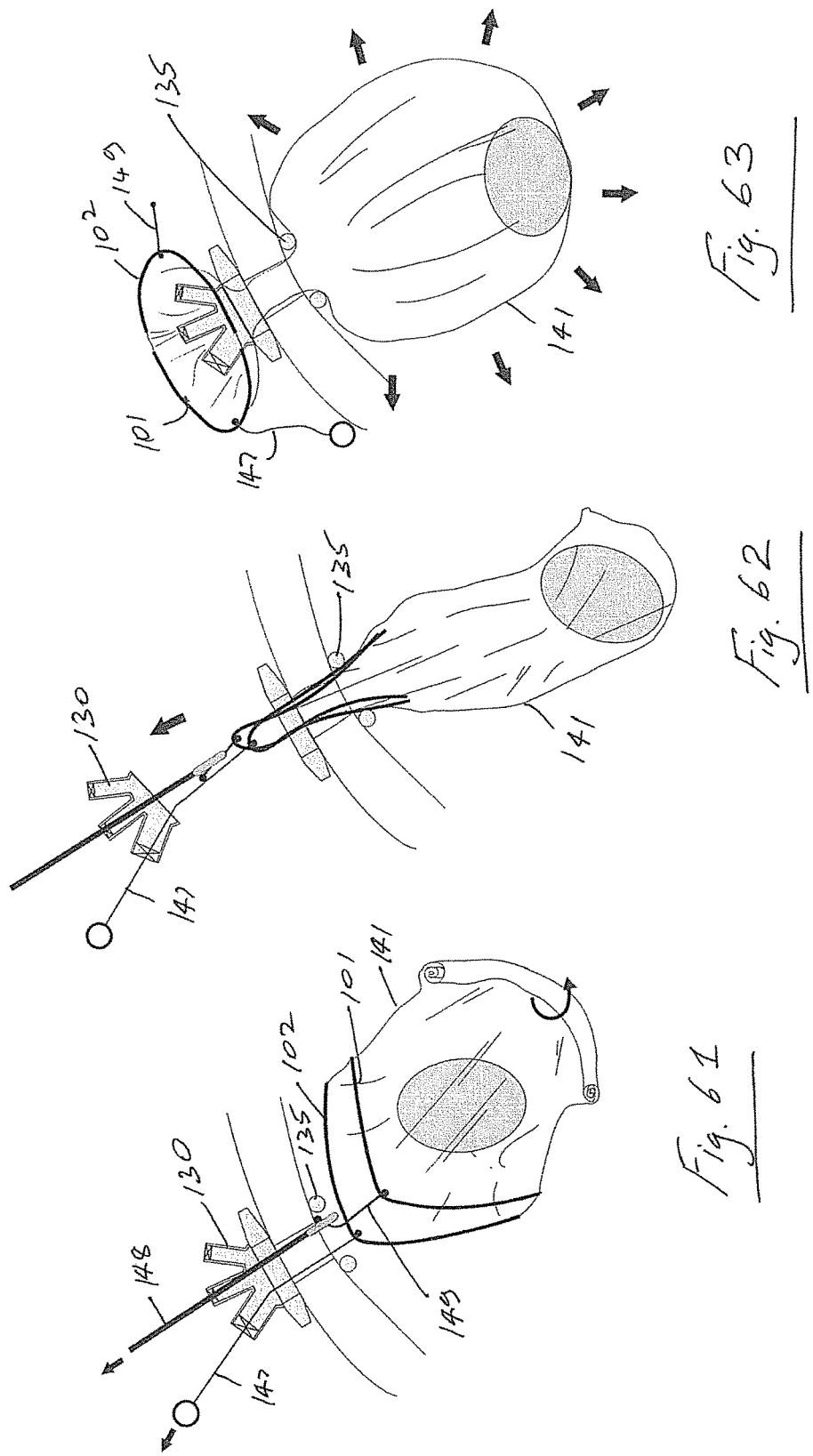

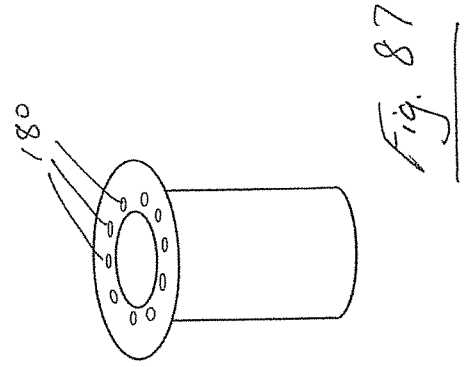
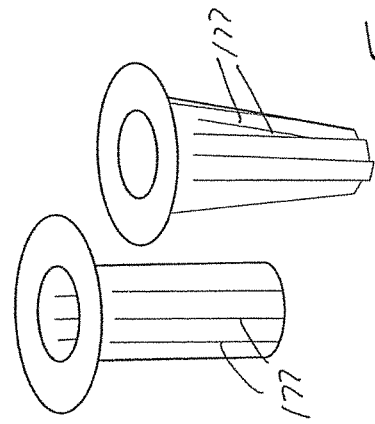
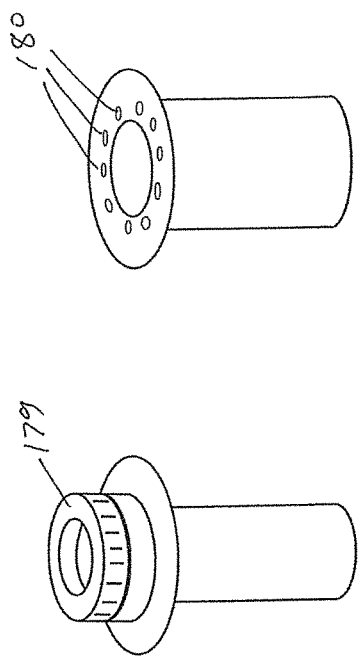
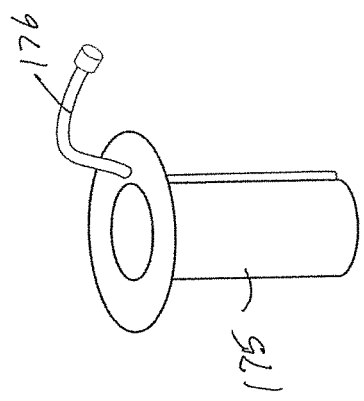
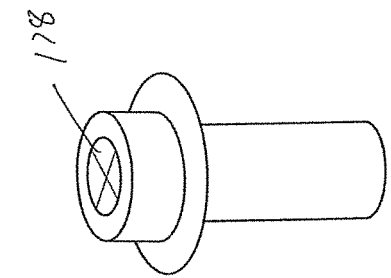

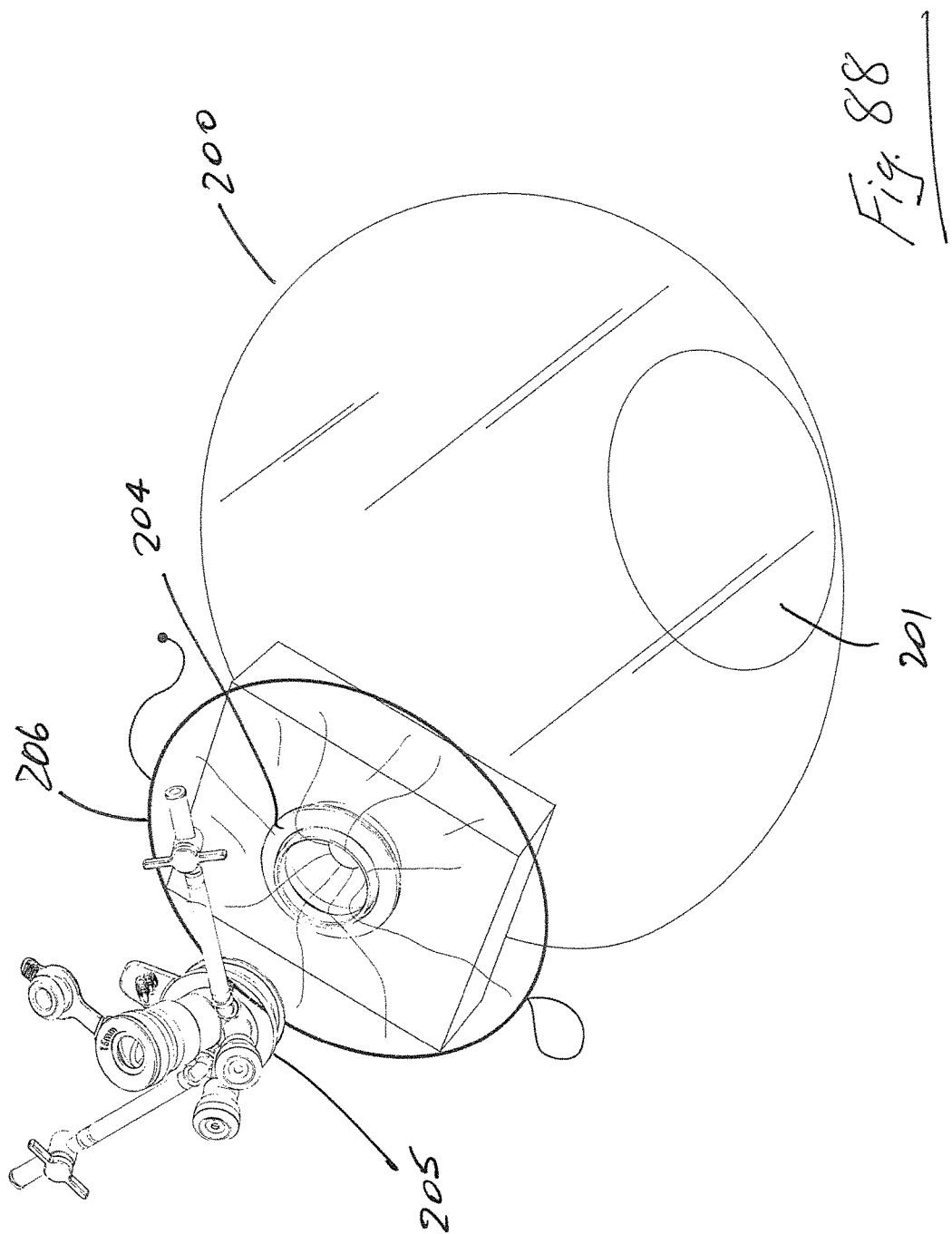

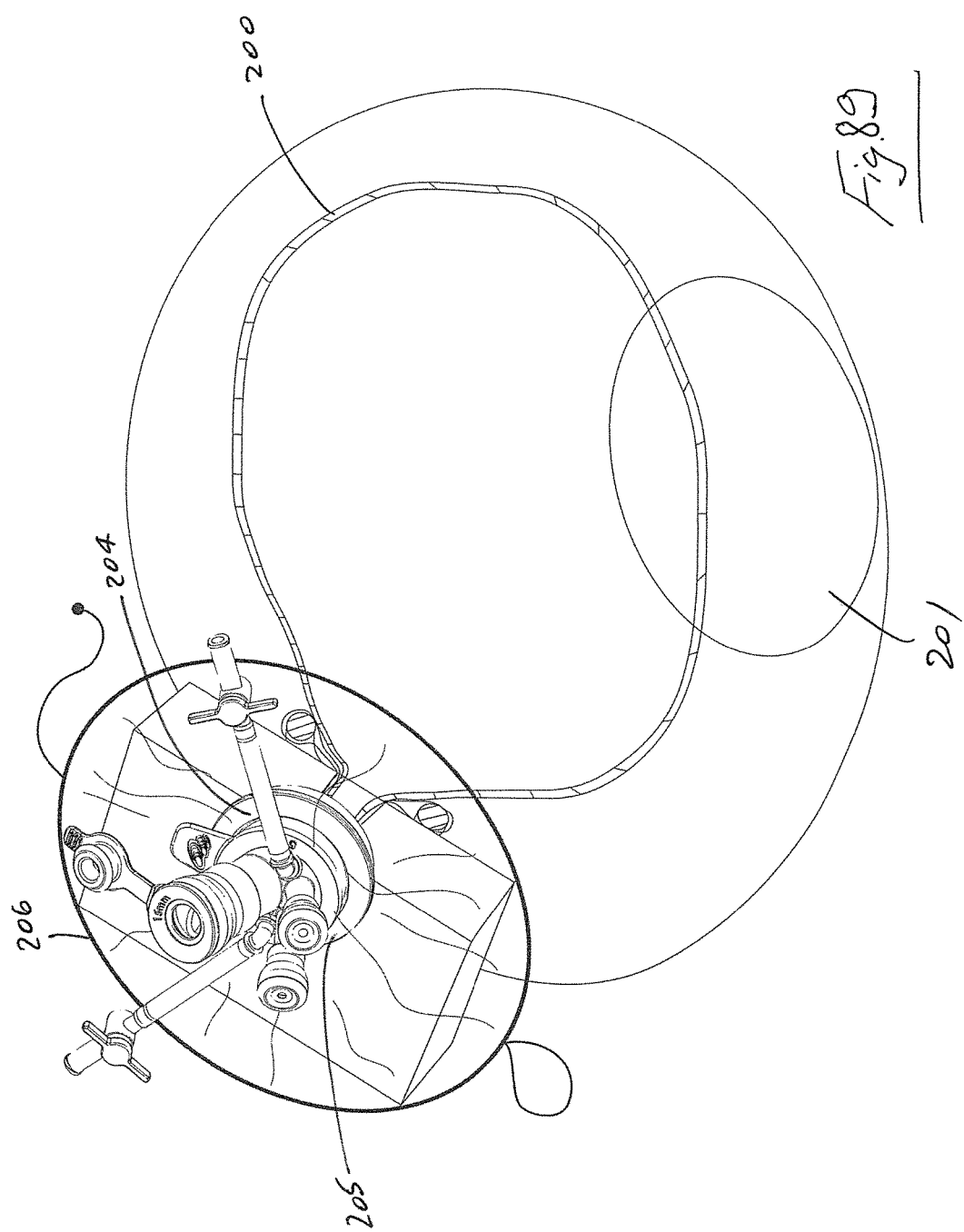

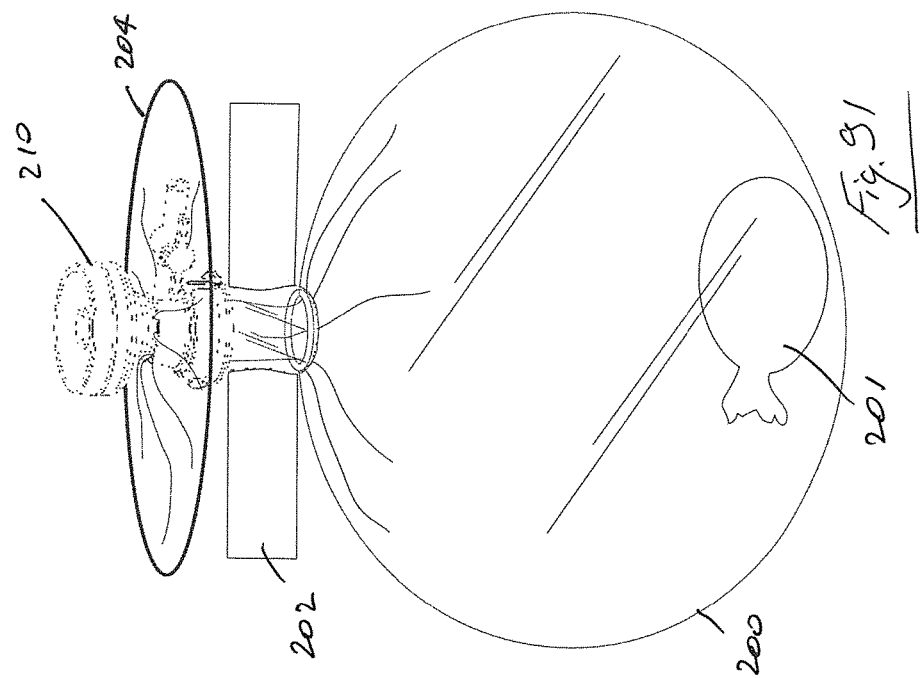
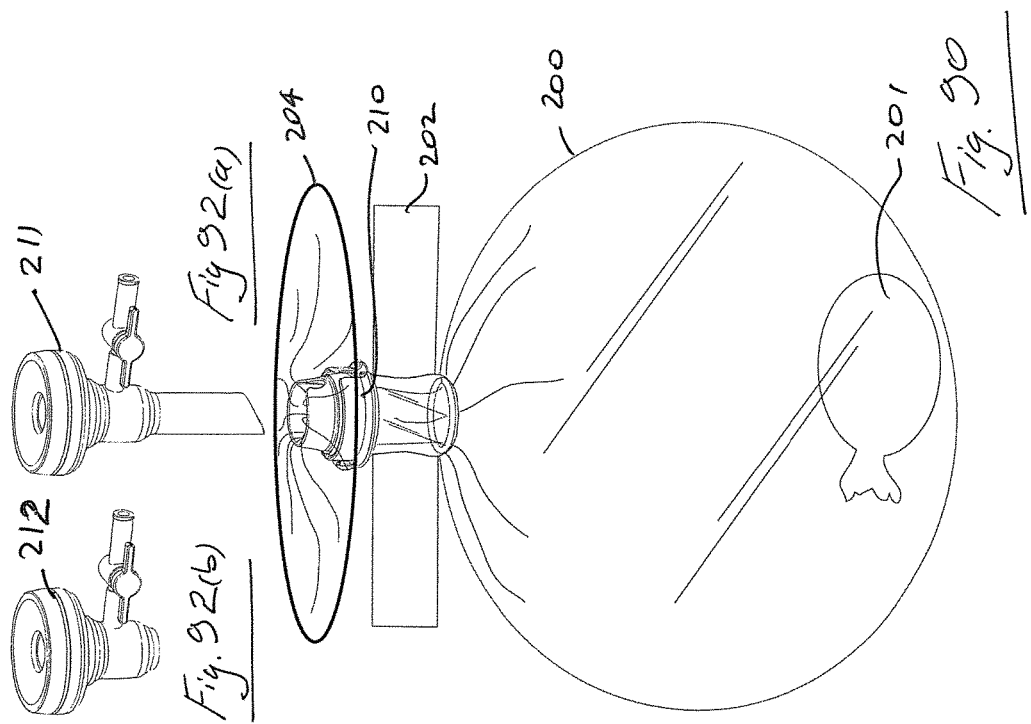

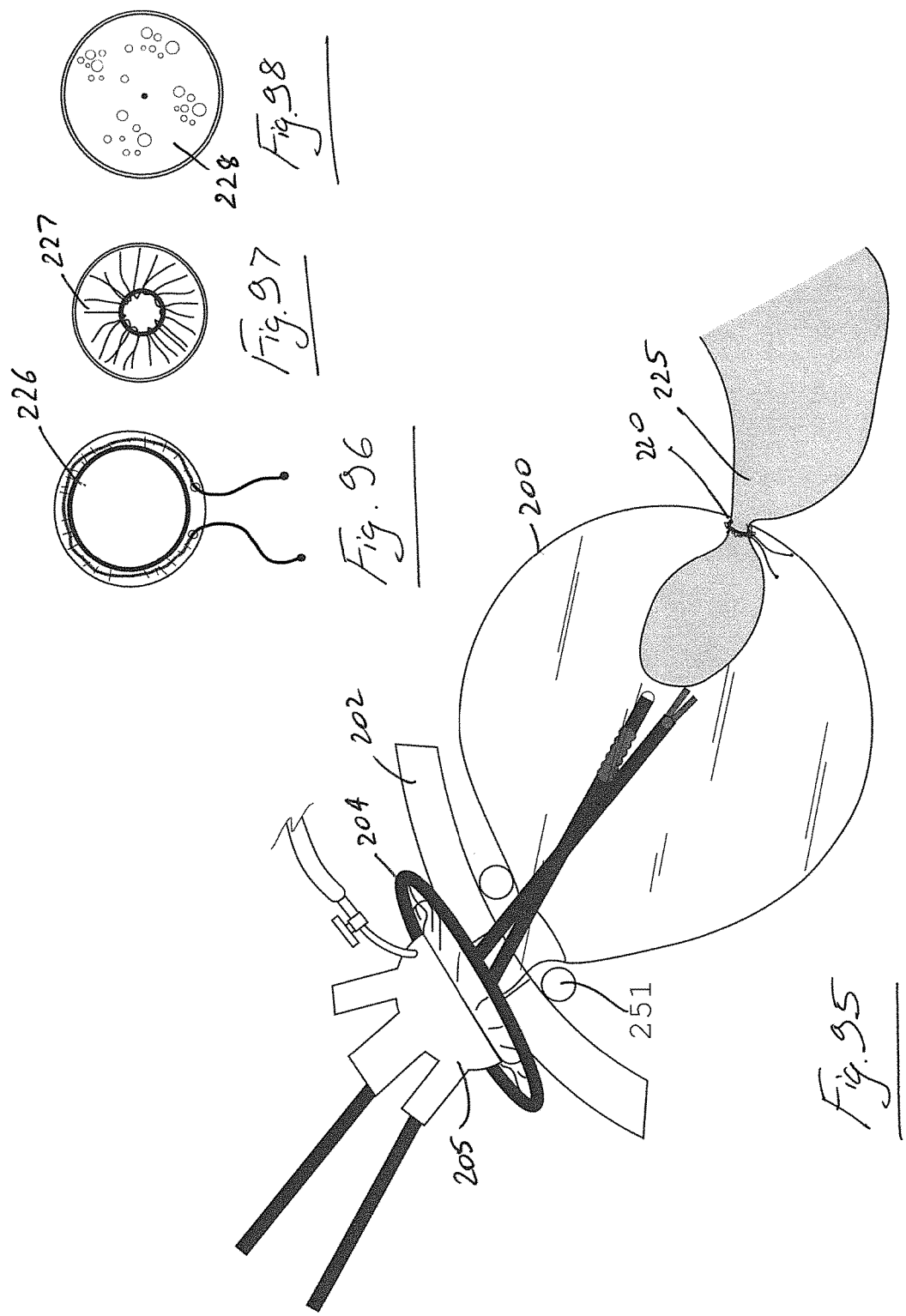

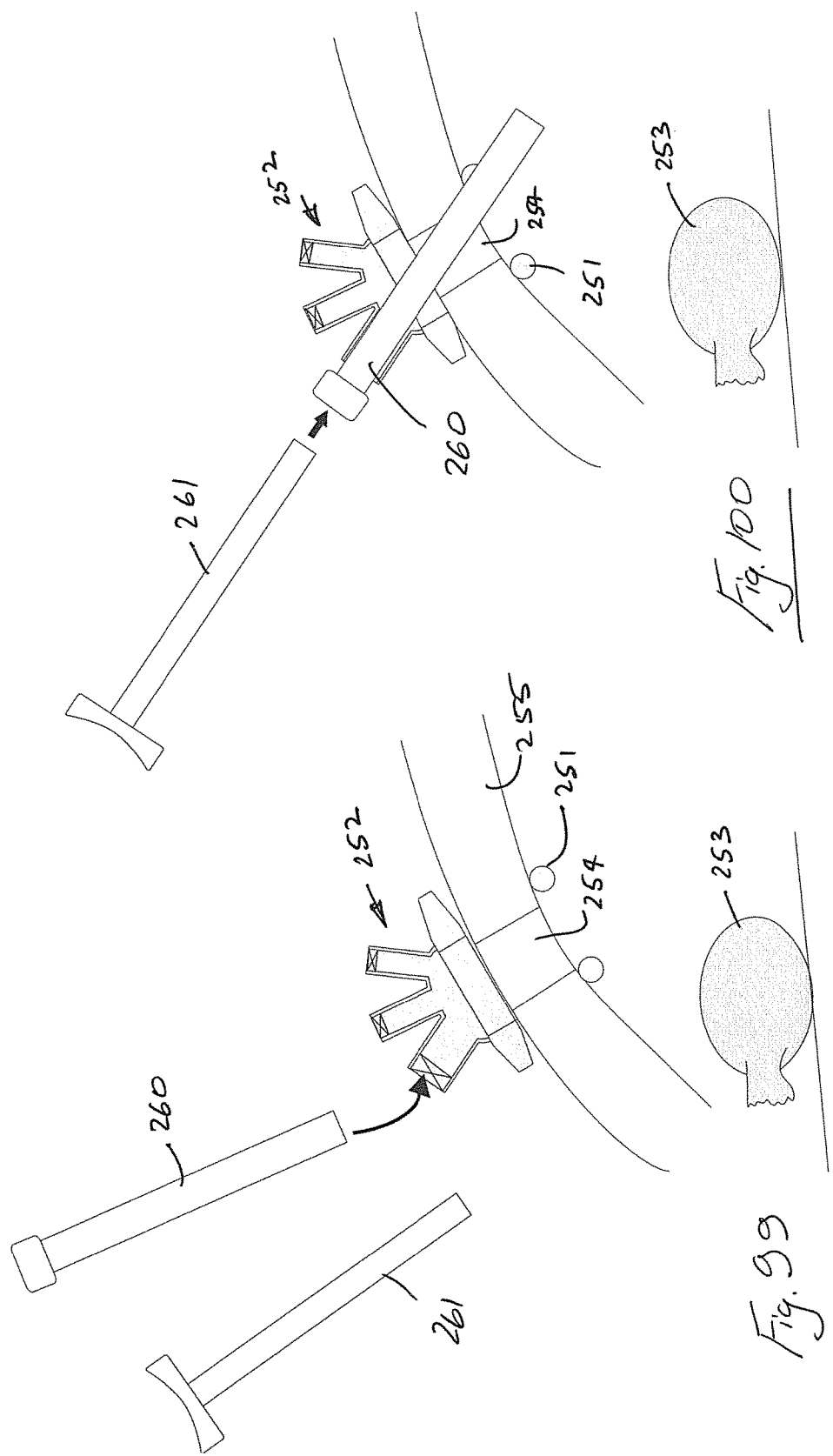

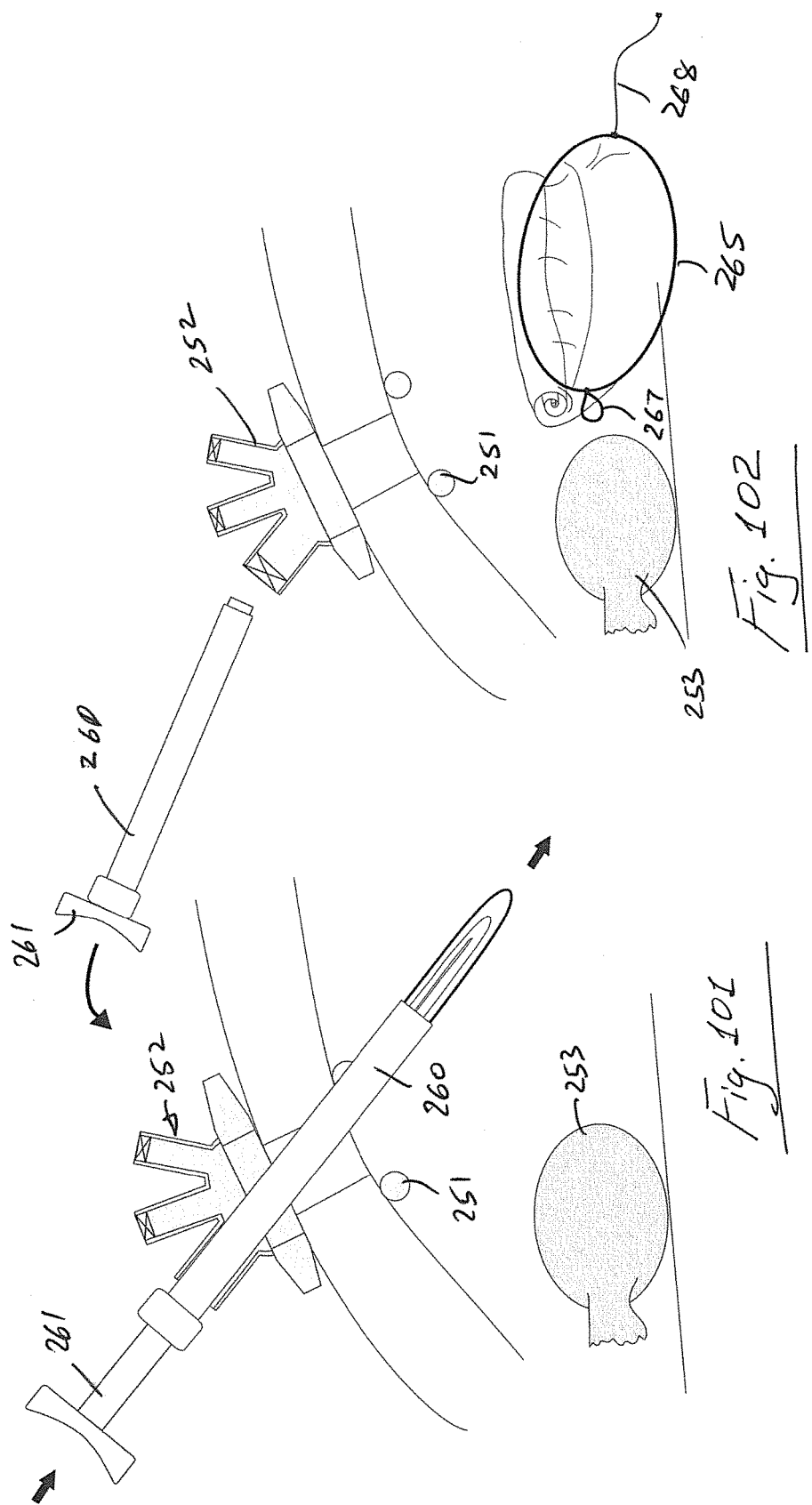

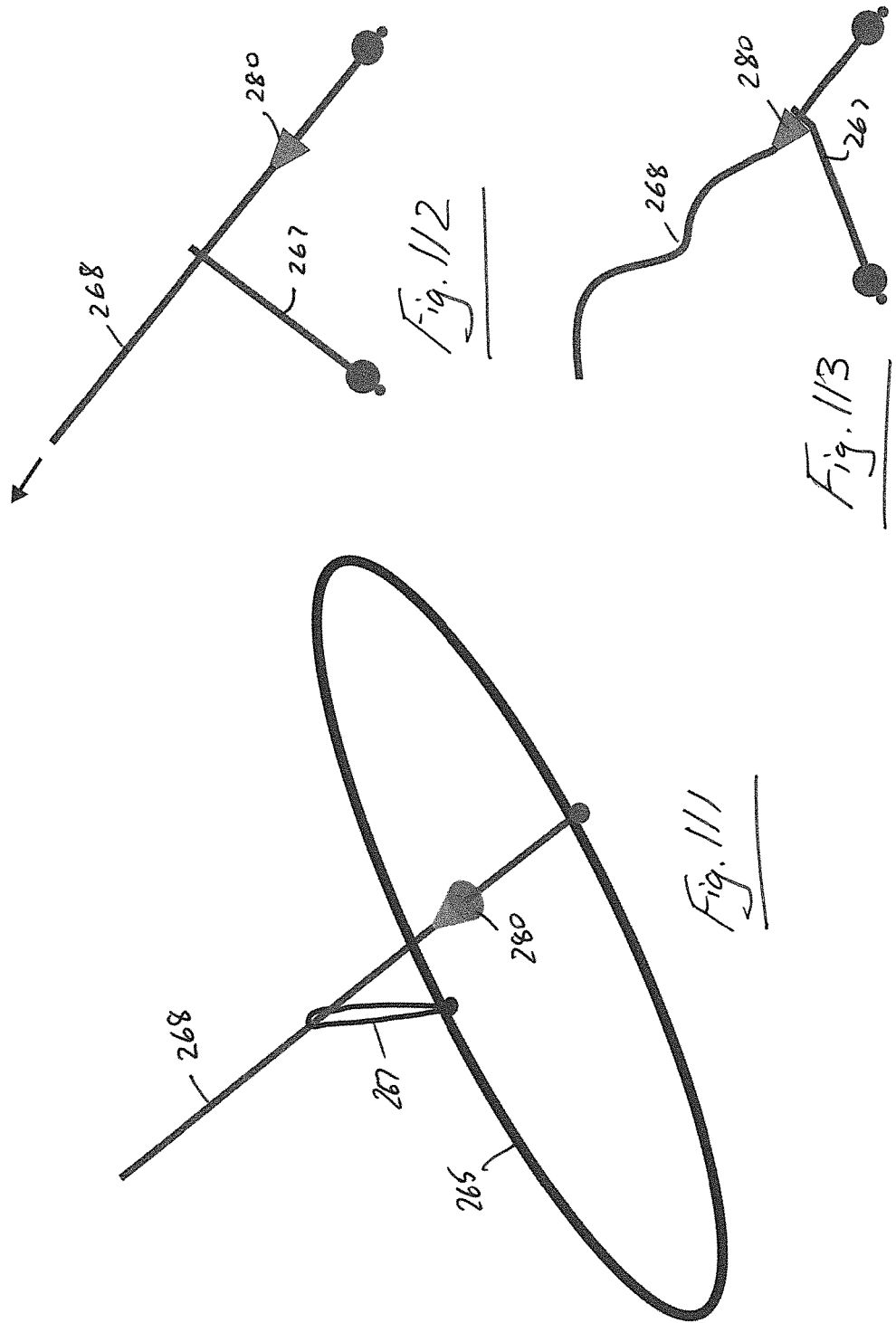

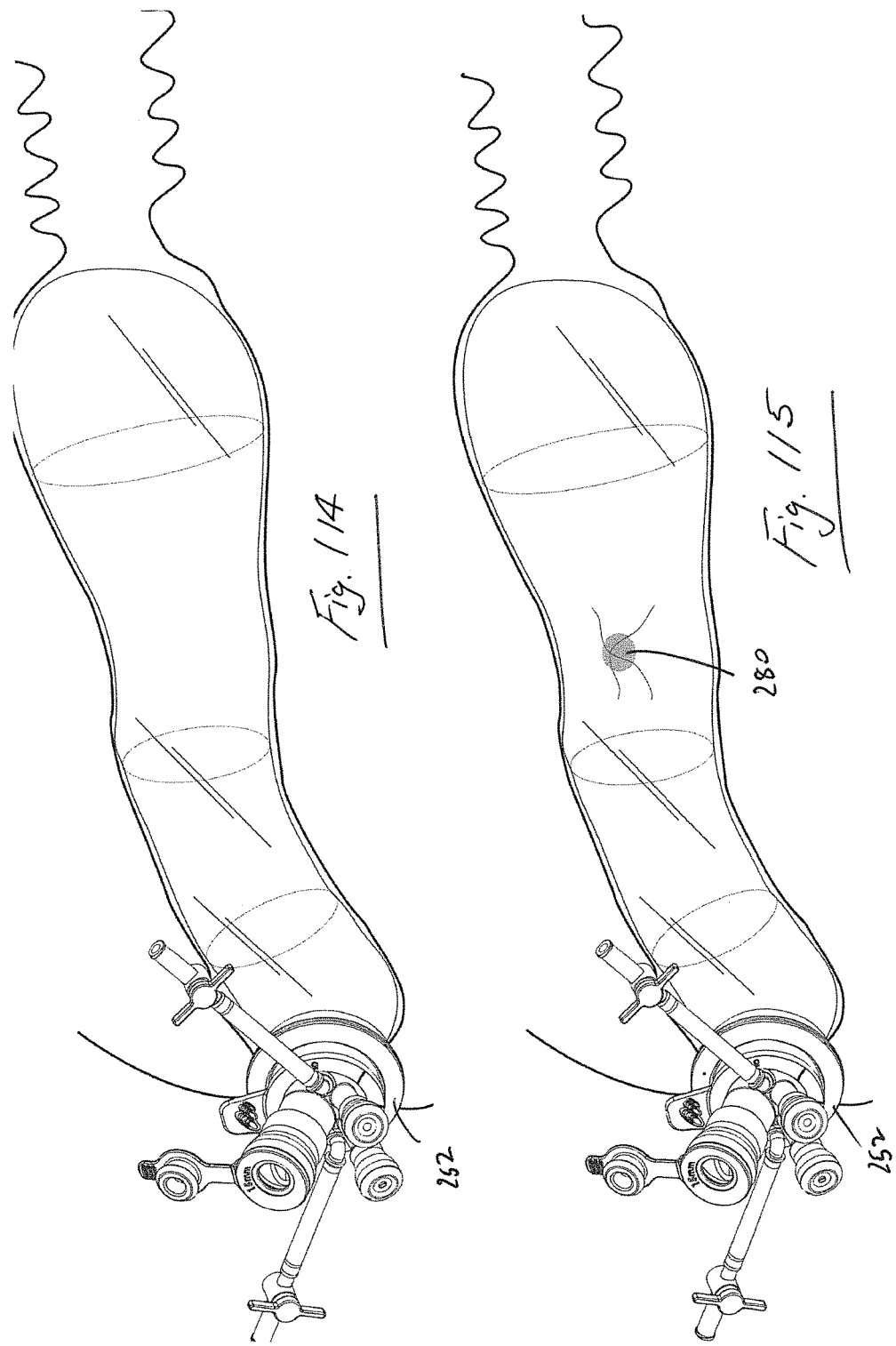

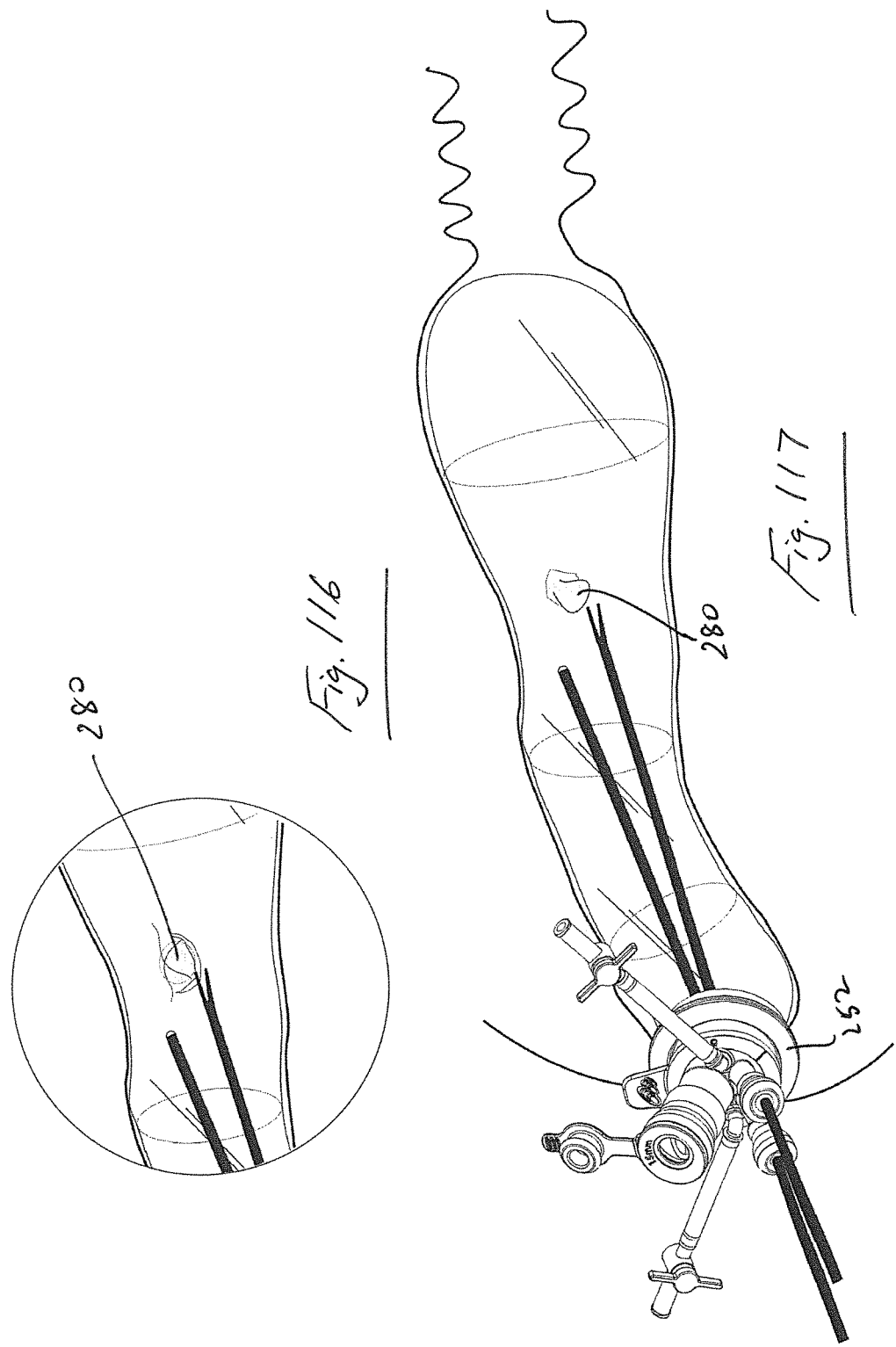

PNEUMOPERITONEUM DEVICE

CROSS-REFERENCE TO RELATED APPLICATIONS

This application is a continuation of U.S. application Ser. No. 13/725,148, filed on Dec. 21, 2012, which claims the benefit of U.S. Provisional Patent Application Ser. No. 61/580,088, filed on Dec. 23, 2011, and 61/742,125, filed on Aug. 3, 2012, the entire contents of which are incorporated herein by reference in their entireties.

INTRODUCTION

This invention relates to a pneumoperitoneum device. The invention also relates to a method of performing a surgical procedure.

STATEMENTS OF INVENTION

According to the invention there is provided an artificial pneumoperitoneum device for tissue isolation and/or extraction in a laparoscopic procedure.

In one aspect the invention provides an apparatus for use in laparoscopic surgery comprising an inflatable bag having an opening to receive tissue.

In one embodiment the bag comprises a ring element that extends around the opening. The ring element is preferably flexible to facilitate entry through an incision and/or an instrument access port.

In one case the ring element comprises an O-ring.

In one case the apparatus comprises a retainer for opening the bag.

The retainer may comprise at least one ring element which extends at least partially around the opening. The ring element may be flexible to facilitate entry through an incision and/or an instrument access port. In one case the ring element comprises an O-ring.

In one embodiment the retainer comprises ring parts.

There may be two separate ring parts.

In one embodiment the apparatus comprises a tether for each of the ring parts.

In one aspect the retainer has an insertion configuration and an expanded deployed configuration. The retainer may be biased into the deployed configuration.

In one case the bag is foldable for insertion.

The invention also provides an apparatus comprising a pouch for containing the bag in an insertion configuration. The pouch may be at least partially insertable through an opening and/or an incision and/or an access port.

In one case the apparatus comprises an activator for delivering the bag from the pouch, on insertion. The activator may comprise a tab. In one case the activator comprises a plunger.

In one embodiment the apparatus comprises a user tether attached to the bag.

In one case the bag comprises a neck region. The neck region may be adjacent to the retainer.

In one embodiment the bag itself comprises a port. The port may be an exit port and/or an entrance port. The bag may comprise a plurality of ports.

In some embodiments the port comprises a valve. The valve may comprise a choke valve or a cuff valve. In one case the valve comprises an elastomeric material such as a gel.

In some embodiments the apparatus comprises a proximal tether and a distal tether. The distal tether may be movable relative to the proximal tether.

In one case the proximal tether comprises a loop through which the distal tether is movable.

There may be a lock to restrict movement of the distal tether. In one case the lock is provided by or on the proximal tether and/or the distal tether. The lock may comprises a projection on the distal tether which is engagable by the proximal tether.

In one embodiment the apparatus further comprises an access port to which the bag is mounted or mountable. The access port may comprise a retractor having a distal anchoring element for location within a wound interior, a proximal member for location externally of a wound opening and a retractor member extending proximally from the distal anchoring element to retract laterally the sides of an incision.

The bag may be mountable to the proximal member of the retractor.

In one embodiment the apparatus further comprises a cap for closing the proximal side of the retractor. The cap may comprise an access device for an instrument or a surgeons hand/arm. The access device may be mountable to the proximal member of the retractor.

The invention also provides apparatus for use in laparoscopic surgery comprising a bag of the invention and a retractor. The apparatus may further comprise an access port.

The invention also provides a viscera retainer comprising an apparatus of the invention.

In another aspect the invention provides a method for performing a laparoscopic procedure comprising the steps of:—
 inserting a bag through an opening;
 inflating the bag;
 delivering tissue into the bag before or after inflating the bag; and
 carrying out a procedure on the tissue located in the inflated bag.

In one embodiment the opening is an opening into a body cavity.

The opening may be provided, at least in part, by an incision.

The method may comprise providing a retractor in the opening and inserting the bag through the retracted opening.

The tissue may be delivered into the bag before inflating the bag.

The method may comprise the step, either before or after delivery of the tissue into the bag, of mounting the bag to the retractor.

In one embodiment the method comprises passing an instrument into the inflated bag to carry out a procedure.

The method may comprise the steps of providing an access port in the bag and passing an instrument and/or tissue through the access port.

In one embodiment the method comprises sealing the access port prior to and/or subsequent to passage of an instrument and/or tissue through the access port.

The device of the invention comprises at least one instrument seal to effect a seal around at least one instrument extended through the device, the instrument seal being configured to be arranged in sealing relationship to a body of a patient. The device preferably has a distal anchoring member for location within a wound interior. The device preferably also has a retractor member extending proximally from the distal anchoring member to retract laterally the sides of a wound opening. Preferably the device comprises a first instrument seal to effect a seal around a first instrument extended through the device, and a second instrument seal to effect a seal around a second instrument extended through the device. By providing the two seal arrangement, this ensures that insertion or manipulation or removal of the second instrument does not adversely effect the seal around the first instrument. The device may comprise a third instrument seal to effect a seal around a third instrument extended through the device. The first instrument seal may be spaced apart from the second instrument seal. The first instrument seal may be formed separately from the second instrument seal. The first instrument seal may have a larger radial dimension than the second instrument seal. The instrument seal may be a valve. Alternatively, the seal is of a gelatinous elastomeric material.

In one case the device comprises a proximal member for location externally of a wound opening. The retractor member may extend at least between the distal anchoring member and the proximal member. The retractor member may extend in two layers between the distal anchoring member and the proximal member. A first end portion of the retractor member may be fixed to the proximal member. The retractor member may be movable relative to the distal anchoring member. A second end portion of the retractor member may be movable relative to the proximal member. The retractor member may extend distally from the proximal member to the distal anchoring member, may be looped around the distal anchoring member, and may extend proximally from the distal anchoring member to the proximal member. The proximal member may comprise an inner part and an outer part. The retractor member may extend between the inner part and the outer part.

In another embodiment the instrument seal is spaced proximally of the proximal member. The device may comprise at least one connector member to connect the proximal member to the at least one instrument seal. The connector member facilitates a degree of lateral movement of the instrument while maintaining the seal. The connector member may comprise a sleeve. The connector member may be of a laterally flexible material. The connector member may be of a longitudinally rigid material. The connector member may be of a rubber-like material. The connector member may be of a longitudinally flexible material.

In another case the instrument seal is mounted to the connector member. The instrument seal may be releasably mounted to the connector member. The instrument seal may comprise a mounting part to mount the instrument seal to the connector member. The mounting part may be of a rigid material. The instrument seal may comprise a sealing part to effect a seal around an instrument extended through the device, the sealing part being overmoulded over at least part of the mounting part.

BRIEF DESCRIPTION OF THE DRAWINGS

The invention will be more clearly understood from the following description of some embodiments thereof, given by way of example only, with reference to the accompanying drawings, in which:—

FIGS. 3 to 5 are views of another pneumoperitoneum device according to the invention;

FIGS. 6 to 18 are diagrams illustrating the use of the device of FIGS. 1 to 5;

FIGS. 19 to 22 are diagrams illustrating another use of the device of FIGS. 1 to 5;

FIGS. 25 to 30 are diagrams illustrating various ways in which a device according to the invention may be introduced;

FIGS. 31 to 35 are diagrams illustrating the device, in use;

FIG. 36 is a diagram of another device according to the invention;

FIGS. 37 to 45 are diagrams illustrating the device of FIG. 36, in use;

FIG. 46 is a diagram of another device according to the invention;

FIGS. 47 to 54 are diagrams illustrating the device of FIG. 46, in use;

FIG. 55 is a diagram of a further device according to the invention;

FIGS. 56 to 63 are diagrams illustrating the device of FIG. 55, in use;

FIGS. 65 to 74 are diagrams illustrating the device of FIG. 64, in use;

FIGS. 82 to 87 are isometric views of alternative grommets;

FIG. 88 is an isometric view of another device according to the invention with a multi-lumen access port removed;

FIG. 89 is an isometric, partially cut-away view of the device of FIG. 88 with an access port in position for use;

FIG. 90 is an isometric view of a device according to the invention.

FIG. 91 is another view of the device of FIG. 90 with an access port in position for use;

FIGS. 92(a) and 92(b) are isometric views of single lumen access ports for use with the devices of the invention;

FIG. 95 is an isometric view illustrating devices of the types of FIGS. 93 and 94, in use;

FIGS. 96 to 98 are views of various seals that may be used in association with the device;

FIGS. 99 to 110 illustrate one method of use of devices according to the invention;

FIGS. 111 to 113 are views illustrating a locking detail of the device of FIGS. 99 to 110;

FIGS. 114 to 117 are views of a device according to the invention, in use in the colon;

DETAILED DESCRIPTION

The invention provides an artificial pneumoperitoneum device for tissue isolation and/or extraction in a laparoscopic procedure The device is used to safely reduce and remove resected tissue from within the abdomen via small laparoscopic incisions. The bag creates an artificial pneumoperitoneum containing the specimen and eliminating the dissemination of tissue and cellular fluids within the peritoneal cavity. The device facilitates effective and safe isolation of tissue/organs within an artificial pneumoperitoneum for improved surgical procedures and subsequent safe tissue extraction.

A tissue bag is inserted within the peritoneal cavity through an incision in the abdominal wall or vagina.

In one case the bag with one or more openings is placed within the abdomen. Excised tissue is placed within the opening of a deflated bag. One or more openings of the bag are withdrawn outside the abdomen and the bag is inflated. Instruments including laparoscopic visualization are placed within the inflated bag that remains within the peritoneal cavity. The tissue retained within the bag is morcellated/crushed/reduced and removed. The bag is deflated and removed with residual tissue/blood/fluids inside. A major advantage is that the tissue to be removed is retained in the bag which prevents potentially harmful material such as cancerous cells from being released in the body cavity.

Figure 1:
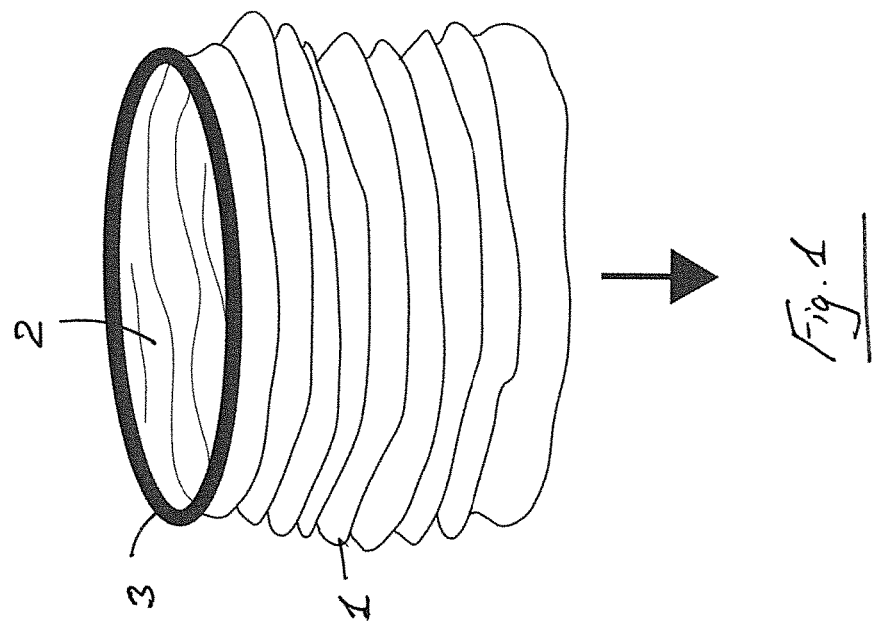
FIG. 1 is an isometric view of a pneumoperitoneum device according to the invention.
Figure 2:
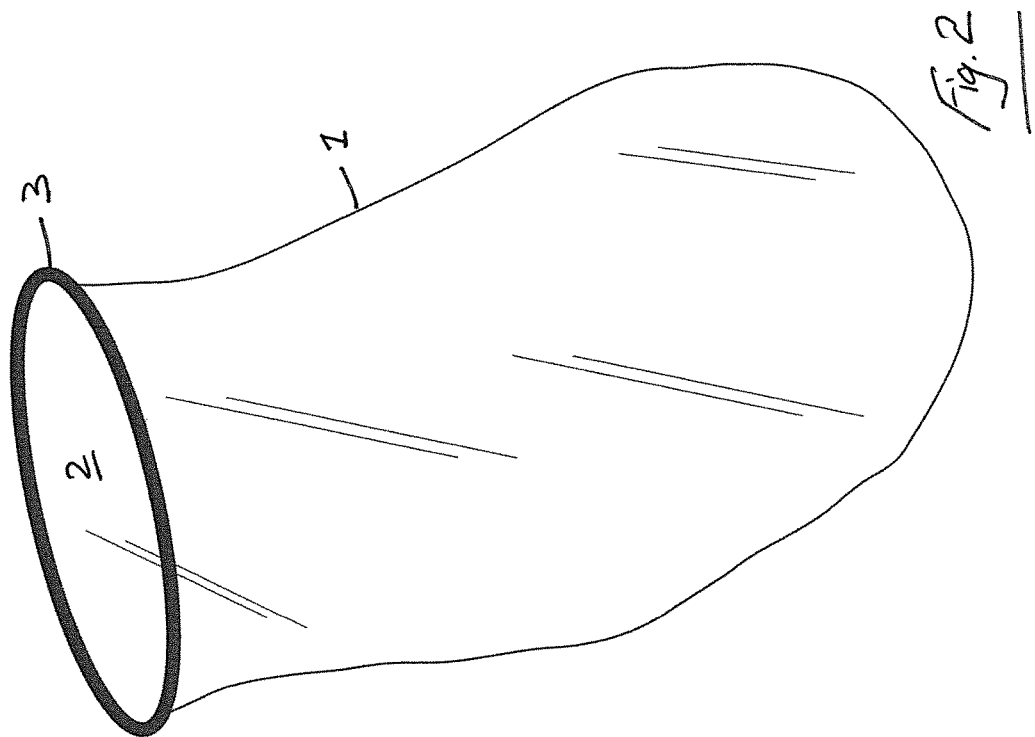
FIG. 2 is another isometric view of the device of FIG. 1.

Referring to the drawings, and initially to FIGS. 1 and 2 thereof, there is illustrated an apparatus for use in laparoscopic surgery comprising a bag 1 having an opening 2 to receive tissue and a ring element 3 extending around the opening 2. The bag is inflatable.

Referring to FIGS. 3 to 5, there is illustrated another bag device according to the invention which is similar to the bag device of FIGS. 1 and 2 and like parts are assigned the same reference numerals. In this case the bag has a necked region 5 to reduce the amount of material near the ring 3. This facilitates attachment of the bag to an external element.

The bag device 1 is suitable for use during laparoscopic surgery to facilitate procedures on tissue in an insufflated cavity while maintaining pneumoperitoneum.

The bag device 1 may be mounted to a retractor. One such retractor comprises a distal anchoring ring 10, a retractor member such as a sleeve 11, and a proximal ring assembly 12.

One such retractor is described in US 2005-0090717 A, the entire contents of which are incorporated herein by reference. The distal anchoring ring is located within a wound interior, in use. In this case the distal anchoring ring is provided in the form of an O-ring. The proximal ring assembly 12 is located externally of a wound opening, in use. The retractor member 11 may be employed to retract laterally the sides of a wound opening. In this case the retractor member is provided in the form of a sleeve.

The proximal end of the retractor is closable by a cap which in this case comprises an instrument access device 30 which may have a number of instrument ports 31 to effect a seal around an instrument extended through the device 30. The instrument access device 30 may be releaseably mountable to the proximal ring assembly 12. At least some of the instrument ports may include a stalk 32 which is laterally flexible and longitudinally rigid.

Figure 6:
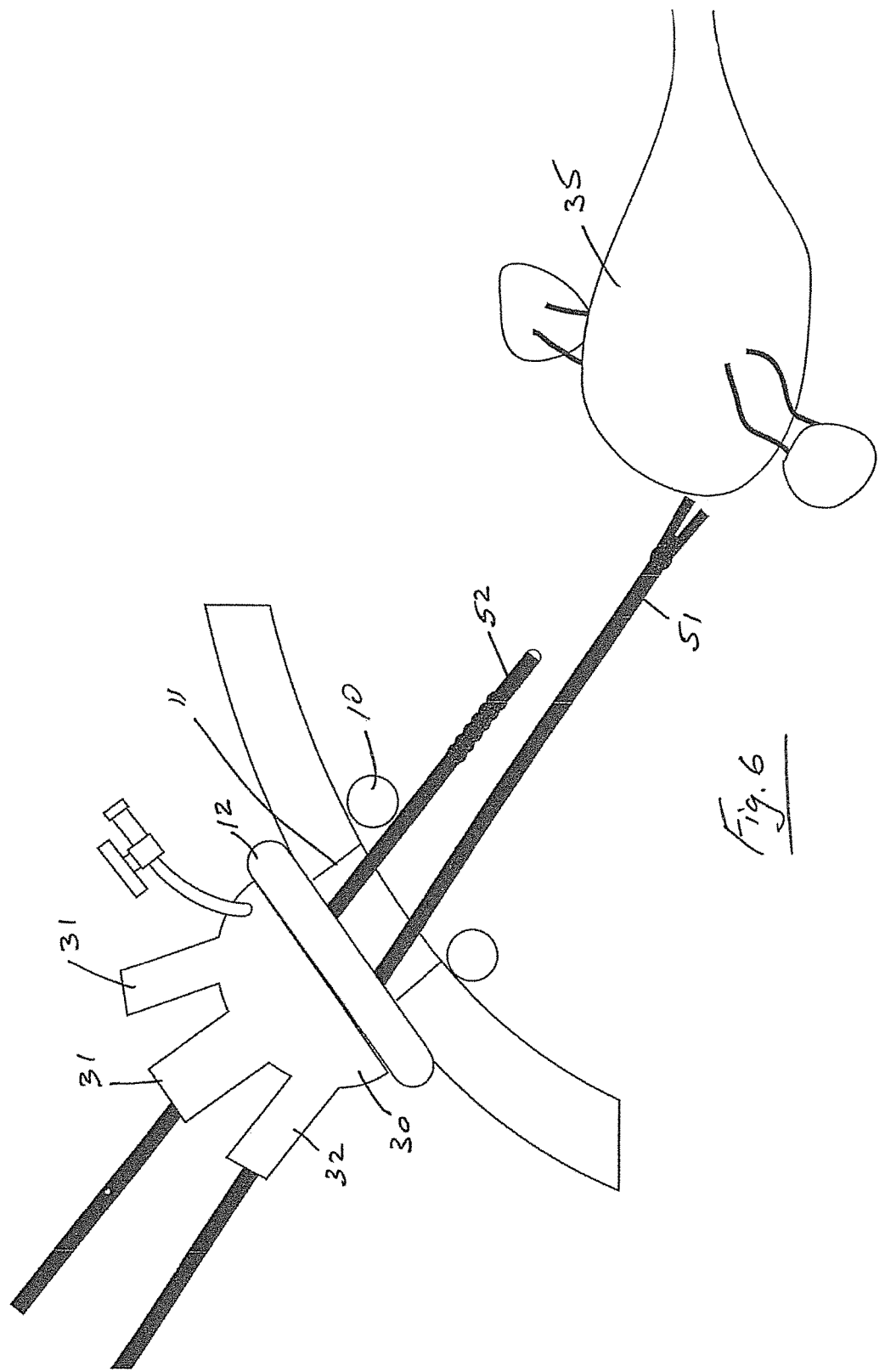

FIG. 6 illustrates an instrument 51 being introduced under vision provided by a camera 52 through an instrument access port.

FIG. 7 shows an organ or tissue such as an uterus 35 which has been severed from it's retaining structures.

FIG. 8 illustrates the bag device being inserted into the abdominal cavity at the beginning of a procedure or as and when required. The bag is inserted in a small flattened state for ease of insertion through a small opening such as an incision. The bag may also be introduced through a valve without the need to remove the access cap 30. One such arrangement is illustrated in FIG. 10.

When the bag is inserted it is opened up (FIG. 9). An organ is then readily manipulated for insertion into the bag as illustrated in FIG. 11. The rigidity of the O-ring 3 keeps the bag open to facilitate insertion of an organ.

Figure 15:
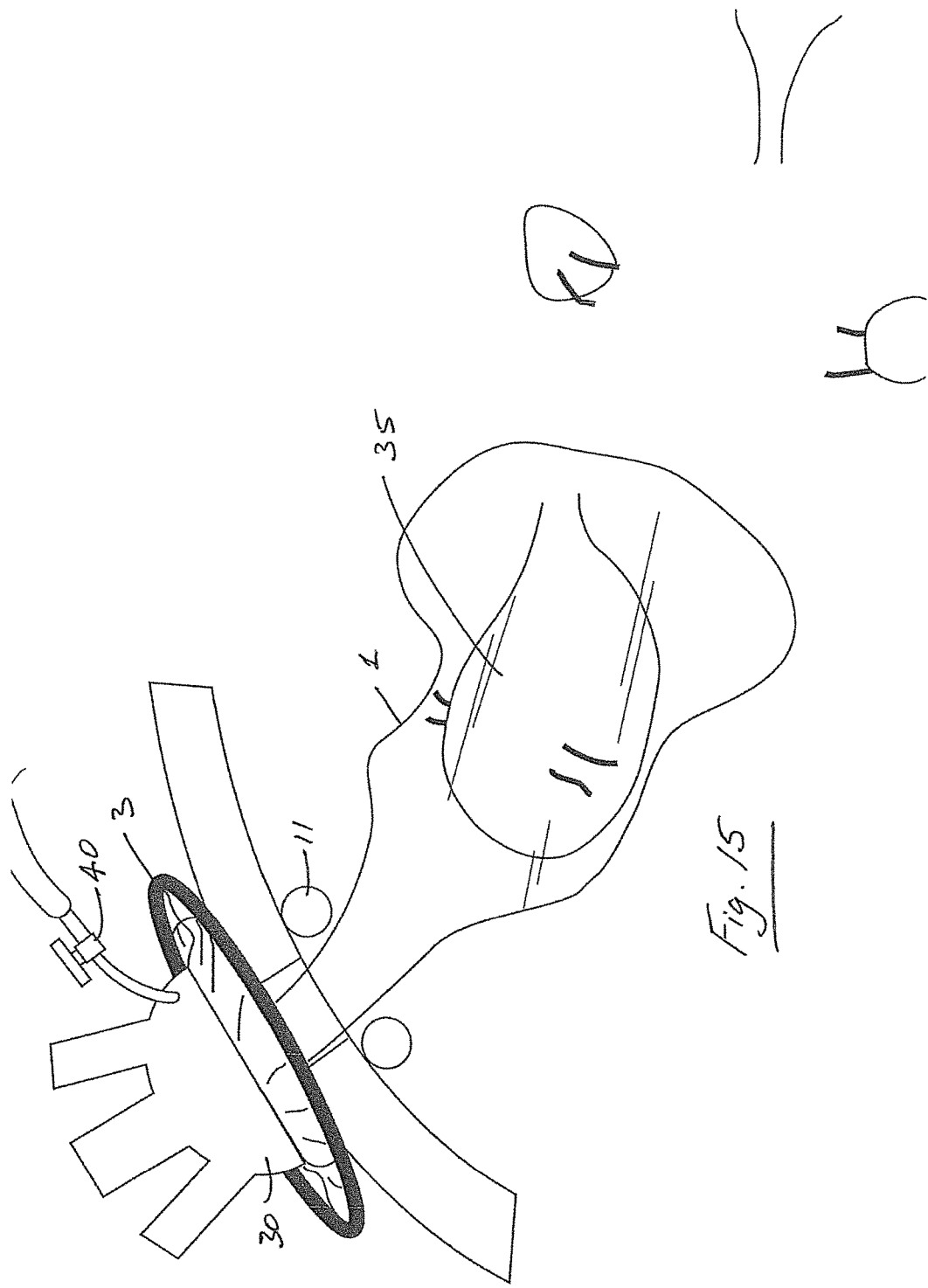

FIG. 12 shows the organ located in the bag and the O-ring 3 being grasped to facilitate manipulation of the bag towards the opening. The O-ring 3 is pulled out through the opening (FIG. 13) and the bag is mounted to the proximal ring assembly and the cap is mounted to the proximal assembly (FIG. 14). FIG. 15 illustrates the device in place with an organ enclosed within the bag.

Figure 16:

The bag is then inflated through an insufflation port 40. The inflation of the bag has the additional benefit of applying a retracting force to the materials outside the bag thereby creating additional space (FIG. 16).

Figure 17:
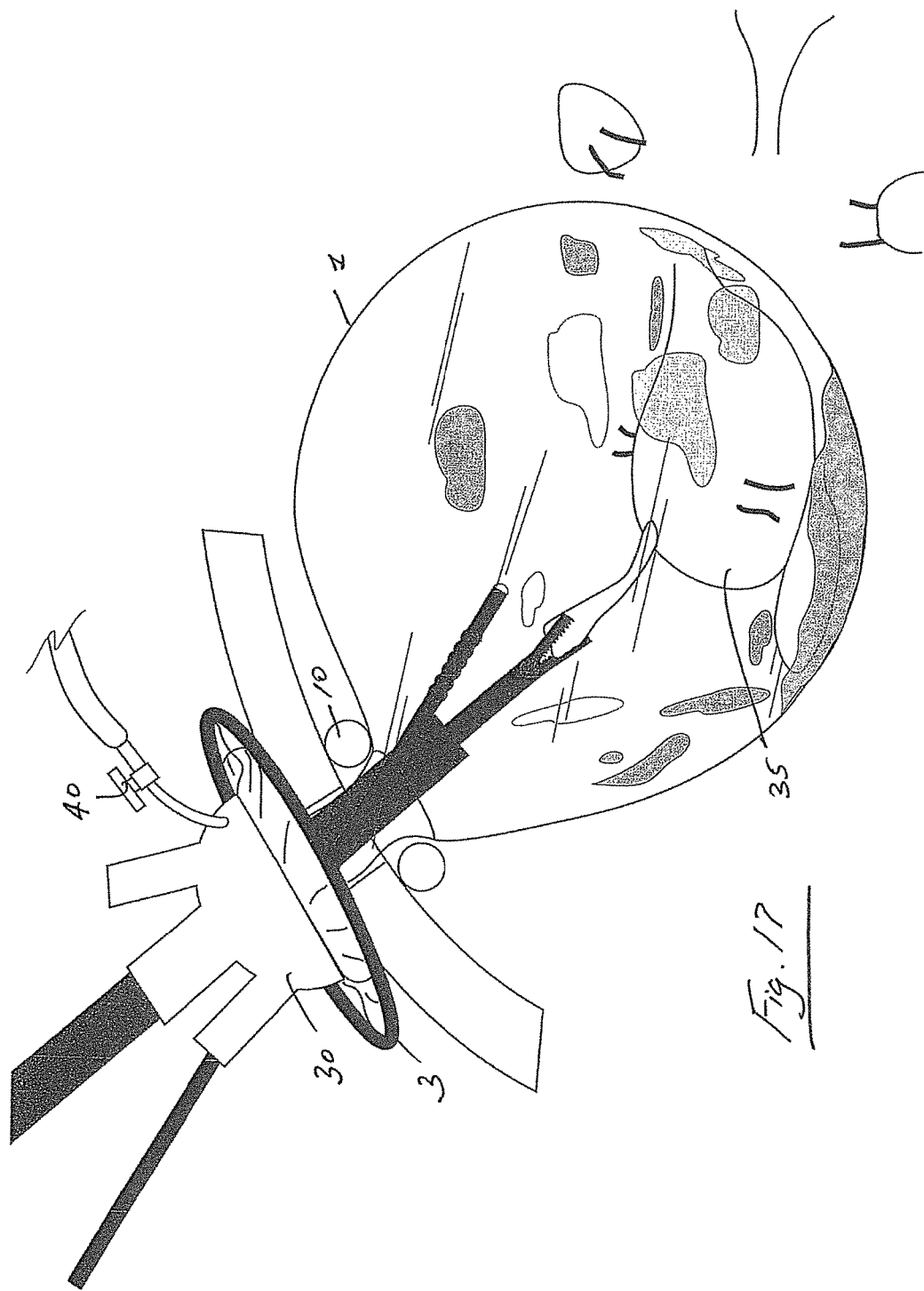
Figure 18:
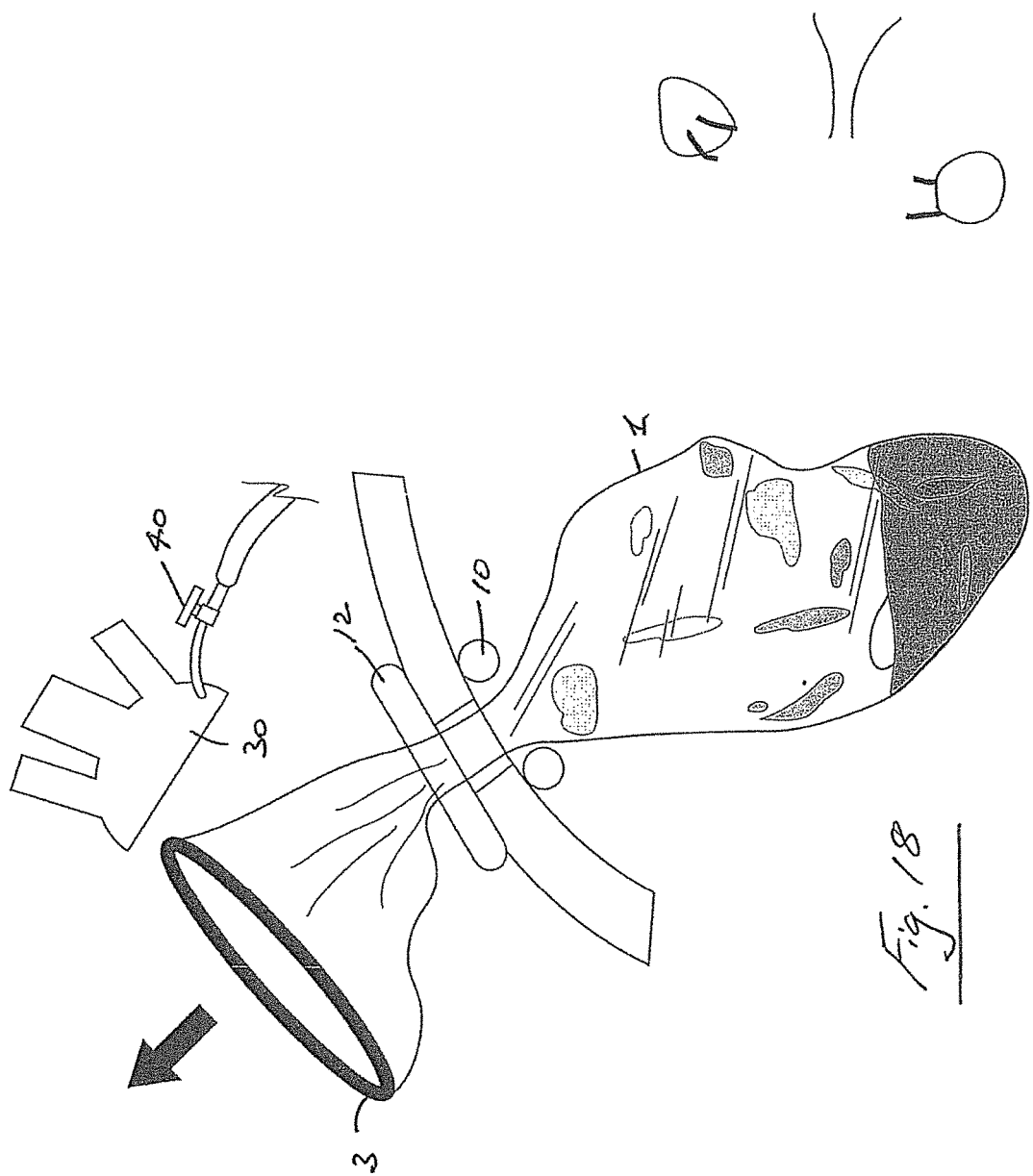

FIG. 17 shows an organ being worked on in the inflated bag. In this case the organ is morcellated. The material is all retained safely within the bag and is not released into the cavity which could cause major difficulties.

When the organ has been morcellated the bag is readily removed through the original opening. All waste, blood, tissue and the like are safely removed and sealed within the bag.

FIG. 19 shows the bag device being inserted through a standard naked incision. Once the specimen has been inserted into the bag (FIG. 20) the ring 3 is pulled back out through the incision (FIG. 21) and a trocar 60 is inserted to create a gas seal (FIG. 22). It may also be possible to insert the bag device directly through a trocar.

In all cases there may be one or more access trocars used in addition to the primary port. Thus, the invention includes procedures which involve two or more incision laparoscopy.

Figure 24:
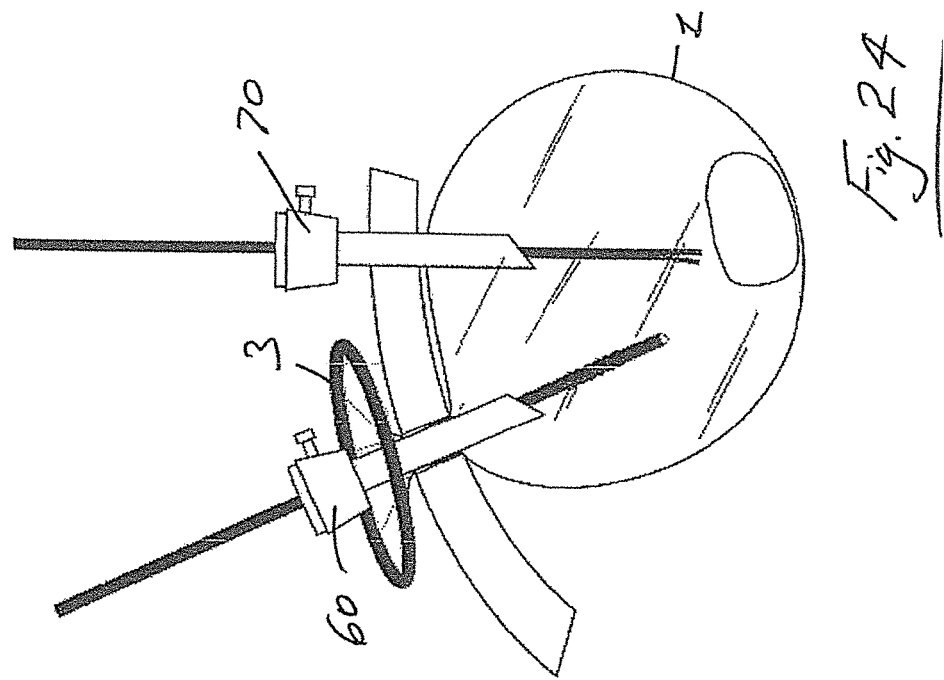
FIGS. 23 to 24 are diagrams illustrating a further use of the device of FIGS. 1 to 5.
Figure 23:
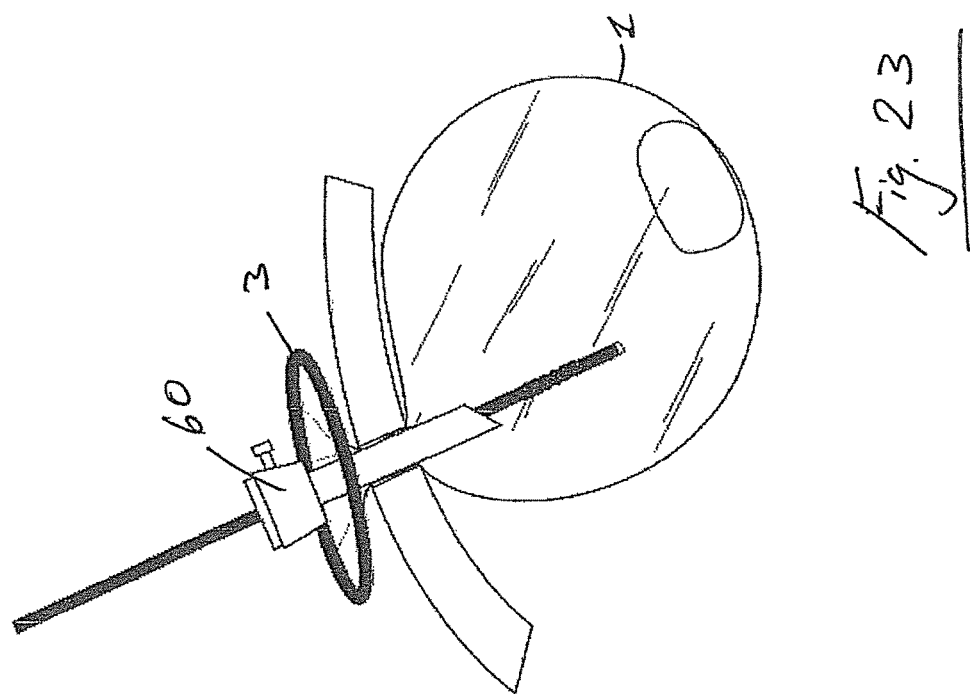

For example, FIGS. 23 and 24 show one arrangement in which an additional trocar 70 is inserted. In some cases, the additional trocar 70 may be extended through the bag whilst maintaining a seal.

A bag is illustrated which has some depth which is preferred. However, a flat material can be used to form a holder in situ and the edges of the material pulled out through an incision and sealed outside, for example by an access device.

The invention provides a method of inserting a large bag into the abdominal cavity to allow the insertion of a specimen into the bag. The bag is then sealed and inflated and procedure carried out within the bag.

FIGS. 25 to 30 show various ways a bag 79 may be introduced into the abdomen.

In FIG. 25 the device may be inserted directly through an incision 80.

Referring to FIG. 26 the device may be inserted through a trocar 81.

In FIG. 27 a device may be inserted through a base retractor 82.

Referring to FIG. 28 a device may be inserted through a low profile port 83.

As shown in FIG. 29 the device may be inserted through a Multi-port device 84. The multiport device may, for example, be of the type described in U.S. Pat. No. 8,187,178 or US20110071389A, the entire contents of which are incorporated herein by reference.

Referring to FIG. 30 the device may be inserted through the base 85 of a multi-port device.

Figure 31:
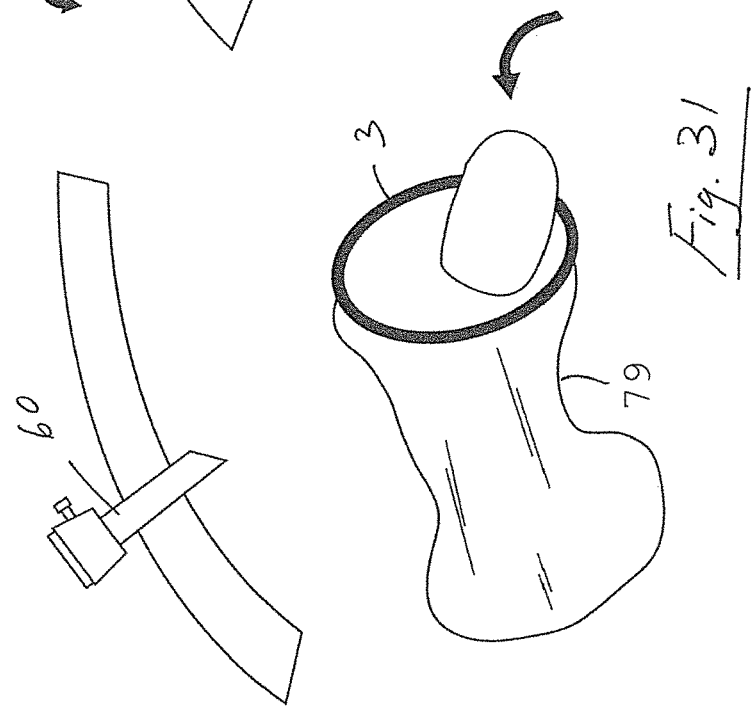

As illustrated in FIG. 31, once the bag 79 has been inserted the specimen is placed inside.

Figure 32:
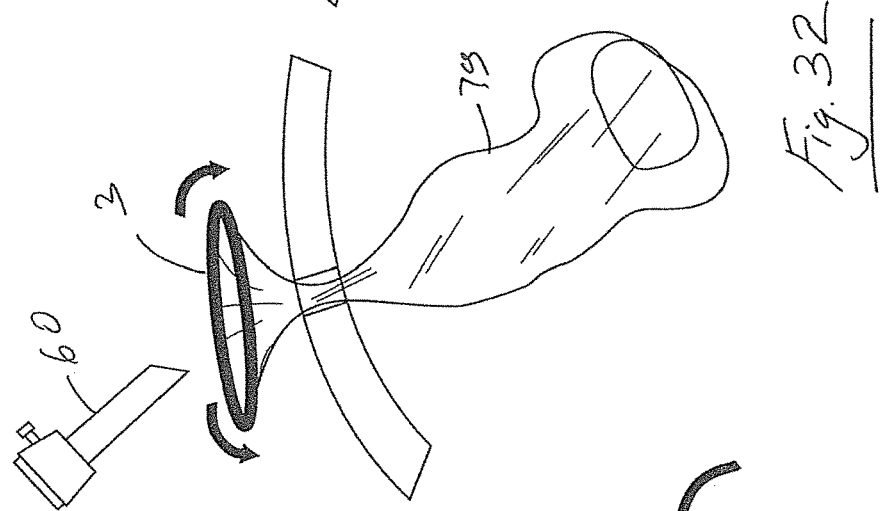

FIG. 32 the lip of the bag 79 is pulled out through the opening.

Figure 33:
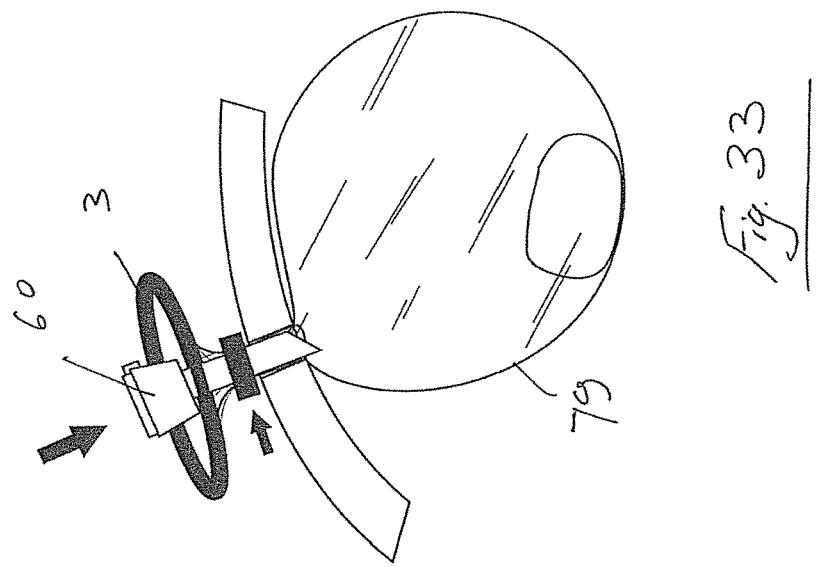

FIG. 33 the bag 79 is sealed by re-inserting the trocar 60, replacing the cap or inserting a morcallator 78. If necessary an extra seal may be applied to the neck of the bag 79.

As shown in, FIG. 34, once the bag is inflated additional trocars may be inserted into the abdomen as normal and pierced through the bag 79. FIG. 34 also shows a morcallator 78 inserted through a trocar 60.

FIG. 35 shows the morcallator 78 being inserted without the need for a trocar. A sealing ring 77 may be applied around the shaft of the morcallator 78 if necessary to hold back gas.

Referring to FIGS. 36 to 45 a method of inserting a large bag 100 into an abdominal cavity which may automatically open to allow the insertion of a specimen is illustrated. The bag 100 is foldable and has a top opening 105 which may be biased into the open configuration by retaining elements which in this case comprise semi-circular ring parts 101, 102 which have attached tether elements 104, 103 respectively. A pouch 110 is used to house the bag 100 in a folded/retracted configuration. The pouch 110 has a grasping tab 111 and a pull string 115.

FIG. 36 illustrated the main components of the automatically opening bag device.

FIG. 37 illustrates a folded bag 100 inside the pouch 110. In FIG. 38 the pouch 110 is inserted into the abdominal cavity with the aid of the grasping tab 111. When the pouch is inside, the distal pull tether 104 is pulled forward and the bag 100 is released. A rear pull string 115 is pulled in the opposite direction to aid release.

Referring to FIG. 40, it will be noted that as the distal end of the bag 100 is pulled forward the rear of the bag 100 is pulled in the opposite direction as it is attached to the pouch 110 with the connecting tether 15. This action opens the mouth of the bag sufficient to ease the inserting of specimens.

FIG. 41 shows specimens being placed on top of the bag opening 105.

Referring to FIG. 42, by pulling the distal pull tether 104 back and over the specimen, the bag 100 begins to unroll and the specimen travels deeper insider the bag. Referring to FIG. 43, as the front and back retaining elements 101, 102 of the bag opening are pulled outwards, the specimen travels further into the bag.

FIG. 44 shows the rim of the bag being opened up and the incision being cleared of excess bag material.

Referring to FIG. 45, the opening is re-sealed by attaching a cap, by inserting a trocar, or by inserting a morcallator through the opening.

Referring to FIGS. 46 to 54 there is illustrated another device according to the invention. The device is similar to that of FIG. 36 to 45 and like parts are assigned the same reference numerals. In this case a bag 120 is housed within a cartridge 121 for delivery and automatically opens when it exits the cartridge on insertion into the abdominal cavity. In this case the ring part 102 remains attached to the cartridge 121. A tether 125 extends between the distal end of the cartridge 121 and the ring element 102. The ring element 101 has a tether element 126 which is grasped by an instrument 127 to pull the bag 120 from the cartridge 121.

FIGS. 46 to 54 show the bag 120 housed in the cartridge 121 which can be inserted into a valve on an access port/trocar 130. The cartridge 121 remains in place during the procedure.

Referring to FIG. 46, the loaded cartridge 121 is placed through a valve on the port 130. FIG. 47 shows the distal pull tether 126 that is positioned so that it is easily grasped with an instrument 127. In FIG. 48 an instrument 127 is inserted and the pull tether 126 is grasped.

Referring to FIG. 49, as the grasper 127 is pushed forward the bag 120 is released from the cartridge 121. As shown in FIG. 50, once the bag is in far enough, the tether 125 which connects the back side of the bag 120 to the cartridge 121 begins to open the bag up.

Referring to FIG. 51, when the mouth of the bag 120 is sufficiently open a specimen may be placed inside. When the distal pull tether 126 is pulled back as illustrated in FIG. 52 this forces the bag to unroll and the specimen to travel deeper into the bag.

Referring to FIG. 53, the cap/trocar 130 is then removed and the rim of the bag 120 is pulled out through the incision and mounted to the retractor 135. FIG. 54 shows the cap, trocar or morcallator reconnected. The bag 120 is then inflated.

Referring to FIGS. 55 to 63, there is illustrated a removable cartridge 140 with a manually opened bag 141 for insertion through a single port 142. These drawings illustrate a method of inserting a large bag 141 which will be manually opened by the user when inserted into the abdominal cavity. FIGS. 55 to 63 show a bag 141 housed in a cartridge 140 which plugs into a valve 142 on an access port/trocar. The bag is ejected from cartridge 140 using a plunger 145 and the cartridge 140 is removed.

Referring to FIG. 55, the bag 141 is loaded into a cartridge 140 which is then inserted through a valve 142 on the port/trocar. When the cartridge 140 is in place of the plunger 145 is inserted through the proximal end of the cartridge 140 as illustrated in FIG. 56. Pushing the plunger 145 down as illustrated in FIG. 57 forces the bag 141 to eject into the abdominal cavity.

Figure 59:
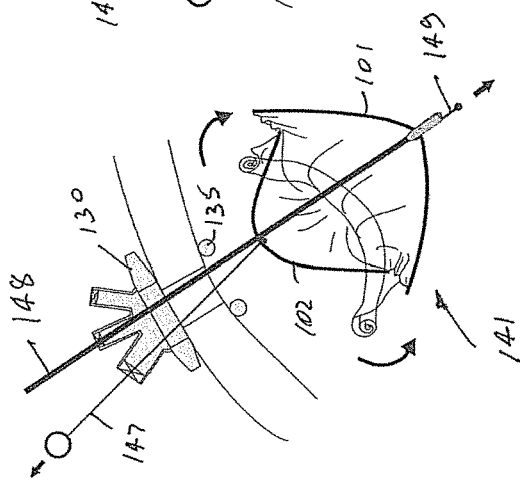
Figure 58:
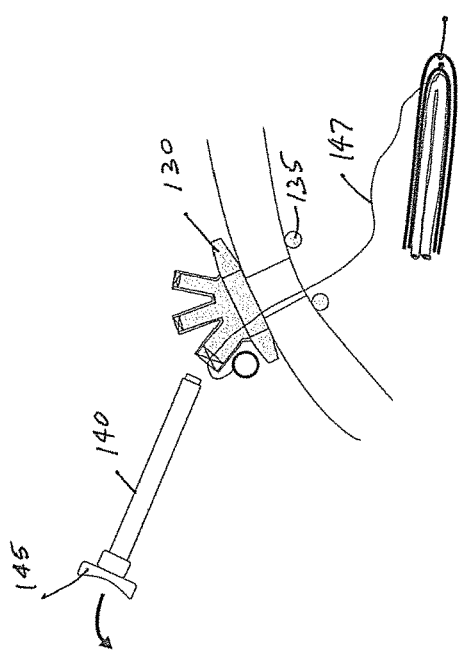

Referring to FIG. 58, when the bag 141 has been ejected, the cartridge 140 may be removed, leaving an activation tether 147 in place. An instrument 148 is inserted as illustrated in FIG. 59 and the instrument is used to grasp the distal pull tether 149 which is attached to the front band 101 on the bag 141.

Figure 60:
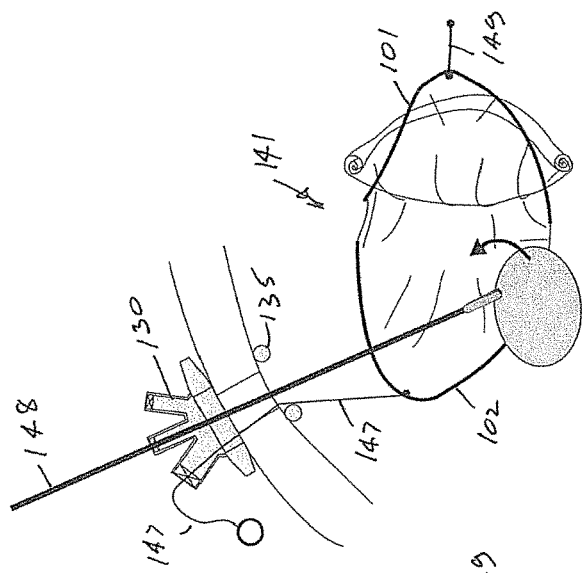

Referring to FIG. 60, the specimen is then lifted into the open mouth of the bag 141. The surgeon can control the mouth of the bag 141 using the activation tether 147. When both the front and the back ring elements 101, 102 of the bag 141 are grasped as illustrated in FIG. 61, the bag 141 can be pulled towards the incision, forcing the specimen to travel deeper into the bag 141.

FIG. 62 shows the valve/trocar being removed and the rim of the bag being pulled out through the incision. In FIG. 63, the rim of the bag 141 is opened up, and the valve/trocar are replaced to seal the bag 141. The bag 141 is then inflated and the procedure carried out within.

Referring to FIGS. 64 to 74 there is illustrated a removable cartridge 150 with a manually opened bag 151 (laparoscopic). These drawings show a method of inserting a large bag 151 which can be manually opened by the user when inserted into the abdominal cavity.

Figure 66:
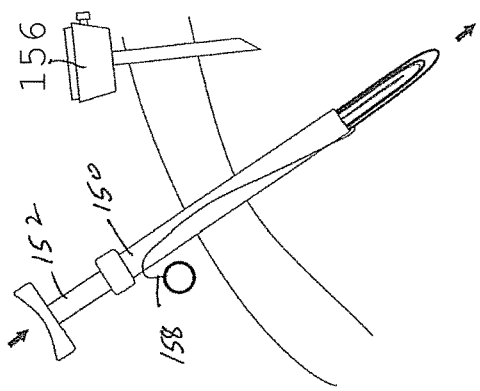
Figure 65:
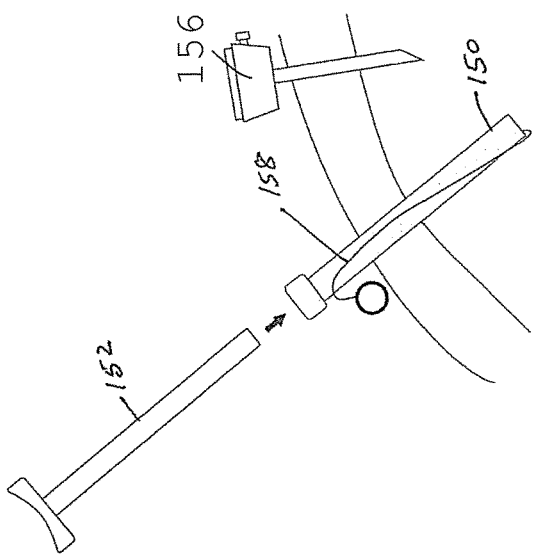
Figure 64:
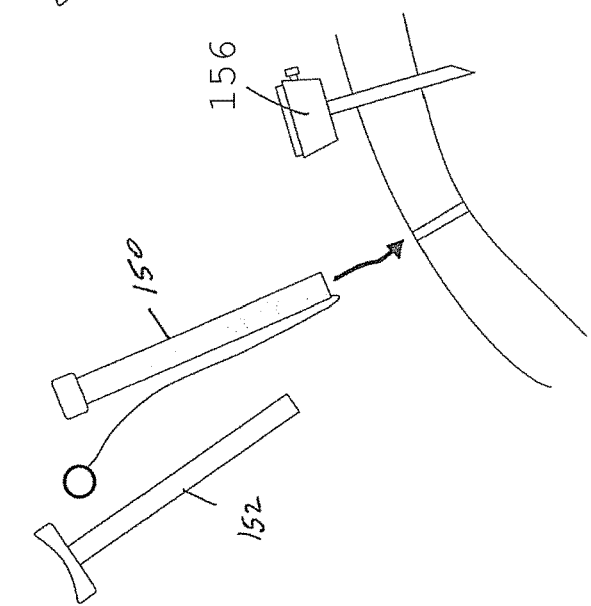
FIG. 64 is a diagram of another device according to the invention.
Figure 65:
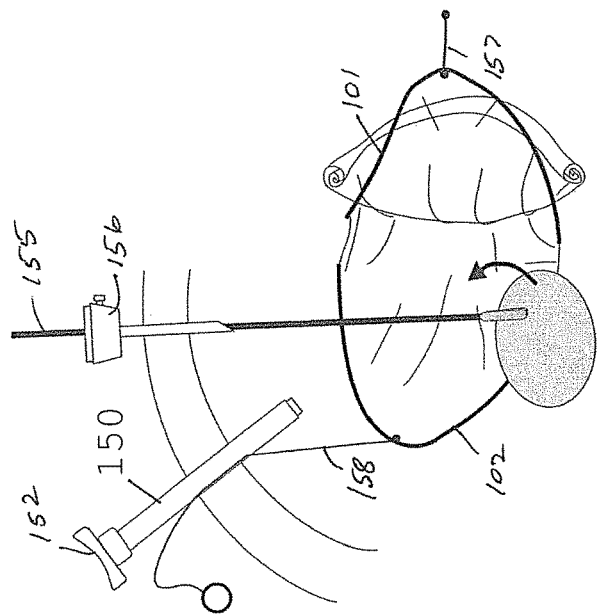
Figure 67:
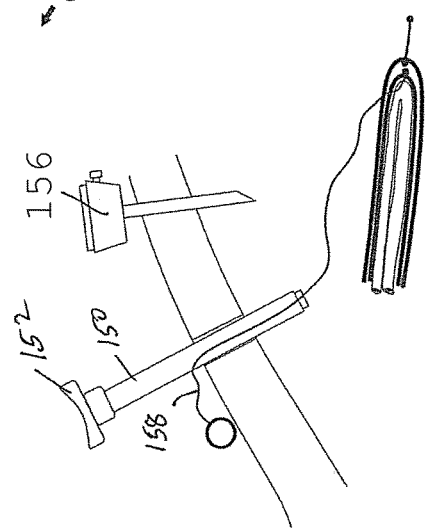

Referring to FIG. 64, the loaded cartridge 150 is inserted through a pre-made incision. When the cartridge 150 is in place a plunger 152 is inserted as illustrated in FIG. 65. The plunger 152 is pushed all the way down and the bag 151 is ejected as shown in FIGS. 66 and 67.

Figure 68:
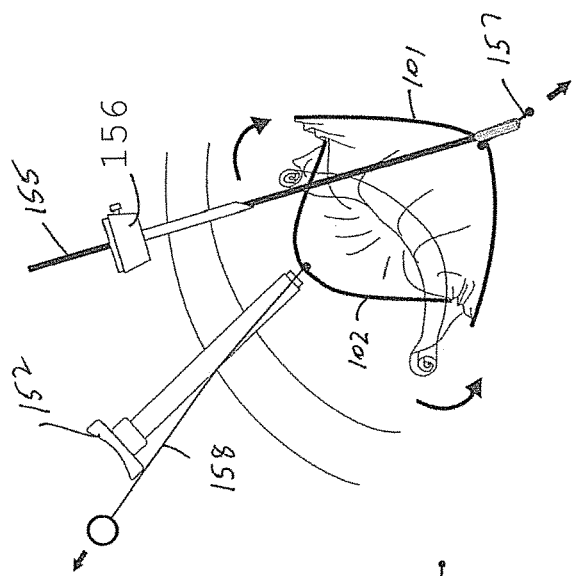

Referring to FIG. 68 an instrument 155 is inserted through a trocar/access port 156 and is used to grasp a distal pull tether 157 which is attached to the front band on the bag. Once the distal tether is held, pulling on the activation tether opens the mouth of the bag and forces the excess material to unroll. The specimen may now be lifted into the open mouth of the bag as shown in FIG. 69. The surgeon can control the mouth of the bag to some degree with an activation tether 158.

Figure 72:
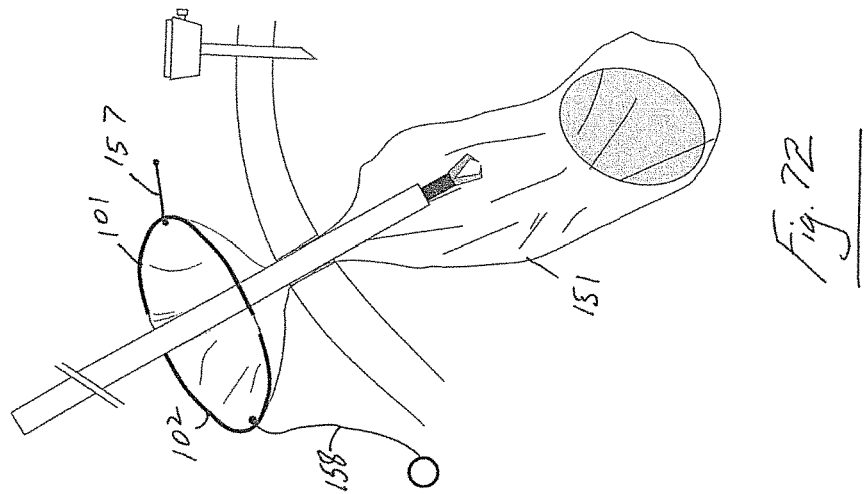
Figure 71:
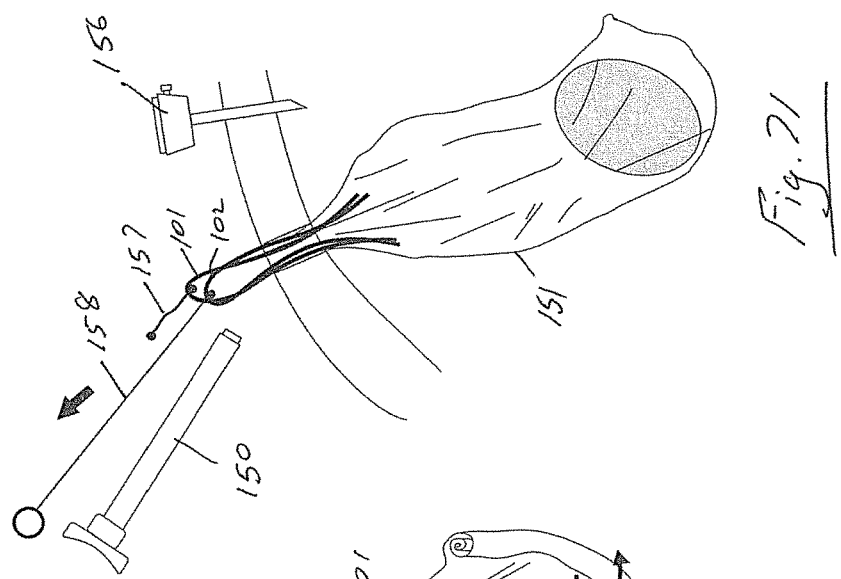
Figure 70:
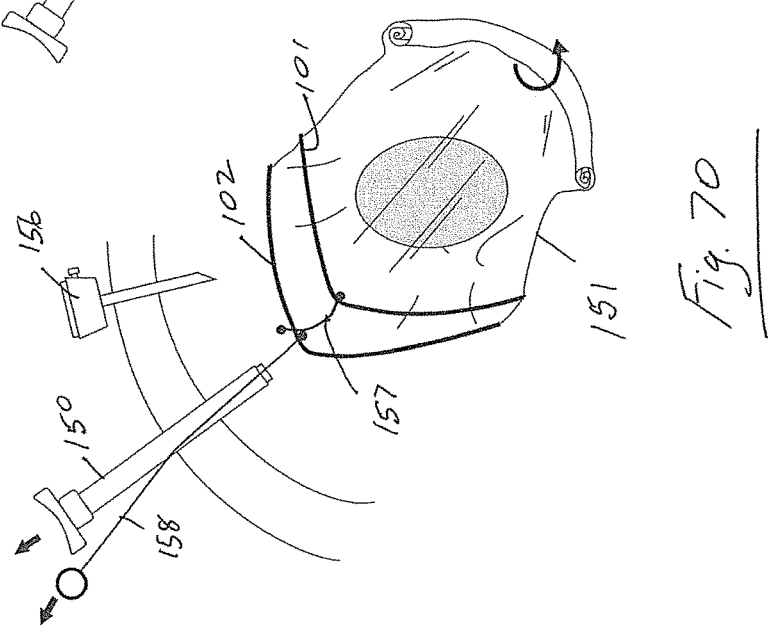

Referring to FIG. 70, with the back end of the bag 151 grasped, the bag can be pulled towards the incision, forcing the specimen to travel deeper into the bag 151. The valve/trocar is removed and the rim of the bag is pulled out through the incision as illustrated in FIG. 71. The rim of the bag is opened up, and the morcallator is reinserted to seal the bag as shown in FIG. 72. The bag is then inflated and the procedure carried out within.

Figure 74:
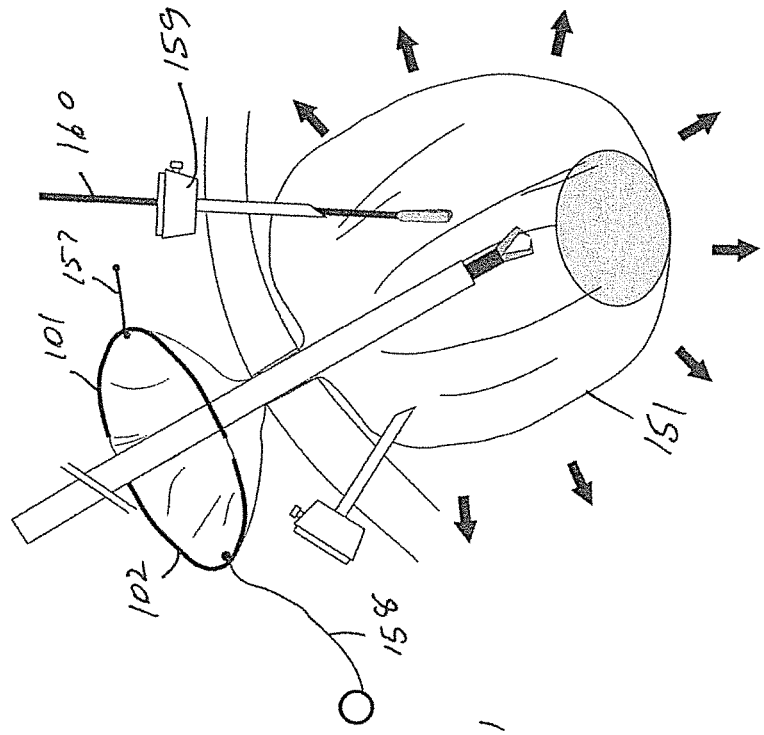
Figure 73:
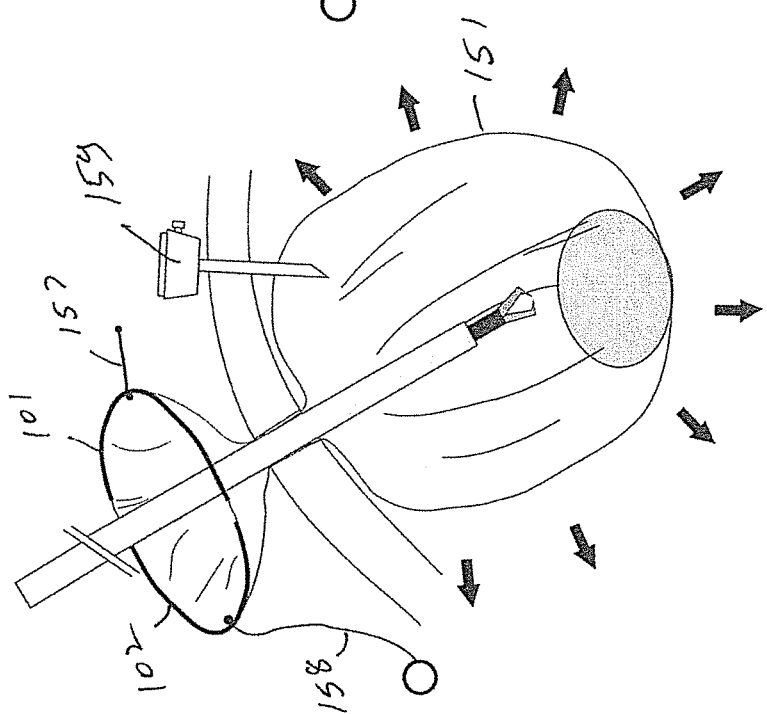

As illustrated in FIGS. 73 and 74, when the bag is inflated trocars 159 can be pierced through to allow access for additional instruments 160.

Figure 76:
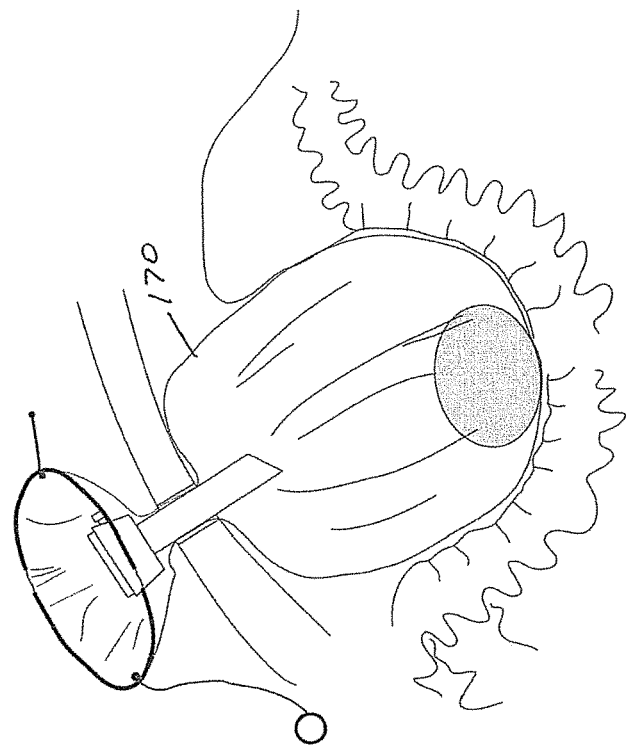
FIGS. 76 to 78 are diagrams illustrating the device of FIG. 75, in use.
Figure 75:
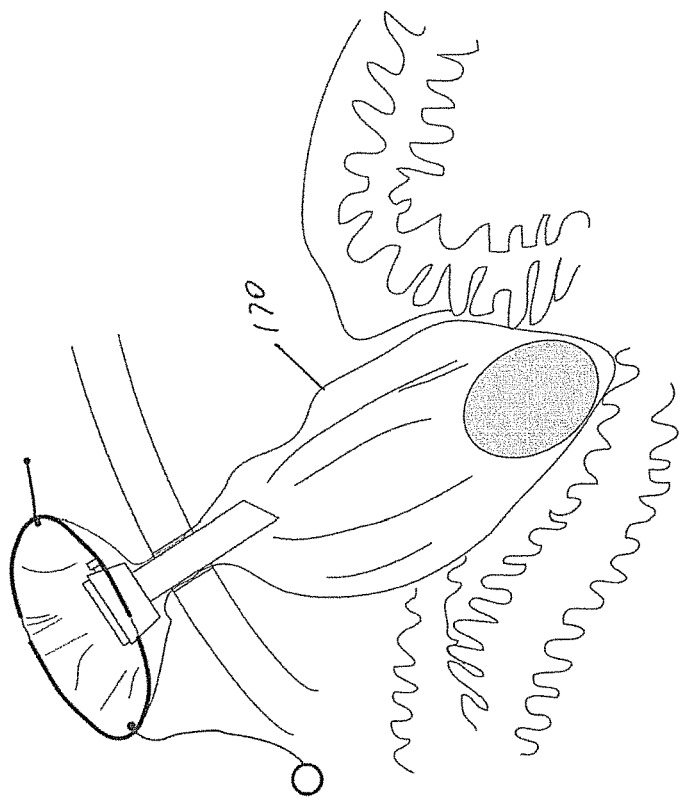
FIG. 75 is a diagram of a device according to the invention for use as a visceral retainer.

Referring to FIGS. 75 to 87 there is illustrated the use of a bag 170 as described above as a visceral retainer. The bag 170 is first inserted and positioned where required (FIG. 75). As the bag 170 is inflated surrounding structures and organs are retracted as shown in FIG. 76.

Figure 78:
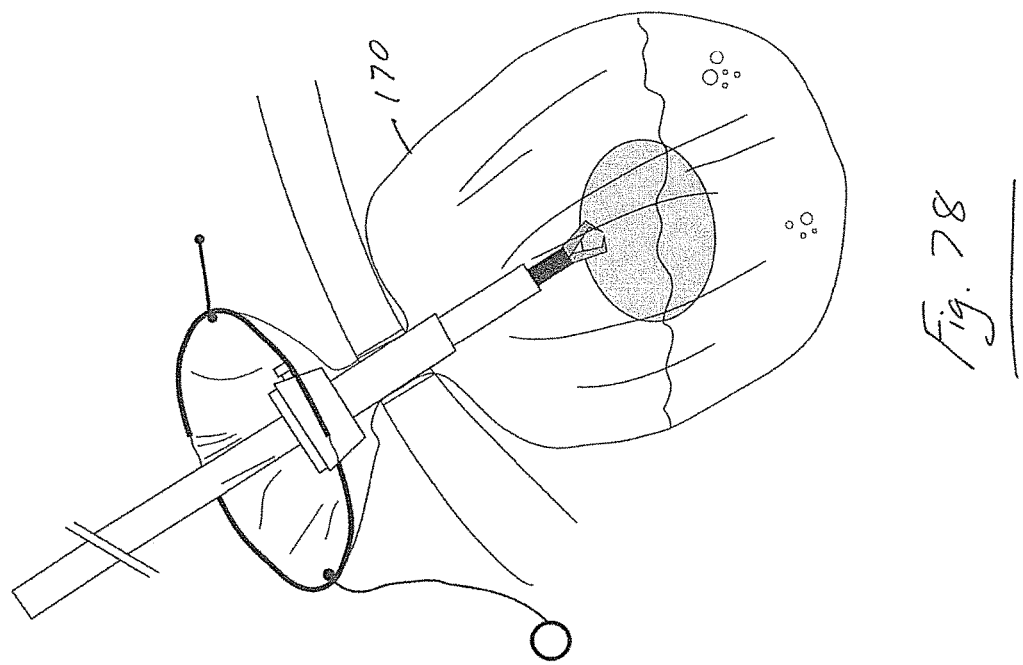
Figure 77:
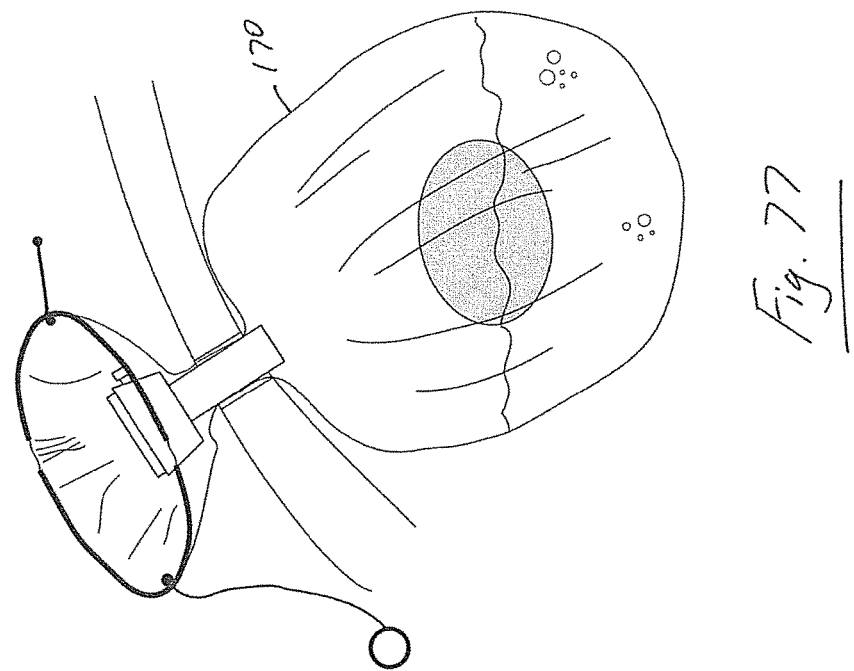

As shown in FIGS. 77 and 78, it may be of benefit to fill, or partially fill the bag 170 with a liquid. These benefits may include: 1) The specimen floats to the top of the bag and therefore the risk of bag damage at the base may be reduced, 2) Liquid may reduce smoke build up in the bag. 3) Blood will be diluted and may therefore allow for enhanced visibility.

Figure 80:
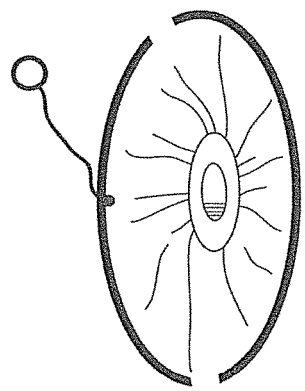
FIGS. 80 and 81 are diagrams illustrating the device of FIGS. 75 to 78 in use.
Figure 79:
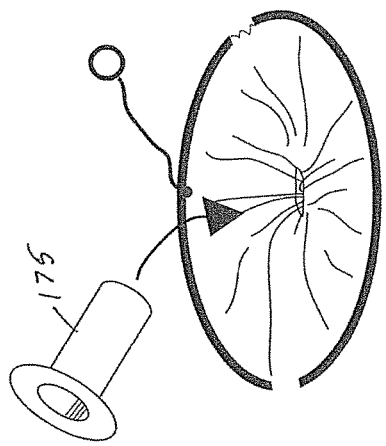
FIG. 79 is a diagram of the device of FIGS. 75 to 78 with an associated grommet.
Figure 81:
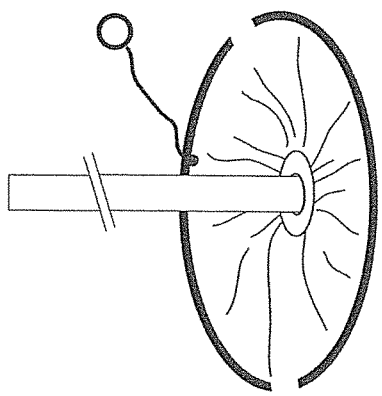

Referring to FIG. 79, when the bag 170 is in place and the neck has been pulled through the incision there is often a lot of excess material in the incision. A grommet 175 may be inserted through the bag/incision to keep excess material away from the incision as illustrated in FIG. 80. This will help prevent damage to the bag and aid visibility and gas flow. With the grommet 175 in place instruments can be inserted with ease as shown in FIG. 81.

Figure 82:
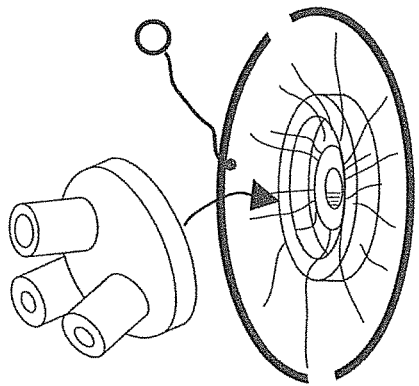

The grommet 175 may be used with multiport or single port access devices (FIG. 82).

In some cases the grommet 175 have an insufflation/desufflation line 176 built in (FIG. 83).

As illustrated in FIG. 84 the grommet may include a series of slits 177 which allow it to conform to various incision dimensions.

The grommet may include a valve system 178 as illustrated in FIG. 85.

An instrument locking mechanism 179 may also be included (FIG. 86).

In some cases, as illustrated in FIG. 87, the grommet may have a series of lumen 180 to aid with ventilation/insufflation.

Referring to FIGS. 88 and 89 there is illustrated a bag device 200 according to the invention. In this case, the bag 200 is shown in the inflated configuration within a body cavity such as the abdomen. A tissue sample 201 is contained within the bag. An incision is made in the abdomen 202 and the incision is retracted using a retractor 203 as described above. In this case the retractor has an outer proximal ring 204 and a multilumen access port 205 is releasable mounted to the ring 204. The bag 200 extends through the retracted incision and terminates in a retainer ring 206.

FIGS. 90 and 91 illustrate a bag device similar to that shown in FIGS. 88 and 89 but in this case a single instrument lumen access port is mountable to a proximal part 100 of the retractor assembly. The access port 211 may have a cannula section that extends through the retractor or may be an access port 212 with a short proximal leg.

The bag device may itself have an access port to facilitate passage of instruments into and out of the bag and/or to facilitate passage of a tissue sample into the bag.

Figure 94:
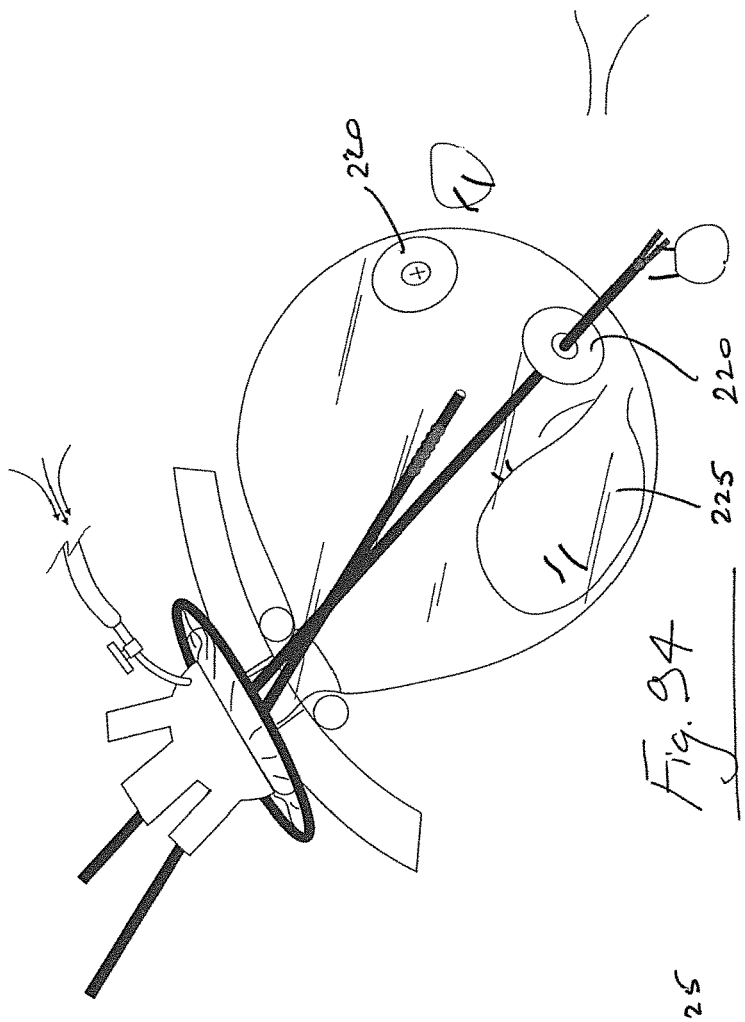
FIG. 94 is an isometric view of another device similar to FIG. 93 with a number of exit ports.
Figure 93:
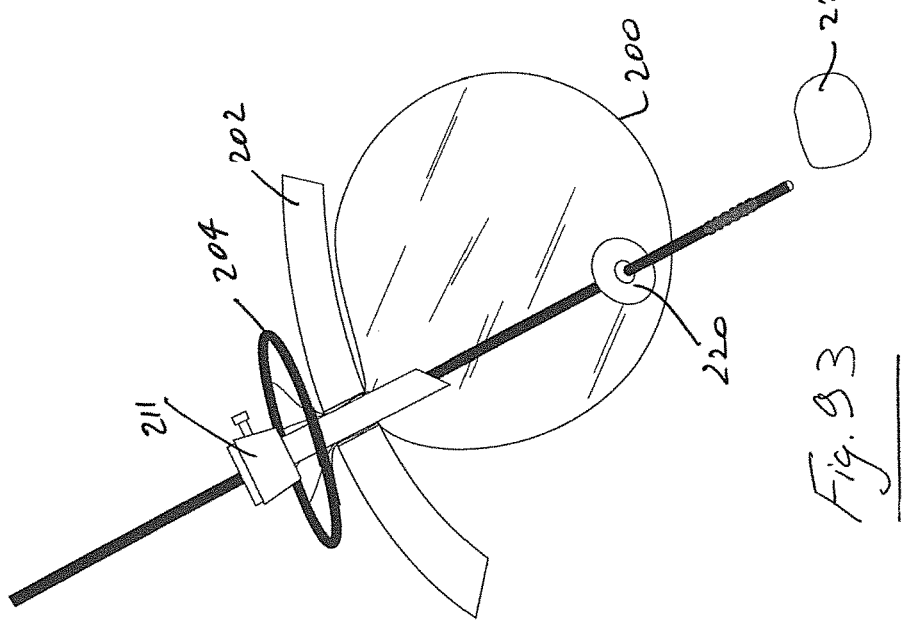
FIG. 93 is an isometric view of a pneumoperitoneum device according to another embodiment of the invention with an exit port from the device.

Referring to FIG. 93 the bag has a single access port 220. However, there may be a plurality of such access ports as illustrated in FIG. 94. Passage of a tissue sample 225 through an access port 220 is illustrated in FIG. 95. The access port 220 may be provided with any suitable valve such as a choke valve, for example, for example a drawstring 226 as illustrated in FIG. 96, a cuff valve 227 as illustrated in FIG. 97, or an elastomeric valve 228 as illustrated in FIG. 98. The valve 228 may be of any suitable plastics, rubber or gel material.

Referring to FIGS. 99 to 110 there is illustrated various steps in methods involving the use of the bag devices of the invention. In the example illustrated the device is of the type described above. The methods involve the use of a bag device 250, a retractor 251, an external access port system 252 and is used to access tissue 253 such as a specimen or an organ through an opening 254 in the body, in this particular case in the abdomen 255. The bag device has a delivery configuration in which it is housed in a retracted condition in a cartridge 260. A plunger 261 is used to deliver the retracted bag device out of the cartridge 260. The bag device 250 has an opening which is biased into an open configuration by a retainer ring 265. The ring 265 may be of a shape memory material as described above. A proximal tether which in this case is in the form of a ring or loop 267 is provided on one side of the ring 265 and a distal tether 268 extends from the side of the ring 265 generally opposite to the proximal tether 267.

Figure 104:
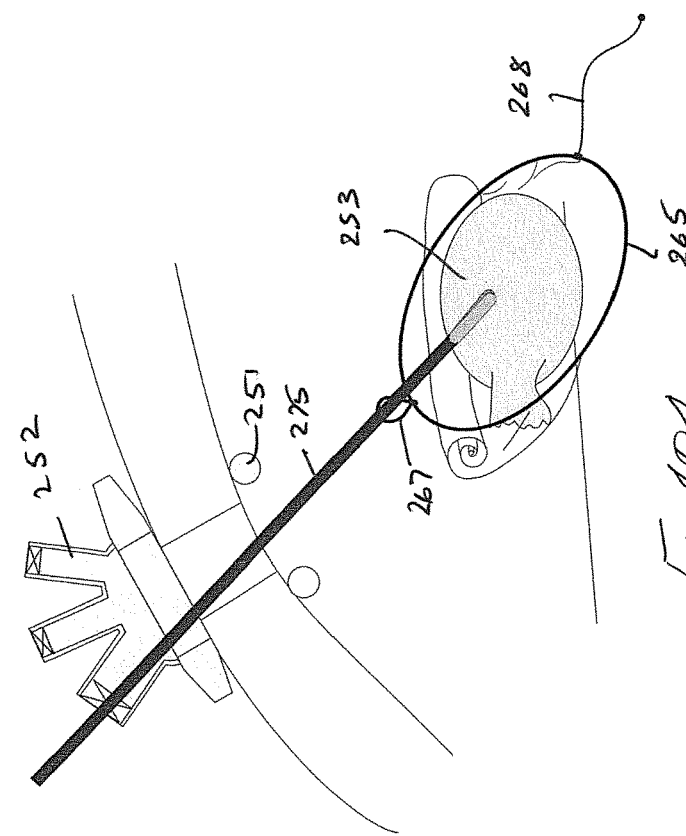
Figure 103:
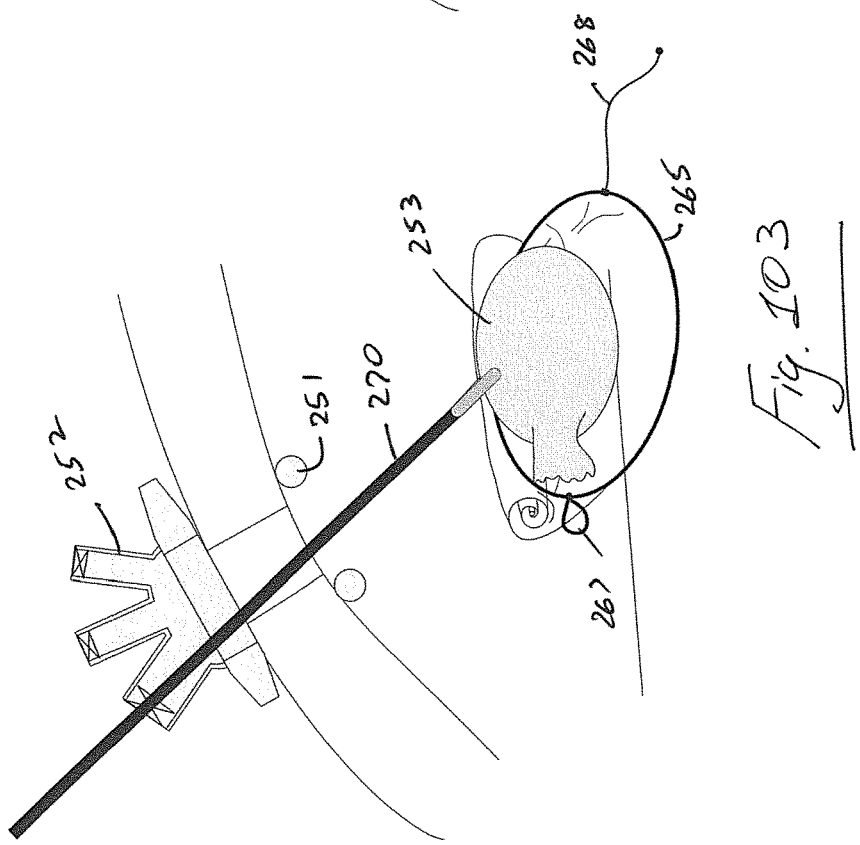
Figure 106:
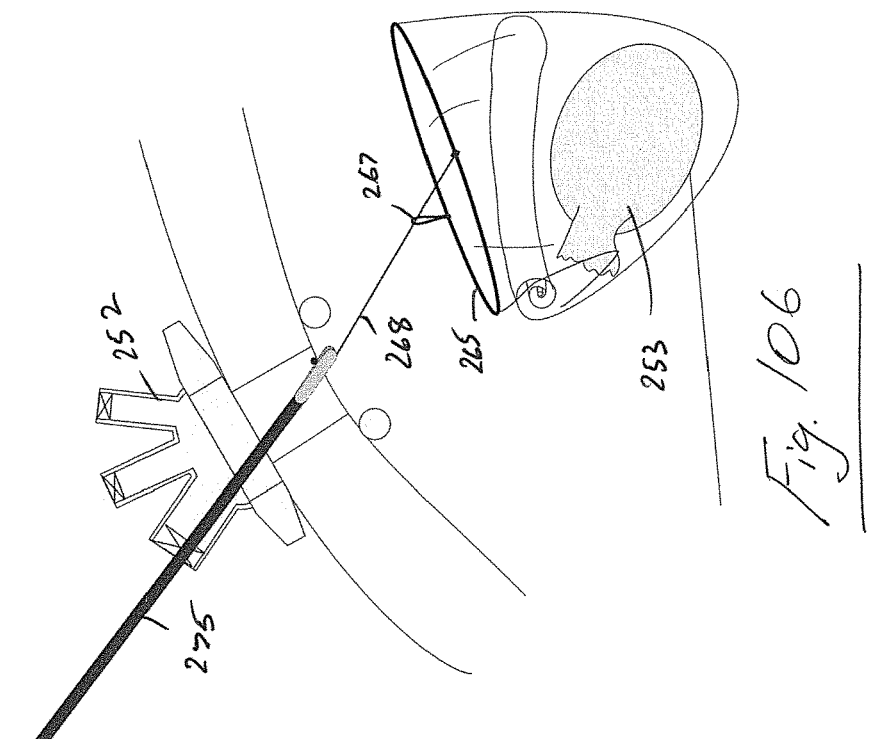
Figure 105:
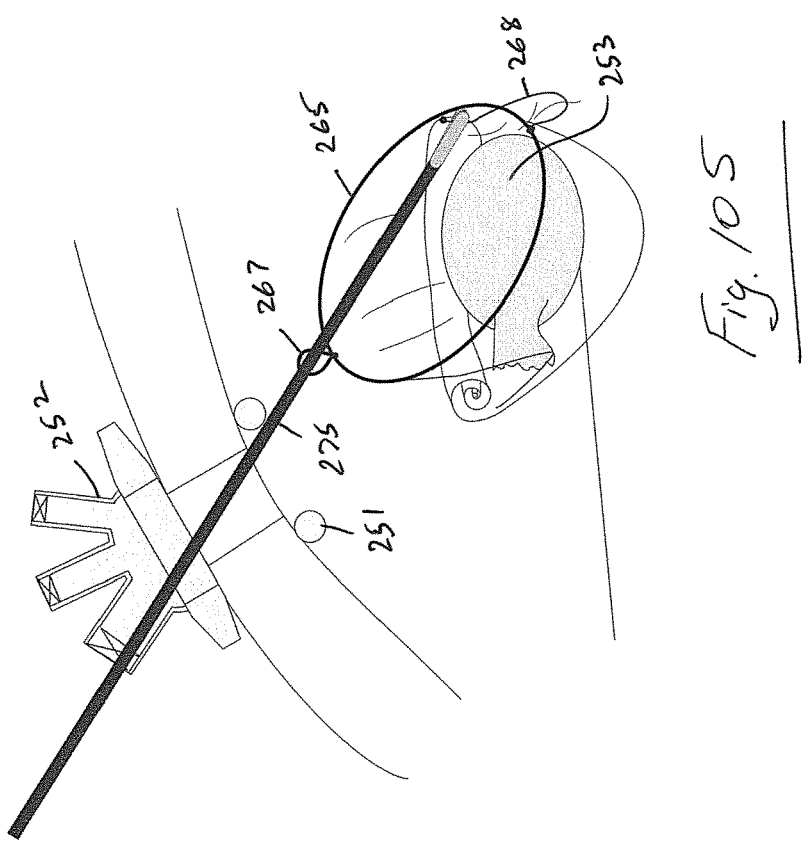
Figure 107:
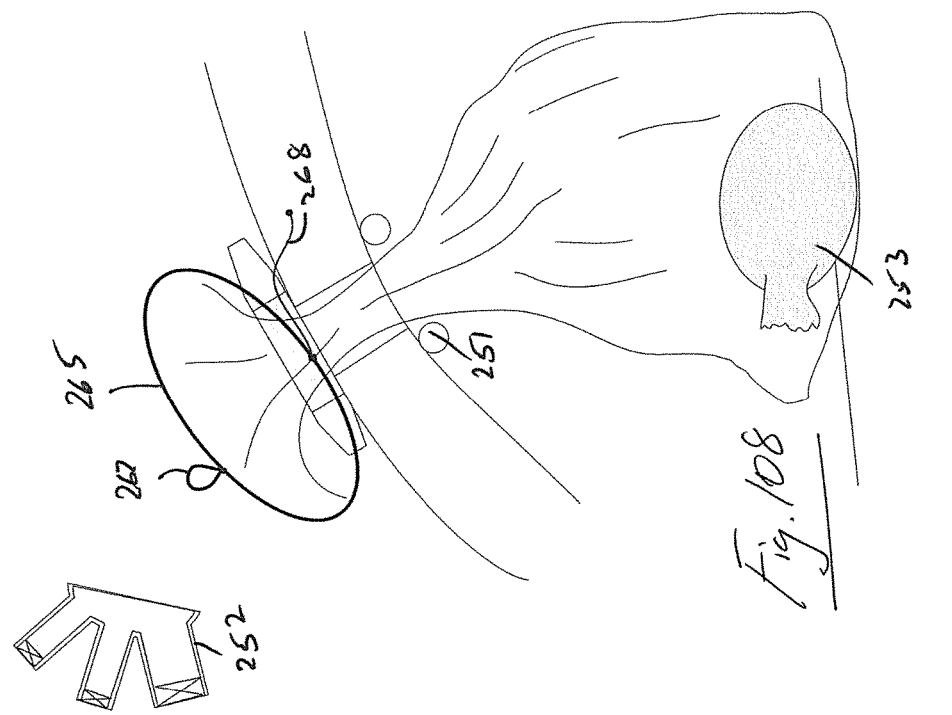
Figure 108:
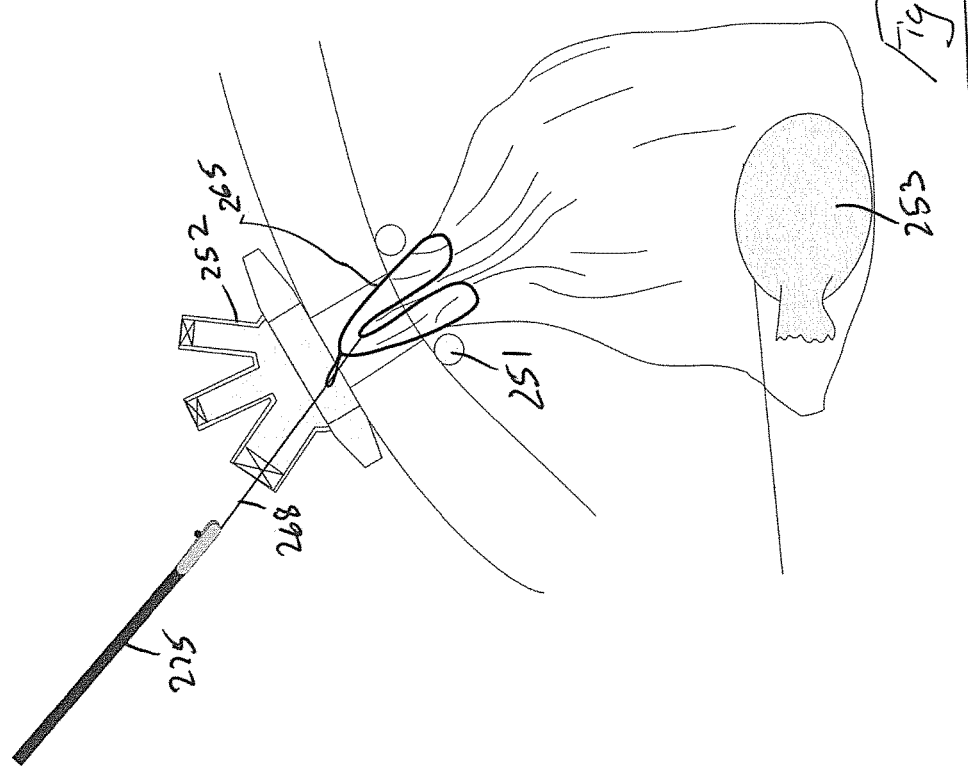
Figure 110:
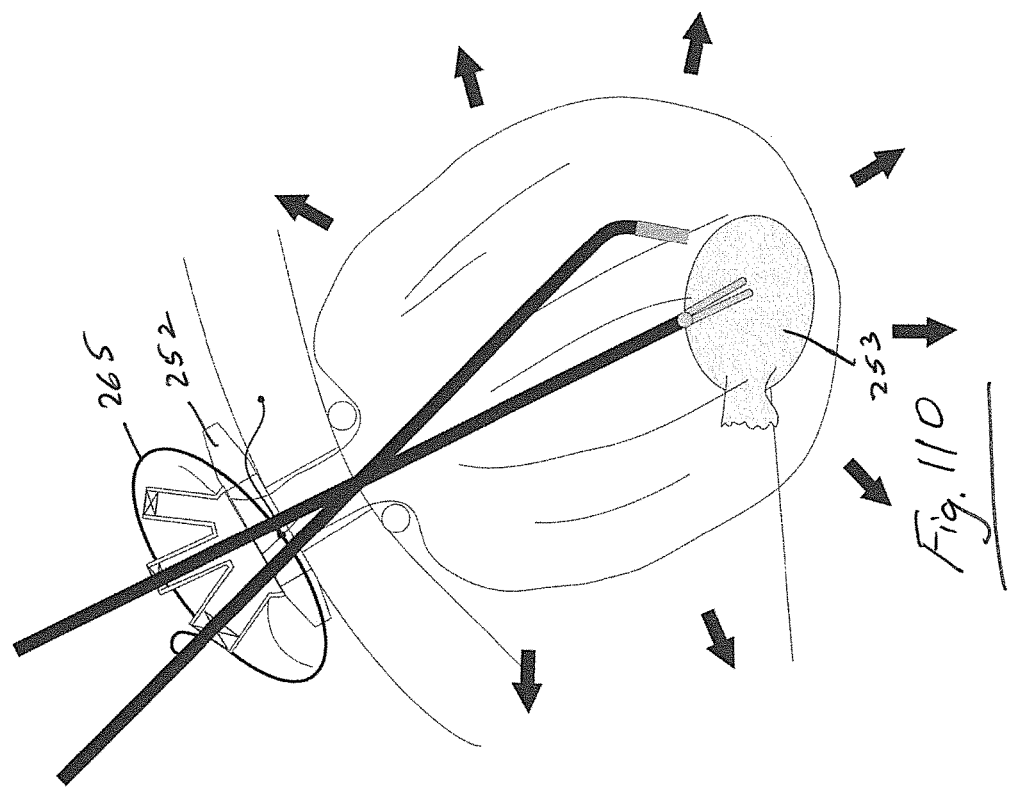
Figure 109:
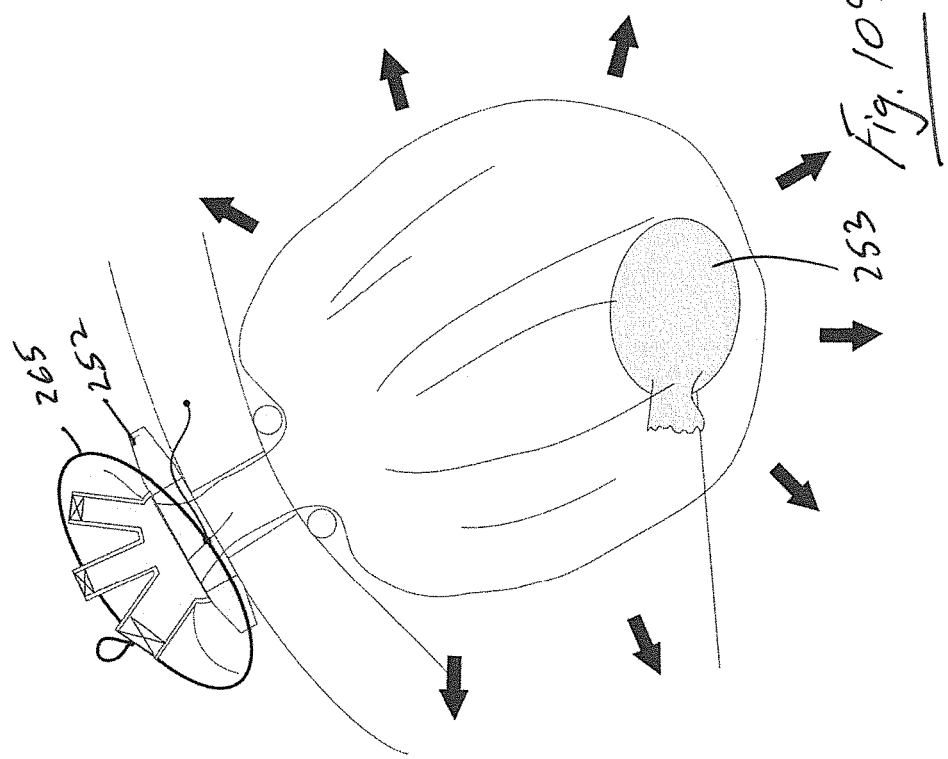

In FIG. 99 the bag device is placed in the delivery configuration in the cartridge or pouch 260. In this case the access port device 252 is in situ on top of the retractor 251 and the cartridge 260 is inserted through one lumen of the access port (FIG. 100). The plunger 261 is used to push the bag device 250 out of the cartridge 260 (FIG. 101). In this particular case the bag device is not tethered to the user, on delivery. On delivery into the body cavity, such as the abdomen, the retractor ring is free to move to its normally expanded configuration in which it opens up the bag opening (FIG. 102). The bag is folded in the delivery configuration. Using various instruments 270 a clinician manipulates a tissue specimen, organ or the like and then delivers it into the bag 250 through the open mouth of the bag (FIGS. 103, 104). FIGS. 105 and 106 illustrate one particular way in which the bag containing the tissue is retrieved. A grasper type instrument 275 is led through the proximal tether loop 267 and is used to grasp the distal tether 268 (FIG. 105). The distal tether 268 is pulled through the proximal tether loop 267 which ensures that the clinician has control over the bag as it is moved up towards the body opening (FIG. 106). As the retaining ring 265 engages with the retractor 251 it retracts allowing it to be pulled up through the body opening (FIG. 107). The access port 252 is removed and the retaining ring 265 is again free to expand (FIG. 108).

The access port 252 is re-attached and the bag is inflated to increase the operative field. The tissue sample can then readily by worked on (FIGS. 109, 110) without the risk of any potentially harmful material being released into the body cavity.

In some cases there may be a lock feature which prevents movement of one tether relative to the other in some directions. One such lock feature is illustrated in FIGS. 111 to 113. The distal tether has a one-way step feature 280 which permits the distal tether to pass through the proximal loop tether but once it has passed through this reverse movement is prevented as illustrated in FIG. 113. This ensures even greater control on the movement of the retaining ring 265 to aid closing of the bag as the ring 265 is being withdrawn.

As discussed above, the devices of the invention may be used in any suitable body cavities. One such use is in the colon and one embodiment for this use is illustrated in FIGS. 114 to 117. The device may be inserted as described above. Once in place and inflated a clinician can inspect the wall of the colon for any unusual features such as a growth. One such growth 280 is illustrated in FIG. 115. In this case, when a growth 280 is identified some or all of the growth 280 may be accessed by cutting a hole in the wall of the bag which remains in place by virtue of its engagement with the rest of the colon. Using various instruments, at least a portion of the growth 280 can be excised and removed through the bag. As in the other embodiments described a major advantage is that the tissue to be removed is retained in the bag which prevents potentially harmful material such as cancerous cells from being released in the body cavity.

Figure 118:
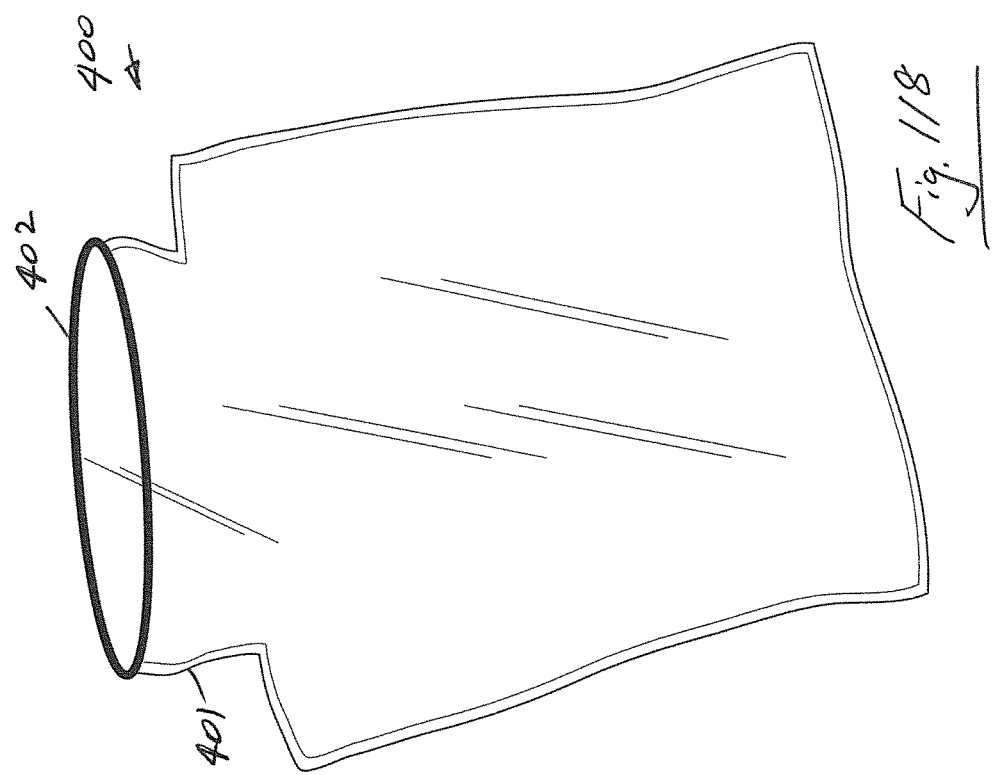
FIG. 118 is an isometric view of another device according to the invention.

Referring to FIG. 118 there is illustrated another bag device 400 of the invention. The bag device has a neck region 401 between a retaining ring 402 and the main body of the bag. Because the retaining ring 402 is of smaller diameter than that of the bag it is more easily inserted through an access port.

Figure 119:
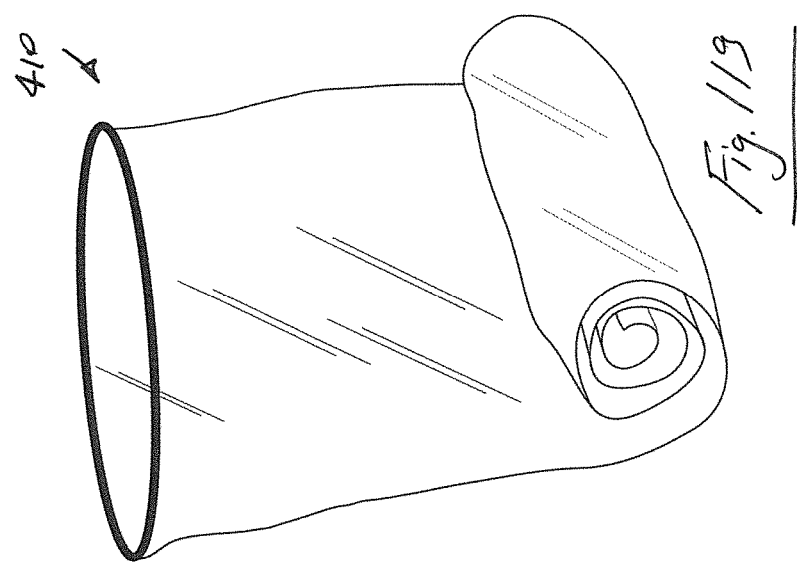
FIG. 119 is an isometric view of a further device according to the invention.

FIG. 119 illustrates another bag device 410 and shows how the main body of the bag may be folded in the retracted delivery configuration.

Various features of the invention are described and illustrated. It will be appreciated that at least some of the features described in relation to one embodiment may be used not only in the embodiment specifically described but also in other appropriate embodiments.

The invention is not limited to the embodiments hereinbefore described, with reference to the accompanying drawings, which may be varied in construction and detail.

The invention claimed is:

1. A tissue containment system, comprising:
    a tissue containment bag, including:
        an open end,
        a closed end opposite the open end,
        a wall extending from the open end to the closed end, wherein the wall has an interior surface, and
        a tissue containment chamber defined by the wall and the closed end;
    a guard for protecting at least part of the wall, wherein the guard includes a portion having:
        an exterior for engaging the interior surface of the wall, and
        an interior defining a passageway for receiving an instrument, wherein the portion of the guard is expandable toward the interior surface of the wall into an expanded configuration, and compressible into a compressed configuration,
    wherein the open end of the tissue containment bag includes an opening defined by an annular ring coupled to the wall, and
    wherein a diameter of the annular ring is greater than a diameter of a widest part of the guard.

2. The tissue containment system of claim 1, wherein the guard includes at least one longitudinal slit to facilitate at least one of expansion into the expanded configuration and compression into the compressed configuration.

3. The tissue containment system of claim 2, wherein the guard has a proximal part, a distal part, and an intermediate part between the proximal part and the distal part, and wherein the at least one longitudinal slit extends only in one or both of the intermediate part and the distal part.

4. The tissue containment system of claim 1, wherein the guard includes a proximal part, a distal part, and an intermediate part between the proximal part and the distal part, and wherein the portion of the guard includes at least one of the intermediate part and the distal part.

5. The tissue containment system of claim 1, wherein the guard has a proximal part, a distal part, and an intermediate part between the proximal part and the distal part, and wherein a width of the proximal part is greater than a width of the intermediate part.

6. The tissue containment system of claim 1, wherein the guard is sized such that the guard is separated from the annular ring by a circumferential gap while the exterior of the guard engages the interior surface of the wall.

7. The tissue containment system of claim 1, wherein the guard has a proximal part, and the wall of the guard at the proximal part is continuous about a circumference of the guard.

8. A tissue containment system, comprising:
    a tissue containment bag, including:
        an open end,
        a closed end opposite the open end,
        a wall extending from the open end to the closed end, wherein the wall has an interior surface and
        a tissue containment chamber defined by the wall and the closed end;
    a guard for protecting a portion of the wall, wherein the guard is configured to engage the interior surface of the wall, and wherein the guard includes:
        a first longitudinally-extending portion at a first side of the guard,
        a second longitudinally-extending portion at the first side of the guard, wherein the guard is compressible into a compressed configuration in which the first and second longitudinally-extending portions overlap along a radial direction,
    wherein the guard is expandable from the compressed configuration into an expanded configuration, and in the expanded configuration the overlap of the first and second longitudinally-extending portions along the radial direction is reduced.

9. The tissue containment system of claim 8, wherein the guard has a proximal part, a distal part, and an intermediate part between the proximal part and the distal part, and wherein a width of the proximal part is greater than a width of the intermediate part.

10. The tissue containment system of claim 8, wherein the guard includes a proximal part, a distal part, and an intermediate part between the proximal part and the distal part, and wherein the first and second longitudinally-extending portions are in at least one of the intermediate part and the distal part.

11. The tissue containment system of claim 8, wherein the guard has a proximal part, a distal part, and an intermediate part between the proximal part and the distal part, and wherein the first and second longitudinally-extending portions extend only in one or both of the intermediate part and the distal part.

12. The tissue containment system of claim 8, wherein the guard has a proximal part, and the wall of the guard at the proximal part is continuous about a circumference of the guard.

13. A tissue containment system, comprising:
a tissue containment bag, including:
   an open end,
   a closed end opposite the open end,
   a wall extending from the open end to the closed end, wherein the wall has an interior surface and
   a tissue containment chamber defined by the wall and the closed end;
a guard configured to engage the interior surface of the wall, and wherein the guard includes:
   a first longitudinally-extending portion at a first side of the guard,
   a second longitudinally-extending portion at the first side of the guard,
wherein the guard is expandable from a compressed configuration into an expanded configuration, and in the expanded configuration an overlap of the first and second longitudinally-extending portions along a radial direction is reduced,
wherein the open end of the tissue containment bag includes an opening defined by an annular ring coupled to the wall, and
wherein a diameter of the annular ring is greater than a diameter of a widest part of the guard.

14. The tissue containment system of claim 13, wherein the guard has a proximal part, a distal part, and an intermediate part between the proximal part and the distal part, and wherein a width of the proximal part is greater than a width of the intermediate part.

15. The tissue containment system of claim 13, wherein the guard has a proximal part, a distal part, and an intermediate part between the proximal part and the distal part, and wherein the first and second longitudinally-extending portions extend only in one or both of the intermediate part and the distal part.

16. The tissue containment system of claim 13, wherein the guard has a proximal part, and the wall of the guard at the proximal part is continuous about a circumference of the guard.

17. The tissue containment system of claim 13, wherein the guard has a proximal part, a distal part, and an intermediate part between the proximal part and the distal part, and wherein a width of the distal part is greater than a width of the intermediate part.

* * * * *